United States Patent [19]

Weidmann et al.

[11] Patent Number: 5,607,954

[45] Date of Patent: Mar. 4, 1997

[54] SULFONAMIDO- AND SULFONAMIDOCARBONYLPYRIDINE-2-CARBOXAMIDES AND THEIR PYRIDINE-N-OXIDES, PROCESS FOR THEIR PREPARATION AND THEIR USE AS PHARMACEUTICALS

[75] Inventors: Klaus Weidmann, Kronberg/Taunus; Martin Bickel, Bad Homburg; Volkmar Günzler-Pukall, Marburg, all of Germany

[73] Assignee: Hoechst Aktiengesellschaft, Frankfurt, Germany

[21] Appl. No.: 355,419

[22] Filed: Dec. 13, 1994

Related U.S. Application Data

[63] Continuation of Ser. No. 28,438, Mar. 9, 1993, abandoned.

[30] Foreign Application Priority Data

| Mar. 24, 1992 | [DE] | Germany | 42 09 424.0 |
| Nov. 14, 1992 | [DE] | Germany | 42 38 506.7 |

[51] Int. Cl.⁶ ............ C07D 213/30; A61K 31/44
[52] U.S. Cl. ............................. 514/355; 546/316
[58] Field of Search ................. 546/316; 514/355

[56] References Cited

U.S. PATENT DOCUMENTS

| 4,717,727 | 1/1988 | Günzler et al. | 514/354 |
| 4,968,670 | 11/1990 | Brocks et al. | 514/18 |
| 5,037,839 | 8/1991 | Bickel et al. | 514/354 |
| 5,153,208 | 10/1992 | Bickel et al. | 514/332 |

FOREIGN PATENT DOCUMENTS

| 600084 | 8/1990 | Australia . |
| 2023952 | 2/1991 | Canada . |
| 2045868 | 12/1991 | Canada . |

*Primary Examiner*—Jane Fan
*Attorney, Agent, or Firm*—Barbara V. Maurer

[57] ABSTRACT

The invention relates to sulfonamido- and sulfonamidocarbonylpyridine-2-carboxa of the formula I

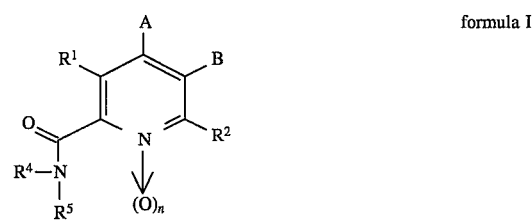

formula I and their use as pharmaceuticals, in particular against fibrotic diseases.

8 Claims, No Drawings

SULFONAMIDO- AND SULFONAMIDOCARBONYLPYRIDINE-2-CARBOXAMIDES AND THEIR PYRIDINE-N-OXIDES, PROCESS FOR THEIR PREPARATION AND THEIR USE AS PHARMACEUTICALS

This is a continuation, of a prior application, Ser. No. 028,438 filed Mar. 9, 1993, now abandoned.

The invention relates to sulfonylamino- or sulfonylaminocarbonyl carbonylpyridine-2-carboxamides and their pyridine-N-oxides, and to their use as pharmaceuticals against fibrotic diseases.

Compounds which inhibit the enzymes proline hydroxylase and lysine hydroxylase, effect very selective inhibition of collagen biosynthesis by affecting the collagen-specific hydroxylation reactions. In the course thereof, protein-bound proline or lysine is hydroxylated by the enzymes proline hydroxylase or lysine hydroxylase. If this reaction is suppressed by inhibitors, an under-hydroxylated collagen molecule which is not capable of functioning is formed, which can be released into the extracellular space by the cells only in a small amount. The underhydroxylated collagen can additionally not be incorporated into the collagen matrix and is very easily degraded proteolytically. As a result of these effects, the total amount of extracellularly deposited collagen is reduced.

Inhibitors of proline hydroxylase are therefore suitable substances in the therapy of diseases in which the deposition of collagens decisively contributes to the clinical picture. These include, inter alia, fibroses of the lungs, liver and skin (scleroderma) and atherosclerosis.

It is known that the enzyme proline hydroxylase is effectively inhibited by pyridine-2,4- and -2,5-dicarboxylic acid (K. Majamaa et al., Eur. J. Biochem. 138 (1984) 239–245). However, these compounds are only effective as inhibitors in cell culture at very high concentrations (Tschank, G. et al., Biochem. J. 238 (1987) 625–633).

DE-A 3,432,094 describes pyridine-2,4- and -2,5-dicarboxylic acid diesters having 1–6 carbon atoms in the ester alkyl moiety as pharmaceuticals for the inhibition of proline hydroxylase and lysine hydroxylase.

However, these lower alkyl diesters have the disadvantage that they are cleaved too rapidly in the body to give the acids and do not reach their site of action in the cell in sufficiently high concentration and are thus less suitable for possible administration as pharmaceuticals.

DE-A 3,703,959, DE-A 3,703,962 and DE-A 3,703,963 described in general form mixed esters/amides, and higher alkyl diesters and diamides of pyridine-2,4- and -2,5-dicarboxylic acid which effectively inhibit collagen biosynthesis in the animal model.

The object, then, was to seek compounds which are more strongly antifibrotic than the compounds known to date.

The object is achieved by the provision of sulfonylamino- or sulfonylaminocarbonyl pyridine-2-carboxamides and their pyridine-N-oxides of the formula I

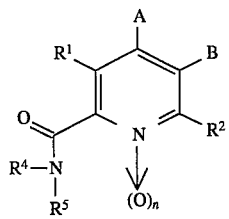

Formula I in which

A is $R^3$ and B is X—$NR^6R^7$ or

B is $R^3$ and A is X—$NR^6R^7$

X is a single bond or —CO— and $R^1$, $R^2$ and $R^3$ are identical or different and are hydrogen, unsubstituted or substituted ($C_1$–$C_6$)-alkyl, ($C_1$–$C_6$)-alkoxy, halogen, in particular fluorine, chlorine or bromine, nitrile, hydroxyl or amino, $R^6$ is hydrogen, ($C_1$–$C_6$)-alkyl or an N-protective group such as ($C_1$–$C_8$)-alkanoyl, ($C_1$–$C_6$)-alkylcarbamoyl, ($C_1$–$C_6$)-alkoxycarbonyl, benzyloxycarbonyl, ($C_1$–$C_{10}$)-acyloxy-($C_1$–$C_6$)-alkyl, preferably ($C_1$–$C_{10}$)-alkanoyloxy-($C_1$–$C_6$)-alkyl, benzoyloxy-($C_1$–$C_6$)-alkyl, benzyloxycarbonyloxy-($C_1$–$C_6$)-alkyl or ($C_1$–$C_6$)-alkoxycarbonyloxy-($C_1$–$C_6$)-alkyl, a 1-, 2-, 3- or 4-valent physiologically utilizable cation, in particular $Na^\oplus$, $K^\oplus$, $Mg^{2\oplus}$, $Ca^{2\oplus}$, $Al^{3\oplus}$ or an ammonium ion, optionally substituted 1–3 times by ($C_1$–$C_8$)-alkyl, ($C_1$–$C_8$)-hydroxyalkyl, ($C_1$–$C_4$)-alkoxy-($C_1$–$C_8$)-alkyl, phenyl, benzyl or ($C_1$–$C_8$)-alkyl which can be substituted 1 to 3 times by hydroxyl or ($C_1$–$C_4$)-alkoxy, or a cation of a basic amino acid derivative, $R^7$ is a radical of the formula II, excluding —$SO_2H$,

   (II)

in which

Y is —$SO_2$— or —CO—,

C is a bond or a branched or unbranched aliphatic ($C_1$–$C_{16}$)-alkanediyl or cycloaliphatic ($C_3$–$C_{10}$)-alkanediyl radical or a branched or unbranched ($C_2$–$C_{16}$)-alkenediyl or cycloalkenediyl radical, or a ($C_2$–$C_{16}$)-alkynediyl radical or a ($C_2$–$C_{16}$)-alkenynediyl radical, each of which can contain one or more C—C multiple bonds, U is a bond or hydrogen or a radical from the series of the following hetero atom groups —CO—, —O(CO)—, —(CO)—O—, —(CO)NR—, —NR(CO)—, —O—, —SO—, —$SO_2$—, —NR in which R is ($C_1$–$C_3$)-alkyl or hydrogen, r is 1, 2, 3 or 4, D is a bond or hydrogen or a branched or unbranched aliphatic ($C_1$–$C_{10}$)-alkanediyl radical, or a branched or unbranched ($C_1$–$C_{10}$)-alkenediyl radical, a ($C_2$–$C_{10}$)-alkynediyl radical or a ($C_2$–$C_{10}$)-alkenynediyl radical, each of which can contain one or more C—C multiple bonds, W is a bond or hydrogen or a ($C_3$–$C_{10}$)-cycloaliphatic alkyl, alkenyl, alkynyl or alkenynyl radical or a ($C_6$–$C_{16}$)-aryl radical or a 5- or 6-membered heteroaryl radical, where at least one of the variables C or D or W is not a bond and U is only a hetero atom group if C is not a bond or if D and/or W are not a bond and C and/or W, if these are not a bond or hydrogen and are preferably substituted for their part $R^4$ and $R^5$ independently of one another are hydrogen or A) an unsubstituted or substituted ($C_1$–$C_{12}$)-alkoxy radical, ($C_3$–$C_8$)-cycloalkoxy radical, ($C_6$–$C_{12}$)-aryloxy radical or a ($C_7$–$C_{11}$)-aralkoxy radical, which is monosubstituted or polysubstituted, preferably monosubstituted or disubstituted, by halogen, trifluoromethyl, ($C_1$–$C_6$)-alkoxy, hydroxyl, ($C_1$–$C_6$)-hydroxyalkyl, NR'R" or cyano or B) an unsubstituted or substituted, branched or unbranched, aliphatic or cycloaliphatic ($C_1$–$C_{12}$)- alkyl radical, $(C_1–C_{12})$-alkenyl radical or a $(C_1–C_{12})$-alkynyl radical, or C) an unsubstituted or substituted $(C_6–C_{12})$-aryl radical, $(C_7–C_{11})$-aralkyl radical or a hetaryl radical, R' and R" are identical or different and are hydrogen, $(C_6–C_{12})$-aryl, $(C_1–C_8)$-alkyl, $(C_1–C_8)$-alkyl-carbonyl, $(C_7–C_{11})$-aralkylcarbonyl or $(C_6–C_{12})$-arylcarbonyl or, with the nitrogen atom, form a saturated heterocyclic ring, preferably a 5- or 6-membered ring, and n is 0 or 1, f is 1 to 8, preferably 1 to 5, g is 0, 1 to (2f+1) and x is 0 to 8, preferably 0 to 1.

Preferred compounds of the formula I are those in which $R^1$, $R^2$ and $R^3$ are identical or different and are hydrogen, $(C_1–C_6)$-alkyl, $(C_1–C_6)$-alkoxy, halogen, in particular fluorine, chlorine or bromine, nitrile, hydroxyl, amino, optionally mono- or disubstituted by $(C_1–C_4)$-alkyl, hydroxy-$(C_1–C_4)$-alkyl or $(C_1–C_6)$-alkyl-carbonyloxy, $R^6$ is hydrogen, $(C_1–C_6)$-alkyl or an N-protective group such as $(C_1–C_8)$-alkanoyl, $(C_1–C_6)$-alkylcarbamoyl, $(C_1–C_6)$-alkoxycarbonyl, benzyloxycarbonyl, $(C_1–C_{10})$-acyloxy-$(C_1–C_6)$-alkyl, preferably $(C_1–C_{10})$-alkanoyloxy-$(C_1–C_6)$-alkyl, benzoyloxy-$(C_1–C_6)$-alkyl, benzyloxycarbonyloxy-$(C_1–C_6)$-alkyl or $(C_1–C_6)$-alkoxycarbonyloxy-$(C_1–C_6)$-alkyl, a 1-, 2-, 3- or 4-valent physiologically utilizable cation, in particular $Na^\oplus$, $K^\oplus$, $Mg^{2\oplus}$, $Ca^{2\oplus}$, $Al^{3\oplus}$ or an ammonium ion, optionally substituted 1–3 times by $(C_1–C_8)$-alkyl, $(C_1–C_8)$-hydroxyalkyl, $(C_1–C_4)$-alkoxy-$(C_1–C_8)$-alkyl, phenyl, benzyl or $(C_1–C_8)$-alkyl which can be substituted 1 to 3 times by hydroxyl or $(C_1–C_4)$-alkoxy, or a cation of a basic amino acid derivative, $R^7$ is a radical of the formula II, excluding —$SO_2H$,

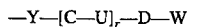  (II)

in which

Y is —$SO_2$— or —CO—,

C is a bond or a branched or unbranched aliphatic $(C_1–C_{16})$-alkanediyl or cycloaliphatic $(C_3–C_{10})$-alkanediyl radical or a branched or unbranched $(C_2–C_{16})$-alkenediyl or cycloalkenediyl radical, or a $(C_2–C_{16})$-alkynediyl radical or a $(C_2–C_{16})$-alkenynediyl radical, each of which can contain one or more C—C multiple bonds, U is a bond or hydrogen or a radical from the series of the following hetero atom groups —CO—, —O(CO)—, —(CO)—O—, —(CO)NR—, —NR(CO)—, —O—, —SO—, —$SO_2$—, —NR in which R is $(C_1–C_3)$-alkyl, $(C_1–C_8)$-alkanoyl, $(C_7–C_{16})$-aralkanoyl, $(C_6–C_{12})$-aroyl or hydrogen, r is 1, 2, 3 or 4, D is a bond or hydrogen or a branched or unbranched aliphatic $(C_1–C_{10})$-alkanediyl radical, or a branched or unbranched $(C_1–C_{10})$-alkenediyl radical, a $(C_2–C_{10})$-alkynediyl radical or a $(C_2–C_{10})$-alkenynediyl radical, each of which can contain one or more C—C multiple bonds, W is a bond or hydrogen or a $(C_3–C_{10})$-cycloaliphatic alkyl, alkenyl, alkynyl or alkenynyl radical or a $(C_6–C_{16})$-aryl radical or a 5- or 6-membered heteroaryl radical, where at least one of the variables C or D or W is not a bond and U is only a hetero atom group if C is not a bond or if D and/or W are not a bond and C and/or W, if these are not a bond or hydrogen, are preferably substituted for their part by a combination of up to 5 identical or different substitutents from the series comprising hydroxyl, halogen, cyano, trifluoromethyl, nitro, carboxyl, $(C_1–C_{12})$-alkyl, $(C_3–C_8)$-cycloalkyl, $(C_6–C_{12})$-aryl, $(C_7–C_{16})$-aralkyl, $(C_3–C_{12})$-alkenyl, $(C_3–C_{12})$-alkynyl, $(C_1–C_{12})$-alkoxy, $(C_1–C_{12})$-alkoxy-$(C_1–C_{12})$-alkyl, $(C_1–C_{12})$-alkoxy-$(C_1–C_{12})$-alkoxy, $(C_6–C_{12})$-aryloxy, $(C_7–C_{16})$-aralkyloxy, $(C_1–C_8)$-hydroxyalkyl, —O—$[CH_2]_xC_fH_{(2f+1-g)}F_g$, —$OCF_2Cl$, —$OCF_2$—$CHFCl$, $(C_1–C_{12})$-alkylcarbonyl, $(C_3–C_8)$-cycloalkylcarbonyl, $(C_6–C_{12})$-arylcarbonyl, $(C_7–C_{16})$-aralkylcarbonyl, cinnamoyl, $(C_3–C_{12})$-alkenylcarbonyl, $(C_3–C_{12})$-alkynylcarbonyl, $(C_1–C_{12})$-alkoxycarbonyl, $(C_1–C_{12})$-alkoxy-$(C_1–C_{12})$-alkoxycarbonyl, $(C_6–C_{12})$-aryloxycarbonyl, $(C_7–C_{16})$-aralkoxycarbonyl, $(C_3–C_8)$-cycloalkoxycarbonyl, $(C_3–C_{12})$-alkenyloxycarbonyl, $(C_3–C_{12})$-alkynyloxycarbonyl, $(C_1–C_{12})$-alkylcarbonyloxy, $(C_3–C_8)$-cycloalkylcarbonyloxy, $(C_6–C_{12})$-arylcarbonyloxy, $(C_7–C_{16})$-aralkylcarbonyloxy, cinnamoyloxy, $(C_3–C_{12})$-alkenylcarbonyloxy, $(C_3–C_{12})$-alkynylcarbonyloxy, $(C_1–C_{12})$-alkoxycarbonyloxy, $(C_1–C_{12})$-alkoxy-$(C_1–C_{12})$-alkoxycarbonyloxy, $(C_6–C_{12})$-aryloxycarbonyloxy, $(C_7–C_{16})$-aralkyloxycarbonyloxy, $(C_3–C_8)$-cycloalkoxycarbonyloxy, $(C_3–C_{12})$-alkenyloxycarbonyloxy, $(C_3–C_{12})$-alkynyloxycarbonyloxy, carbamoyl, N-$(C_1–C_{12})$-alkylcarbamoyl, N,N-di-$(C_1–C_{12})$-alkylcarbamoyl, N-$(C_3–C_8)$-cycloalkylcarbamoyl, N-$(C_6–C_{16})$-arylcarbamoyl, N-$(C_7–C_{16})$-aralkylcarbamoyl, N-$(C_1–C_{10})$-alkyl-N-$(C_6–C_{16})$-arylcarbamoyl, N-$(C_1–C_{10})$-alkyl-N-$(C_7–C_{16})$-aralkylcarbamoyl, N-(($C_1–C_{10}$)-alkoxy-$(C_1–C_{10})$-alkyl)carbamoyl, N-(($C_6–C_{16}$)-aryloxy-$(C_1–C_{10})$-alkyl)carbamoyl, N-(($C_7–C_{16}$)-aralkyloxy-$(C_1–C_{10})$-alkyl)carbamoyl, N-$(C_1–C_{10})$-alkyl-N-(($C_1–C_{10}$)-alkoxy-$(C_1–C_{10})$-alkyl)carbamoyl, N-$(C_1–C_{10})$-alkyl-N-(($C_6–C_{16}$)-aryloxy-$(C_1–C_{10})$-alkyl)carbamoyl, N-$(C_1–C_{10})$-alkyl-N-(($C_7–C_{16}$)-aralkyloxy-$(C_1–C_{10})$-alkyl)carbamoyl, carbamoyloxy, N-alkylamino, $(C_1–C_{12})$-alkylcarbamoyloxy, N,N-di-$(C_1–C_{12})$-alkylcarbamoyloxy, N-$(C_3–C_8)$-cycloalkylcarbamoyloxy, N-$(C_6–C_{16})$-arylcarbamoyloxy, N-$(C_7–C_{16})$-aralkylcarbamoyloxy, N-$(C_1–C_{10})$-alkyl-N-$(C_6–C_{12})$-arylcarbamoyloxy, N-$(C_1–C_{10})$-alkyl-N-$(C_7–C_{16})$-aralkylcarbamoyloxy, N-(($C_1–C_{10}$)-alkoxy-$(C_1–C_{10})$-alkyl)carbamoyloxy, N-(($C_6–C_{16}$)-aryloxy-$(C_1–C_{10})$-alkyl)carbamoyloxy, N-(($C_7–C_{16}$)-aralkyloxy-$(C_1–C_{10})$alkyl)carbamoyloxy, N-$(C_1–C_{10})$-alkyl-N-(($C_1–C_{10}$)-alkoxy-$(C_1–C_{10})$-alkyl)carbamoyloxy, N-$(C_1–C_{10})$-alkyl-N-(($C_6–C_{16}$)-aryloxy-$(C_1–C_{10})$alkyl)carbamoyloxy, N-$(C_1–C_{10})$-alkyl-N-(($C_7–C_{16}$)-aralkyloxy-$(C_1–C_{10})$-alkyl)carbamoyloxy, $(C_1–C_{12})$-alkylamino, di-$(C_1–C_{12})$-alkylamino, $(C_3–C_8)$-cycloalkylamino, $(C_3–C_{12})$-alkenylamino, $(C_3–C_{12})$-alkynylamino, N-$(C_6–C_{12})$-arylamino, N-$(C_7–C_{11})$-aralkylamino, N-$(C_1–C_{10})$-alkyl$(C_7–C_{10})$- aralkylamino, N-($C_1$–$C_{10}$)-alkyl-N-($C_6$–$C_{12}$)-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, sulfamoyl, N-($C_1$–$C_{10}$)-alkylsulfamoyl, N,N-di-($C_1$–$C_{10}$)-alkylsulfamoyl, ($C_3$–$C_8$)-cycloalkylsulfamoyl, N-($C_6$–$C_{16}$)-arylsulfamoyl, N-($C_7$–$C_{16}$)-aralkylsulfamoyl, N-($C_1$–$C_{10}$)-alkyl-N-($C_6$–$C_{16}$)-arylsulfamoyl, N-($C_1$–$C_{10}$)-alkyl-N-($C_7$–$C_{16}$)-aralkylsulfamoyl, ($C_1$–$C_{10}$)-alkylsulfonamido, N-(($C_1$–$C_{10}$)-alkyl)-($C_1$–$C_{10}$)-alkylsulfonamido, ($C_7$–$C_{16}$)-aralkylsulfonamido, N-(($C_1$–$C_{10}$)-alkyl-$C_7$–$C_{16}$)-aralkylsulfonamido, where the radicals which contain an aryl radical can be substituted, for their part, on the aryl by 1, 2, 3, 4 or 5 identical or different substituents from the series comprising hydrogen, hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_6$–$C_{12}$)-aryloxy, ($C_7$–$C_{16}$)-aralkyloxy, ($C_1$–$C_8$)-hydroxyalkyl, —O—[$CH_2$]$_x$$C_f$$H_{(2f+1-g)}$$F_g$, —$OCF_2Cl$, —$OCF_2$—CHFCl, ($C_1$–$C_{12}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_3$–$C_{12}$)-alkenylcarbonyl, ($C_3$–$C_{12}$)-alkynylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_3$–$C_{12}$)-alkenylcarbonyloxy, ($C_3$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_3$–$C_{12}$)-alkenyloxycarbonyloxy, ($C_3$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)arylcarbamoyl, N-(($C_1$–$C_{10}$)-alkoxy-($C_1$–$C_{10}$)alkyl)carbamoyl, N-(($C_6$–$C_{16}$)-aryloxy-($C_1$–$C_{10}$)-alkyl)carbamoyl, N-(($C_7$–$C_{16}$)-aralkyloxy-$C_1$–$C_{10}$-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)alkyl)carbamoyl, N-($C_1$–$C_{10}$)-alkyl-N-(($C_7$–$C_{16}$)aralkyloxy-($C_1$–$C_{10}$)-alkyl)carbamoyl, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{16}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkoxy-($C_1$–$C_{10}$)-alkyl)carbamoyloxy, N-(($C_6$–$C_{16}$)-aryloxy-($C_1$–$C_{10}$)-alkyl) carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{16}$)-aryloxy-($C_1$–$C_{10}$)-alkyl)carbamoyloxy, N-($C_1$–$C_{10}$)-alkyl-N-(($C_7$–$C_{16}$)-aralkyloxy-($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-($C_1$–$C_{10}$)-alkyl-N-($C_7$–$C_{16}$)-aralkylamino, N-($C_1$–$C_{10}$)-alkyl-N-($C_6$–$C_{12}$)-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N,-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, sulfamoyl, N-($C_1$–$C_{10}$)-alkylsulfamoyl, N,N-di-($C_1$–$C_{10}$)-alkylsulfamoyl, ($C_3$–$C_8$)-cycloalkylsulfamoyl, N-($C_6$–$C_{16}$)-arylsulfamoyl, N-($C_7$–$C_{16}$)-aralkylsulfamoyl, N-($C_1$–$C_{10}$)-alkyl-N-($C_6$–$C_{16}$)-arylsulfamoyl, N-($C_1$–$C_{10}$)-alkyl-N-($C_7$–$C_{16}$)-aralkylsulfamoyl, ($C_1$–$C_{10}$)-alkylsulfonamido, N-(($C_1$–$C_{10}$)-alkyl)-($C_1$–$C_{10}$)-alkylsulfonamido, ($C_7$–$C_{16}$)-aralkylsulfonamido, N-(($C_1$–$C_{10}$)-alkyl-($C_7$–$C_{16}$)-aralkylsulfonamido, $R^4$ and $R^5$ independently of one another are hydrogen or
A) an unsubstituted or substituted ($C_1$–$C_{12}$)-alkoxy radical, ($C_3$–$C_8$)-cycloalkoxy radical, ($C_6$–$C_{12}$)-aryloxy radical or a ($C_7$–$C_{11}$)-aralkyloxy radical, which is monosubstituted or polysubstituted, preferably monosubstituted or disubstituted, by halogen, trifluoromethyl, $(C_1-C_6)$-alkoxy, hydroxyl, $(C_1-C_6)$-hydroxyalkyl, NR'R" or cyano or
B) an unsubstituted or substituted, branched or unbranched, aliphatic or cycloaliphatic $(C_1-C_{12})$-alkyl radical, $(C_1-C_{12})$-alkenyl radical or a $(C_1-C_{12})$-alkynyl radical, or
C) an unsubstituted or substituted $(C_6-C_{12})$-aryl radical, $(C_7-C_{11})$-aralkyl radical or a hetaryl radical, where the radicals B) and C) are, in particular monosubstituted or polysubstituted, preferably monosubstituted or disubstituted by
hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, $-O-[CH_2]_xC_fH_{(2f+1-g)}F_g$, $-OCF_2Cl$, $-OCF_2-CHFCl$,
$(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl,
$(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkylcarbonyl, $(C_3-C_8)$-cycloalkoxycarbonyl, $(C_3-C_{12})$-alkenylcarbonyl, $(C_3-C_{12})$-alkynyloxycarbonyl,
$(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy,
$(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy,
carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl,
N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)-carbamoyl, N-$(C_1-C_{10})$-alkyl-N-$((C_7-C_{16})$-aralkyloxy-$(C_1-C_{10})$-alkyl)carbamoyl, hydroxy-$(C_1-C_6)$-alkylcarbamoyl, $(C_1-C_6)$-alkoxy-$(C_1-C_6)$-alkylcarbamoyl or acyloxy-$(C_1-C_6)$-alkylcarbamoyl,
a carbamoyl radical of the formula III $$-CO-P \quad (III)$$

in which
P is a polypeptide bonded via one of its amino groups or an amino acid or amino acid derivative (ester or amide) bonded via its amino group,
carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy,
N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl)carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy,
N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy-$(C_1-C_{10})$-alkyl)carbamoyloxy,
amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkylamino, N-alkylarylamino, $(C_1-C_{12})$-alkoxyamino, $(C_1-C_{12})$-alkoxy-N-$(C_1-C_{10})$-alkylamino,
$(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino,
$(C_1-C_{12})$-alkanoylamino-$(C_1-C_8)$alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl,
$(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl,
a radical of the formula IV $$-O-R^8 \quad (IV)$$

in which $R^8$ is an amino acid bonded via its acyl radical, its N-protected derivative or an alcohol protective group,
where the radicals which contain an aryl radical can be substituted, for their part, on the aryl by 1, 2, 3, 4 or 5 identical or different substituents from the series comprising hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, $-O-[CH_2]_xC_fH_{(2f+1-g)}F_g$, $-OCF_2Cl$, $-OCF_2Cl$, $-OCF_2-CHFCl$,
$(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl,
$(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{16})$-arylcarbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl)carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy-$(C_1-C_{10})$-alkyl)-carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-aryl- amino, N-$(C_7-C_{11})$-aralkylamino, N-$(C_1-C_{12})$-alkyl-N-$(C_7-C_{11})$-aralkylamino, N-$(C_1-C_{12})$-alkyl-N-$(C_6-C_{12})$-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, R' and R" are identical or different and are hydrogen, $(C_6-C_{12})$-aryl, $(C_1-C_8)$-alkyl, $(C_1-C_8)$-alkylcarbonyl, $(C_7-C_{11})$-aralkylcarbonyl or $(C_6-C_{12})$-arylcarbonyl or, with the nitrogen atom, form a saturated heterocyclic ring, preferably a 5- or 6-membered ring, and n is 0 or 1, f is 1 to 8, preferably 1 to 5, g is 0, 1 to (2f+1) and x is 0 to 8, preferably 0 to 1.

Aryl, aryloxy, heteroaryl or heteroaryloxy compounds are understood as meaning, in particular, phenyl, biphenyl or naphthyl or unsubstituted 5- and 6-membered heteroaromatic rings having 1, 2 or 3 nitrogen and/or oxygen and/or sulfur atoms, such as pyridyl, pyridazyl, pyrimidyl, pyrazolyl, imidazolyl, triazolyl, thienyl, oxazolyl and thiazolyl derivatives, and their benzo-fused derivatives.

Of the amino acids mentioned, in particular the natural α-amino acids are preferred.

Amino protective groups are understood in particular as meaning those groups which are described in R. Geiger and W. König "The Peptides" Volume 3, "Protection of Functional Groups in Peptide Synthesis", E. G. Gross, J. Meienhofer Edit, Academic Press, New York (1981), in particular pages 7–46.

Such groups are also described in A. Hubbuch, Schutzgruppen in der Peptidsynthese (Protective groups in peptide synthesis), Kontakte 3/79, pages 14–23.

The following amino protective groups are particularly preferred:

acetamidomethyl, 1-adamantyloxycarbonyl, 1-(1-adamantyl)-1-methyl-ethoxycarbonyl, allyloxycarbonyl, tert-butoxycarbonyl, 1-(4-biphenyl)-1-methyl-ethoxycarbonyl, α,α-dimethyl-3,5-dimethoxybenzyloxycarbonyl, 4-dihydroxyborylbenzyloxycarbonyl, 9-fluorenylmethyloxycarbonyl, isobornyloxycarbonyl, 1-methyl-cyclobutoxycarbonyl, 4-methoxybenzyloxycarbonyl, methylsulfonylethyloxycarbonyl, 4-pyridylmethyloxycarbonyl, 2,2,2-trichloro-tert-butoxycarbonyl, benzyloxycarbonyl, halogen-substituted benzyloxycarbonyl, 4-nitrobenzyloxycarbonyl, 2-phosphonoethyloxycarbonyl, phenylsulfonylethoxycarbonyl, toluenesulfonylethoxycarbonyl, 2,3,5-trimethyl-4-methoxy-phenylsulfonyl.

Of the compounds of the formula I whose amino groups are protected, those are preferred whose protected amino groups are part of this amino acid $R^8$.

Suitable alcohol protective groups are, in particular, substituted or unsubstituted methyl ethers, ethyl ethers, benzyl ethers, silyl ethers, esters, carbonates or sulfonates.

The following compounds are included under these:

As substituted methyl ethers:

methoxymethyl, methylthiomethyl, t-butylthiomethyl, (phenyldimethlsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl-S,S-dioxo, 1-[2-chloro-4-methyl)-phenyl]-4-methoxypiperidin-4-yl, 1,4-dioxan-2-yl, tetrahydrofuranyl, tetrahydrothiofuranyl.

As substituted ethyl ethers:

1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl.

As substituted benzyl ethers:

p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl-N-oxide, diphenylmethyl, p,p'-dinitrobenzhydryl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinooxyphenyl)methyl, 4,4',4"-tris(benzoyloxyphenyl)methyl, 3-(imidazol-1,4'-methyl)-bis-(4',4"-dimethoxyphenyl)-methyl, 1,1-bis(4-methoxyphenyl)-1'-pyrenylmethyl, 9-anthryl, 9-(9-phenyl)xanthenyl, 9-phenyl-10-oxo)anthryl.

As silyl ethers:

trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxyphenylsilyl.

As esters:

formates, benzoylformates, acetates, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate (mesitoate).

As carbonates:

methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonates, 4-ethoxy-1-naphthyl, methyl dithiocarbonates.

Other esters:

2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), O-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, 2,4-dinitrophenylsulfenate.

As sulfonates:

sulfates, methanesulfonate (mesylate), benzylsulfonate, tosylates.

The following protective groups are particularly preferred:

$(C_1-C_6)$-alkanoyl, $(C_1-C_8)$-alkylcarbamoyl, di-$(C_1-C_8)$-alkylcarbamoyl, N-$(C_3-C_8)$-cycloalkylcarbamoyl, $(C_1-C_6)$-alkoxycarbonyl, $(C_6-C_{12})$-aryloxycarbonyl, $(C_7-C_{11})$-aralkyloxycarbonyl, in particular benzyloxycarbonyl, $(C_6-C_{12})$-arylcarbonyl, $(C_7-C_{11})$-aralkylcarbonyl, $(C_1-C_6)$-alkyl, $(C_1-C_6)$-alkoxy-$(C_1-C_6)$-alkyl, carbamoyl-$(C_1-C_6)$-alkyl esters, $(C_1-C_{10})$-acyloxy-$(C_1-C_6)$-alkyl, preferably $(C_1-C_{10})$-alkanoyloxy-$(C_1-C_6)$-alkyl, benzyloxy-$(C_1-C_6)$-alkyl, benzyloxycarbonyloxy-$(C_1-C_6)$-alkyl, $(C_1-C_6)$-alkoxycarbonyloxy-$(C_1-C_6)$-alkyl, amino acid esters, or tetrahydropyranyl.

Among these, preferred compounds of the formula I are those in which

X is a single bond or —CO—, $R^1$, $R^2$ and $R^3$ are identical or different and are hydrogen, $(C_1-C_6)$-alkyl, $(C_1-C_6)$-alkoxy, halogen, in particular fluorine and chlorine, hydroxyl, amino or hydroxy-$(C_1-C_4)$-alkyl, $R^6$ is hydrogen, $(C_1-C_6)$-alkyl or an N-protective group such as $(C_1-C_8)$-alkanoyl, $(C_1-C_6)$-alkylcarbamoyl, $(C_1-C_6)$-alkoxycarbonyl, benzyloxycarbonyl, $(C_1-C_{10})$-acyloxy-$(C_1-C_6)$-alkyl, preferably $(C_1-C_{10})$-alkanoyloxy-$(C_1-C_6)$-alkyl, benzoyloxy-$(C_1-C_6)$-alkyl, benzyloxycarbonyloxy-$(C_1-C_6)$-alkyl, or $(C_1-C_6)$-alkoxycarbonyloxy-$(C_1-C_6)$-alkyl, a 1-, 2-, 3- or 4-valent physiologically utilizable cation, in particular $Na^\oplus$, $K^\oplus$, $Mg^{2\oplus}$, $Ca^{2\oplus}$, $Al^{3\oplus}$ or an ammonium ion, optionally substituted 1–3 times by $(C_1-C_8)$-alkyl, $(C_1-C_8)$-hydroxyalkyl, $(C_1-C_4)$-alkoxy-$(C_1-C_8)$-alkyl, phenyl, benzyl or $(C_1-C_8)$-alkyl which can be substituted 1 to 3 times by hydroxyl or $(C_1-C_4)$-alkoxy, or a cation of a basic amino acid derivative, $R^7$ is a radical of the formula II, excluding —SO$_2$H, $$—Y—[C—U]_r—D—W \qquad (II)$$

in which

Y is —SO$_2$—

C is a bond or a branched or unbranched aliphatic $(C_1-C_{12})$-alkanediyl radical, or a branched or unbranched $(C_2-C_{12})$-alkenediyl radical, a $(C_2-C_{12})$-alkenynediyl radical or a $(C_2-C_{12})$-alkenynediyl radical, which can contain one or more C—C multiple bonds, U is a bond or hydrogen or a radical from the series of the following hetero atom groups —(CO)NR—, —NR(CO)—, —O—, —SO—, —SO$_2$—, in which R is $(C_1-C_3)$-alkyl, $(C_1-C_8)$-alkanoyl, $(C_7-C_{10})$-aralkanoyl, $(C_6-C_{12})$-aroyl or hydrogen, r is 1 or 2, D is a bond or hydrogen or a branched or unbranched aliphatic $(C_1-C_8)$-alkanediyl radical, or a branched or unbranched $(C_2-C_8)$-alkenediyl radical or $(C_2-C_8)$-alkynediyl radical and W is a bond or hydrogen or a $(C_3–C_{10})$-cycloaliphatic alkyl, alkenyl, alkynyl or alkenynyl radical or a $(C_6–C_{16})$-aryl radical or a 5- or 6-membered heteroaryl radical, where at least one of the variables C or D or W is not a bond and U is only a hetero atom group if C is not a bond or if D and/or W are not a bond and C, D and/or W, if these are not a bond or hydrogen, are preferably substituted for their part by a combination of up to 5 identical or different substituents from the series comprising hydroxyl, halogen, cyano, trifluoromethyl, nitro, carboxyl, $(C_1–C_{12})$-alkyl, $(C_3–C_8)$-cycloalkyl, $(C_6–C_{12})$-aryl, $(C_7–C_{16})$-aralkyl, $(C_3–C_{12})$-alkenyl, $(C_3–C_{12})$-alkynyl, $(C_1–C_{12})$-alkoxy, $(C_1–C_{12})$-alkoxy-$(C_1–C_{12})$-alkyl, $(C_1–C_{12})$-alkoxy-$(C_1–C_{12})$-alkoxy, $(C_6–C_{12})$-aryloxy, $(C_7–C_{16})$-aralkyloxy, $(C_1–C_8)$-hydroxyalkyl, —O—$[CH_2]_x C_f H_{(2f+1-g)} F_g$, —$OCF_2Cl$, —$OCF_2$—CHFCl, $(C_1–C_{12})$-alkylcarbonyl, $(C_3–C_8)$-cycloalkylcarbonyl, $(C_6–C_{12})$-arylcarbonyl, $(C_7–C_{16})$-aralkylcarbonyl, cinnamoyl, $(C_3–C_{12})$-alkenylcarbonyl, $(C_3–C_{12})$-alkynylcarbonyl, $(C_1–C_{12})$-alkoxycarbonyl, $(C_1–C_{12})$-alkoxy-$(C_1–C_{12})$-alkoxycarbonyl, $(C_6–C_{12})$-aryloxycarbonyl, $(C_7–C_{16})$-aralkoxycarbonyl, $(C_3–C_8)$-cycloalkoxycarbonyl, $(C_3–C_{12})$-alkenyloxycarbonyl, $(C_3–C_{12})$-alkynyloxycarbonyl, $(C_1–C_{12})$-alkylcarbonyl, $(C_3–C_8)$-cycloalkylcarbonyl, $(C_6–C_{12})$-arylcarbonyloxy, $(C_7–C_{16})$-aralkylcarbonyloxy, cinnamoyloxy, $(C_3–C_{12})$-alkenylcarbonyloxy, $(C_3–C_{12})$-alkynylcarbonyloxy, carbamoyl, N-$(C_1–C_{12})$-alkylcarbamoyl, N,N-di-$(C_1–C_{12})$-alkylcarbamoyl, N-$(C_3–C_8)$-cycloalkylcarbamoyl, N-$(C_6–C_{16})$-arylcarbamoyl, N-$(C_7–C_{16})$-aralkylcarbamoyl, N-$(C_1–C_{10})$-alkyl-N-$(C_6–C_{16})$-arylcarbamoyl, N-$(C_1–C_{10})$-alkyl-N-$(C_7–C_{16})$-aralkylcarbamoyl, N-($(C_1–C_{10})$-alkoxy-$(C_1–C_{10})$-alkyl)carbamoyl, N-($(C_6–C_{16})$-aryloxy-$(C_1–C_{10})$-alkyl)carbamoyl, N-($(C_7–C_{16})$-aralkyloxy-$(C_1–C_{10})$-alkyl)carbamoyl, N-$(C_1–C_{10})$-alkyl-N-($(C_1–C_{10})$-alkoxy-$(C_1–C_{10})$-alkyl)carbamoyl, N-$(C_1–c_{10})$-alkyl-N-($(C_6–C_{16})$-aryloxy-$(C_1–C_{10})$-alkyl)carbamoyl, N-$(C_1–C_{10})$-alkyl-N-($(C_7–C_{16})$-aralkyloxy-$(C_1–C_{10})$-alkyl)carbamoyl, amino, $(C_1–c_{12})$-alkylamino, di-$(C_1–C_{12})$-alkylamino, $(C_3–C_8)$-cycloalkylamino, $(C_3–C_{12})$-alkenylamino, $(C_3–C_{12})$-alkynylamino, N-$(C_6–C_{12})$-arylamino, N-$(C_7–C_{11})$-aralkylamino, N-$(C_1–C_5)$-alkyl-$(C_7–C_{10})$-aralkylamino, N-$(C_1–C_5)$-alkyl-N-$(C_6–C_{12})$-arylamino, $(C_1–C_{12})$-alkoxyamino, $(C_1–C_{12})$-alkoxy-N-$(C_1–C_{10})$-alkylamino, $(C_1–C_{12})$-alkanoylamino, $(C_3–C_8)$-cycloalkanoylamino, $(C_6–C_{12})$-aroylamino, $(C_7–C_{16})$-aralkanoylamino, $(C_1–C_{12})$-alkanoyl-N-$(C_1–C_{10})$-alkylamino, $(C_3–C_8)$-cycloalkanoyl-N-$(C_1–C_{10})$-alkylamino, $(C_6–C_{12})$-aroyl-N-$(C_1–C_{10})$-alkylamino, $(C_7–C_{11})$-aralkanoyl-N-$(C_1–C_{10})$-alkylamino, $(C_1–C_{12})$-alkanoylamino-$(C_1–C_8)$-alkyl, $(C_3–C_8)$-cycloalkanoylamino-$(C_1–C_8)$-alkyl, $(C_6–C_{16})$-aroylamino-$(C_1–C_8)$-alkyl, $(C_7–C_{16})$-aralkanoylamino-$(C_1–C_8)$-alkyl, amino-$(C_1–C_{10})$-alkyl, N-$(C_1–C_{10})$-alkylamino-$(C_1–C_{10})$-alkyl, N,N-di-$(C_1–C_{10})$-alkylamino-$(C_1–C_{10})$-alkyl, $(C_3–C_8)$-cycloalkylamino-$(C_1–C_{10})$-alkyl, $(C_1–C_{12})$-alkylmercapto, $(C_1–C_{12})$-alkylsulfinyl, $(C_1–C_{12})$-alkylsulfonyl, $(C_6–C_{16})$-arylmercapto, $(C_6–C_{16})$-arylsulfinyl, $(C_6–C_{16})$-arylsulfonyl, $(C_7–C_{16})$-aralkylmercapto, $(C_7–C_{16})$-aralkylsulfinyl, $(C_7–C_{16})$-aralkylsulfonyl, where the radicals which contain an aryl radical can be substituted, for their part, on the aryl by 1, 2, 3, 4 or 5 identical or different substituents from the series comprising hydrogen, hydroxyl, halogen, cyano, trifluoromethyl, nitro, carboxyl, $(C_1–C_{12})$-alkyl, $(C_3–C_8)$-cycloalkyl, $(C_6–C_{12})$-aryl, $(C_7–C_{16})$-aralkyl, $(C_3–C_{12})$-alkenyl, $(C_3–C_{12})$-alkynyl, $(C_1–C_{12})$-alkoxy, $(C_1–C_{12})$-alkoxy$(C_1–C_{12})$-alkyl, $(C_1–C_{12})$-alkoxy-$(C_1–C_{12})$-alkoxy, $(C_6–C_{12})$-aryloxy, $(C_7–C_{16})$-aralkyloxy, $(C_1–C_8)$-hydroxyalkyl, —O—$[CH_2]_x C_f H_{(2f+1-g)} F_g$, —$OCF_2Cl$, —$OCF_2$—CHFCl, $(C_1–C_{12})$-alkylcarbonyl, $(C_3–C_8)$-cycloalkylcarbonyl, $(C_6–C_{12})$-arylcarbonyl, $(C_7–C_{16})$-aralkylcarbonyl, cinnamoyl, $(C_3–C_{12})$-alkenylcarbonyl, $(C_3–C_{12})$-alkynylcarbonyl, $(C_1–C_{12})$-alkoxycarbonyl, $(C_1–C_{12})$-alkoxy-$(C_1–C_{12})$-alkoxycarbonyl, $(C_6–C_{12})$-aryloxycarbonyl, $(C_7–C_{16})$-aralkoxycarbonyl, $(C_3–C_8)$-cycloalkoxy-carbonyl, $(C_3–C_{12})$-alkenyloxycarbonyl, $(C_3–C_{12})$-alkynyloxycarbonyl, $(C_1–C_{12})$-alkylcarbonyloxy, $(C_3–C_8)$-cycloalkylcarbonyloxy, $(C_6–C_{12})$-arylcarbonyloxy, $(C_7–C_{16})$-aralkylcarbonyloxy, cinnamoyloxy, $(C_3–C_{12})$-alkenylcarbonyloxy, $(C_3–C_{12})$-alkynylcarbonyloxy, carbamoyl, N-$(C_1–C_{12})$-alkylcarbamoyl, N,N-di-$(C_1–C_{12})$-alkylcarbamoyl, N-$(C_3–C_8)$-cycloalkylcarbamoyl, N-$(C_6–C_{16})$-arylcarbamoyl, N-$(C_7–C_{16})$-aralkylcarbamoyl, N-$(C_1–C_{10})$-alkyl-N-$(C_6–C_{16})$-aralkylcarbamoyl, N-$(C_1–C_{10})$-alkyl-N-$(C_7–C_{16}$-aralkylcarbamoyl, N-($(C_1–C_{10})$-alkoxy-$(C_1–C_{10})$-alkyl)carbamoyl, N-($(C_6–C_{16})$-aryloxy-$(C_1–C_{10})$-alkyl)carbamoyl, N-($(C_7–C_{16})$-aralkyloxy-$(C_1–C_{10})$-alkyl)carbamoyl, N-$(C_1–C_{10})$-alkyl-N-($(C_1–C_{10})$-alkoxy-$(C_1–C_{10})$-alkyl)carbamoyl, N-$(C_1–C_{10})$-alkyl-N-($(C_6–C_{16})$-aryloxy-$(C_1–C_{10})$-alkyl)carbamoyl, N-$(C_1–C_{10})$-alkyl-N-($(C_7–C_{16})$-aralkyloxy-$(C_1–C_{10})$-alkyl)carbamoyl, amino, $(C_1–C_{12})$-alkylamino, di-$(C_1–C_{12})$-alkylamino, $(C_3–C_8)$-cycloalkylamino, $(C_3–C_{12})$-alkenylamino, $(C_3–C_{12})$-alkynylamino, N-$(C_6–C_{12})$-arylamino, N-$(C_7–C_{11})$-aralkylamino, N-$(C_1–C_5)$-alkyl-$(C_7–C_{10})$-aralkylamino,N-$(C_1–C_5)$-alkyl-N-$(C_6–C_{12})$-arylamino, $(C_1–C_{12})$-alkoxyamino, $(C_1–C_{12})$-alkoxy-N-$(C_1–C_{10})$-alkylamino, $(C_1–C_{12})$-alkanoylamino, $(C_3–C_8)$-cycloalkanoylamino, $(C_6–C_{12})$-aroylamino, $(C_7–C_{16})$-aralkanoylamino, $(C_1–C_{12})$-alkanoyl-N-$(C_1–C_{10})$-alkylamino, $(C_3–C_8)$-cycloalkanoyl-N-$(C_1–C_{10})$-alkylamino, $(C_6–C_{12})$-aroyl-N-$(C_1–C_{10})$-alkylamino, $(C_7–C_{11})$-aralkanoyl-N-$(C_1–C_{10})$-alkylamino, $(C_1–C_{12})$-alkanoylamino-$(C_1–C_8)$-alkyl, $(C_3–C_8)$-cycloalkanoylamino-$(C_1–C_8)$-alkyl, $(C_6–C_{16})$-aroylamino-$(C_1–C_8)$-alkyl, $(C_7–C_{16})$-aralkanoylamino-$(C_1–C_8)$-alkyl, amino-$(C_1–C_{10})$-alkyl, N-$(C_1–C_{10})$-alkylamino-$(C_1–C_{10})$-alkyl, N,N-di-$(C_1–C_{10})$-alkylamino-$(C_1–C_{10})$-alkyl, $(C_3–C_8)$-cycloalkylamino-$(C_1–C_{10})$-alkyl, $(C_1–C_{12})$-alkylmercapto, $(C_1–C_{12})$-alkylsulfinyl, $(C_1–C_{12})$-alkylsulfonyl, $(C_6–C_{16})$-arylmercapto, $(C_6–C_{16})$-arylsulfinyl, $(C_6–C_{16})$-arylsulfonyl, ($C_7$–$C_{16}$)-aralkylmercapto, ($C_7$–$C_{16}$)-aralkylsulfinyl, ($C_7$–$C_{16}$)-aralkylsulfonyl, $R^4$ and $R^5$ independently of one another are hydrogen or A) an unsubstituted or substituted ($C_1$–$C_{12}$)-alkoxy radical, ($C_3$–$C_8$)-cycloalkoxy radical, ($C_6$–$C_{12}$)-aryloxy radical or a ($C_7$–$C_{11}$)-aralkyloxy radical, which is monosubstituted or polysubstituted, preferably monosubstituted or disubstituted, by halogen, trifluoromethyl, ($C_1$–$C_6$)-alkoxy, hydroxyl, ($C_1$–$C_6$)-hydroxyalkyl, B) a branched or unbranched ($C_1$–$C_{12}$)-alkyl radical, C) an unsubstituted or substituted ($C_6$–$C_{12}$)-aryl radical, ($C_7$–$C_{11}$)-aralkyl radical or a hetaryl radical, where the radicals B) and C) are, in particular, monosubstituted or polysubstituted, preferably monosubstituted or disubstituted, by hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_{12}$)-alkoxy, ($C_1$–$C_{12}$)-alkoxy-($C_1$–$C_{12}$-alkyl, ($C_1$–$C_{12}$)-alkoxy-($C_1$–$C_{12}$)-alkoxy, ($C_6$–$C_{12}$)-aryloxy, ($C_7$–$C_{16}$)-aralkyloxy, ($C_1$–$C_8$)-hydroxyalkyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkyloxycarbonyl, ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_3$–$C_{12}$)-alkenylcarbonyloxy, ($C_3$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_3$–$C_{12}$)-alkenyloxycarbonyloxy, ($C_3$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, hydroxy-($C_1$–$C_4$)-alkylcarbamoyl, ($C_1$–$C_6$)-alkoxy-($C_1$–$C_6$)-alkylcarbamoyl, a carbamoyl radical of the formula III in which P is a polypeptide bonded via one of its amino groups or an amino acid or amino acid derivative bonded via its amino group, where the radical $NR^4R^5$ is the radical of an α-amino acid or an α-amino acid derivative, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{16}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkoxy-($C_1$–$C_{10}$)-alkyl)carbamoyloxy, N-(($C_6$–$C_{16}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{16}$)-aryloxy-($C_1$–$C_{10}$)-alkyl)-carbamoyloxy, N-($C_1$–$C_{10}$)-alkyl-N-(($C_7$–$C_{16}$)-aralkyloxy-($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-alkylamino, N-alkylarylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, a radical of the formula IV $$\text{—O—R}^8 \qquad \text{(IV)}$$

in which $R^8$ is an amino acid bonded via its acyl radical, its N-protected derivative or an alcohol protective group, where the radicals which contain an aryl radical can be substituted, for their part, on the aryl by 1, 2, 3, 4 or 5 identical or different substituents from the series comprising hydroxyl, halogen, cyano, trifluoromethyl, nitro, ($C_1$–$C_{12}$)-alkyl, ($C_3$–$C_8$)-cycloalkyl, ($C_1$–$C_{12}$)-alkoxy, ($C_1$–$C_{12}$)-alkoxy-($C_1$–$C_{12}$)-alkyl, ($C_6$–$C_{12}$)-aryloxy, ($C_7$–$C_{16}$)-aralkyloxy, ($C_1$–$C_8$)-hydroxyalkyl, —O—[$CH_2$]$_x C_f H_{(2f+1-g)}$, —$OCF_2Cl$, —$OCF_2$—$CHFCl$, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkylcarbonyl, ($C_3$–$C_8$)-cycloalkoxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy- ($C_1$–$C_{10}$)-alkyl)-carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, and n is 0, f is 1 to 5, g 0.1 to (2f+1) and x is 0 or 1.

Particularly preferred compounds of the formula I are those in which

X is a single bond or —CO—

$R^1$, $R^2$ and $R^3$ are identical or different and are hydrogen or ($C_1$–$C_3$)-alkyl, ($C_1$–$C_3$)-alkoxy, hydroxyl, fluorine or chlorine, $R^6$ is hydrogen or a 1- or 2-valent physiologically utilizable cation, in particular $Na^\oplus$, $K^\oplus$, $Mg^{2\oplus}$ or $Ca^{2\oplus}$ or an ammonium ion, $R^7$ is a radical of the formula II, excluding —$SO_2H$, $$-Y-[C-U]_r-D-W \qquad (II)$$

in which

Y is —$SO_2$—,

C is a bond or a ($C_1$–$C_6$)-alkanediyl radical,

U is a bond or hydrogen or —O—, r is 1,

D is a bond or hydrogen or an unbranched aliphatic ($C_1$–$C_8$)-alkanediyl radical, and W is a bond or hydrogen, a ($C_6$–$C_{12}$)-aryl radical or a 5- or 6-membered heteroaryl radical, where at least one of the variables C or D or W is not a bond and U is only a hetero atom group if C is not a bond or if D and/or W are not a bond and C, D and/or W, if these are not a bond or hydrogen, are preferably substituted for their part by up to 3 identical or different substituents from the series comprising hydroxyl, halogen, cyano, trifluoromethyl, nitro, carboxyl, ($C_1$–$C_8$)-alkyl, ($C_3$–$C_8$)-cycloalkyl, ($C_6$–$C_{12}$)-aryl, ($C_7$–$C_{16}$)-aralkyl, ($C_3$–$C_8$)-alkenyl, ($C_3$–$C_8$)-alkynyl, ($C_1$–$C_8$)-alkoxy, ($C_1$–$C_8$)-alkoxy-($C_1$–$C_8$)-alkyl, ($C_6$–$C_{12}$)-aryloxy, ($C_7$–$C_{16}$)-aralkyloxy, ($C_1$–$C_8$)-hydroxyalkyl, —O—$[CH_2]_xC_fH_{(2f+1-g)}F_g$, ($C_1$–$C_8$)-alkoxycarbonyl, ($C_6$–$C_{12}$)-aryloxycarbonyl, ($C_7$–$C_{14}$)-aralkoxycarbonyl, ($C_3$–$C_8$)-cycloalkoxycarbonyl, ($C_1$–$C_8$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, amino, ($C_1$–$C_8$)-alkylamino, di-($C_1$–$C_8$)-alkylamino, ($C_3$–$C_8$)-cycloalkylamino, N-($C_6$–$C_{12}$)-arylamino, N-($C_7$–$C_{11}$)-aralkylamino, N-($C_7$–$C_{11}$)-alkyl-N-($C_7$–$C_{11}$)-aralkylamino, ($C_1$–$C_{10}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{10}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{10}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_6$)-alkyl, ($C_3$–$C_8$)-cycloalkanoylamino-($C_1$–$C_8$)-alkyl, ($C_6$–$C_{16}$)-aroylamino-($C_1$–$C_6$)-alkyl, ($C_7$–$C_{16}$)-aralkanoylamino-($C_1$–$C_6$)-alkyl, ($C_1$–$C_8$)-alkylmercapto, ($C_1$–$C_8$)-alkylsulfonyl, ($C_6$–$C_{12}$)-arylmercapto, ($C_6$–$C_{12}$)-arylsulfinyl, ($C_6$–$C_{12}$)-arylsulfonyl, ($C_7$–$C_{14}$)-aralkylmercapto, ($C_7$–$C_{14}$)-aralkylsulfinyl, ($C_7$–$C_{14}$)-aralkylsulfonyl, where the radicals which contain an aryl radical can for their part be substituted on the aryl by 1, 2, 3, 4 or 5 identical or different substituents from the series comprising hydrogen, hydroxyl, halogen, cyano, trifluoromethyl, nitro, carboxyl, ($C_1$–$C_8$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_8$)-alkoxy, ($C_1$–$C_6$)-alkoxy-($C_1$–$C_6$)-alkyl, ($C_6$–$C_{12}$)-aryloxy, ($C_7$–$C_{16}$)-aralkyloxy, —O—$[CH_2]_xC_fH_{(2f+1-g)}F_g$, ($C_1$–$C_{12}$)-alkoxycarbony, ($C_3$–$C_8$)-cycloalkoxycarbonyl, ($C_1$–$C_{12}$)-alkylcarbonyloxy, ($C_3$–$C_8$)-cycloalkylcarbonyloxy, carbamoyl, N-($C_1$–$C_8$)-alkylcarbamoyl, N,N-di-($C_1$–$C_8$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_8$)-alkyl-N-($C_6$–$C_{16}$)-arylcarbamoyl, N-($C_1$–$C_8$)-alkyl-N-($C_7$–$C_{16}$)-aralkylcarbamoyl, N-(($C_1$–$C_6$)-alkoxy-($C_1$–$C_{16}$)-alkyl)carbamoyl, N-(($C_7$–$C_{16}$)-aralkyloxy-($C_1$–$C_{C6}$)-alkyl)carbamoyl, N-($C_1$–$C_8$)-alkyl-N-(($C_1$–$C_6$)-alkoxy-($C_1$–$C_6$)-alkyl)carbamoyl, N-($C_1$–$C_8$)-alkyl-N-(($C_6$–$C_{16}$)-aryloxy-($C_1$–$C_6$)-alkyl)carbamoyl, N-($C_1$–$C_8$)-alkyl-N-(($C_7$–$C_{16}$)-aralkyloxy-($C_1$–$C_6$)-alkyl)carbamoyl, N-($C_1$–$C_8$)-alkyl-N-(($C_7$–$C_{16}$)-aralkyloxy-($C_1$–$C_6$)-alkyl)carbamoyl, amino, ($C_1$–$C_6$)-alkylamino, di-($C_1$–$C_6$)-alkylamino, ($C_3$–$C_8$)-cycloalkylamino, N-($C_6$–$C_{12}$)-arylamino, N-($C_7$–$C_{11}$)-aralkylamino, N-($C_1$–$C_3$)-alkyl-($C_7$–$C_{11}$)-aralkylamino, N-($C_1$–$C_3$)-alkyl-($C_6$–$C_{12}$)-arylamino, ($C_1$–$C_8$)-alkoxyamino, ($C_1$–$C_8$)-alkanoylamino, ($C_3$–$C_8$)-cycloalkanoylamino, ($C_6$–$C_{12}$)-aroylamino, ($C_7$–$C_{12}$)-aralkanoylamino, $(C_1-C_8)$-alkanoyl-N-$(C_1-C_6)$-alkylamino, $(C_3-C_8)$-cycloalkanoyl-N-$(C_1-C_6)$-alkylamino, $(C_6-C_{12})$-aroyl-N-$(C_1-C_{10})$-alkylamino, $(C_7-C_{11})$-aralkanoyl-N-$(C_1-C_6)$-alkylamino,
$(C_1-C_8)$-alkanoylamino-$(C_1-C_4)$-alkyl, $(C_3-C_8)$-cycloalkanoylamino-$(C_1-C_4)$-alkyl, $(C_6-C_{12})$-aroylamino-$(C_1-C_4)$-alkyl, $(C_7-C_{12})$-aralkanoylamino-$(C_1-C_4)$-alkyl, $R^4$ is hydrogen or $(C_1-C_6)$-alkyl and $R^5$ is A) an unsubstituted $(C_1-C_6)$-alkoxy radical, $(C_3-C_8)$-cycloalkoxy radical, phenoxy radical or benzyloxy radical or B) a branched or unbranched $(C_1-C_8)$-alkyl radical, C) a $(C_6-C_{12})$-aryl or $(C_7-C_{11})$-aralkyl radical, preferably phenyl, benzyl or phenethyl, where the radicals B) and C) are unsubstituted or monosubstituted by hydroxyl, halogen, cyano, phenyl, benzyl, carboxyl, $(C_1-C_6)$-alkoxy, $(C_6-C_{12})$-aryloxy, $(C_7-C_{11})$-aralkyloxy, $(C_1-C_{12})$-alkoxycarbonyl, $(C_1-C_{12})$-alkoxy-$(C_1-C_{12})$-alkoxycarbonyl, $(C_6-C_{12})$-aroxycarbonyl, $(C_7-C_{16})$-aralkoxycarbonyl, $(C_3-C_8)$-cycloalkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $C_7-C_{16}$-aralkylcarbonyloxy, $(C_3-C_8)$-cycloalkylcarbonyloxy, carbamoyl, N-$(C_1-C_8)$-alkylcarbamoyl, N,N-di-$(C_1-C_8)$-alkylcarbamoyl, N-$(C_3-C_8)$-cycloalkylcarbamoyl, N-$(C_6-C_{11})$-arylcarbamoyl, N-$(C_7-C_{16})$-aralkylcarbamoyl, N-$(C_1-C_6)$-alkyl-N-$(C_6-C_{10})$-arylcarbamoyl, N-$(C_1-C_6)$-alkyl-N-$(C_7-C_{11})$-aralkylcarbamoyl, N-$((C_1-C_6)$-alkoxy-$(C_1-C_6)$-alkyl)carbamoyl, N-$((C_6-C_{10})$-aryloxy-$(C_1-C_6)$-alkyl)carbamoyl, N-$((C_7-C_{11})$-aralkyloxy-$(C_1-C_6)$alkyl)-carbamoyl, N-$(C_1-C_6)$-alkyl-N-$((C_1-C_6)$-alkoxy-$(C_1-C_{10})$-alkyl)carbamoyl, N-$(C_1-C_6)$-alkyl-N-$((C_6-C_{16})$-aryloxy-$(C_1-C_{10})$-alkyl)carbamoyl, N-$(C_1-C_6)$-alkyl-N-$((C_7-C_{16})$-aralkyloxy-$(C_1-C_{10})$-alkyl)carbamoyl, a carbamoyl radical of the formula III $$-CO-P \qquad (III)$$

in which

P is a tri- or dipeptide bonded via its N-terminal amino group, or an amino acid derivative bonded via its amino group, preferably an L-amino acid derivative, in particular an L-alanine or L-glycine amino acid derivative, and the radical $NR^4R^5$ is the radical of an L-α-amino acid, carbamoyloxy, N-$(C_3-C_8)$-alkylcarbamoyloxy, N,N-di-$(C_1-C_8)$-alkylcarbamoyloxy, N-$(C_3-C_8)$-cycloalkylcarbamoyloxy, N-$(C_1-C_{(C1}-C_8)$-alkanoylamino, $(C_1-C_{12})$-alkanoyl-N-$(C_1-C_6)$-alkaylamino, a radical of the formula IV $$-O-R^8 \qquad (IV)$$

in which $R^8$ is an amino acid bonded via its acyl radical or an N-protected derivative thereof, where the aryl and aralkyl radicals in the aromatic moiety present in the above substituents are in particular substituted by 1 or 2 identical or different substituents from the series comprising $(C_1-C_3)$-alkyl, hydroxyl, $(C_1-C_4)$-alkoxy, $(C_1-C_4)$-alkoxycarbonyl, $(C_1-C_5)$-alkylcarbonyloxy, trifluoromethyl, chlorine and fluorine and n is 0, f is 1 to 5, g is 0.1 to (2f+1) and x is 0 or 1.

Very particularly preferred compounds of the formula I are those in which

X is a single bond or —CO—, $R^1$, $R^2$ and $R^3$ are hydrogen, $^6$ is hydrogen or a 1- or 2-valent physiologically utilizable cation, in particular $Na^\oplus$, $K^\oplus$, $Mg^{2\oplus}$ or $Ca^{2\oplus}$ or an ammonium ion, in particular $H_3N^\oplus C(CH_2OH)_3$, $R^7$ is a radical of the formula II, excluding —$SO_2H$, $$-Y-[C-U]_r-D-W \qquad (II)$$

in which

Y is —$SO_2$—,

C is a bond or $(C_1-C_4)$-alkanediyl,

U is a bond, hydrogen or —O—, r is 1,

D is a bond, hydrogen or $(C_1-C_4)$-alkanediyl,

W is a bond, hydrogen or a phenyl radical, where at least one of the variables C or D or W is not a bond and U is only a hetero atom group if C is not a bond or if D and/or W are not a bond and C, D and/or W are substituted by hydrogen, fluorine, chlorine, $(C_1-C_6)$-alkyl, $(C_3-C_8)$-cycloalkyl, $(C_6-C_{12})$-aryl, $(C_7-C_{16})$-aralkyl, $(C_3-C_{12})$-alkenyl, phenyl, $(C_1-C_6)$-alkoxy, phenoxy, —O—$[CH_2]_xC_fH_{(2f+1-g)}F_g$, carbamoyl, N-$(C_1-C_{10})$-alkylcarbamoyl, N,N-di-$(C_1-C_8)$-alkylcarbamoyl, N-$(C_3-C_8)$-cycloalkylcarbamoyl, N-phenylcarbamoyl, N-$(C_7-C_{11})$-phenylalkylcarbamoyl, N-$(C_1-C_8)$-alkyl-N-$(C_6-C_{16})$-phenylcarbamoyl, N-$(C_1-C_8)$-alkyl-N-$(C_7-C_{11})$-phenylalkylcarbamoyl, N-$((C_1-C_{10})$-alkoxy-$(C_1-C_8)$-alkyl)carbamoyl, N-phenoxy-$(C_1-C_8)$-alkyl)carbamoyl, N-$((C_7-C_{16})$-phenylalkyloxy-$(C_1-C_8)$-alkyl)carbamoyl, N-$(C_1-C_8)$-alkyl-N-$((C_1-C_6)$-alkoxy-$(C_1-C_8)$-alkyl)carbamoyl, N-$(C_1-C_8)$-alkyl-N-$((C_6-C_{12})$-phenoxy-$(C_1-C_8)$-alkyl)carbamoyl, N-$(C_1-C_8)$-alkyl-N-$((C_7-C_{16})$-phenylalkyloxy-$(C_1-C_8)$-alkyl)carbamoyl, $(C_1-C_8)$-alkanoylamino, $(C_3-C_8)$-cycloalkanoylamino, $(C_6-C_{12})$-phenylamino, $(C_7-C_{11})$-phenylalkanoylamino, $(C_1-C_8)$-alkanoyl-N-$(C_1-C_{10})$-alkylamino, $(C_3-C_8)$-cycloalkanoyl-N-$(C_1-C_6)$-alkylamino, benzoyl-N-$(C_1-C_{10})$-alkylamino, $(C_7-C_{11})$-phenylalkanoyl-N-$(C_1-C_6)$-alkylamino, $(C_1-C_{10})$-alkanoylamino-$(C_1-C_8)$-alkyl, $(C_3-C_8)$-cycloalkanoylamino-$(C_1-C_8)$-alkyl, phenylamino-$(C_1-C_8)$-alkyl, $(C_7-C_{11})$-phenylalkanoylamino-$(C_1-C_8)$-alkyl, where the radicals which contain an aryl radical can for their part be substituted on the aryl by 1, 2, 3, 4 or 5 identical or different substituents from the series comprising hydroxyl, carboxyl, $(C_1-C_4)$-alkoxy, phenoxy and benzyloxy, $(C_1-C_9)$-alkoxycarbonyl, phenoxycarbonyl, $(C_7-C_{11})$-phenylalkoxycarbonyl, $(C_3-C_8)$-cycloalkoxycarbonyl, ($C_1$–$C_{12}$)-alkylcarbonyloxy, ($C_3$–$C_8$)-cycloalkylcarbonyloxy, benzoyloxy, ($C_7$–$C_{11}$)-phenalkylcarbonyloxy, ($C_1$–$C_8$)-alkoxycarbonyloxy, ($C_6$–$C_{12}$)-phenoxycarbonyloxy, ($C_7$–$C_{11}$)-phenalkyloxycarbonyloxy, ($C_3$–$C_8$)-cycloalkoxycarbonyloxy, carbamoyl, N-($C_1$–$C_6$)-alkylcarbamoyl, N,N-di-($C_1$–$C_6$)-alkylcarbamoyl, N-($C_3$–$C_8$)-cycloalkylcarbamoyl, N-phenylcarbamoyl, N-($C_7$–$C_{11}$)-phenalkylcarbamoyl, hydroxy-($C_1$–$C_4$)-alkylcarbamoyl, acyloxy-($C_1$–$C_4$)-alkylcarbamoyl, carbamoyloxy, N-($C_1$–$C_6$)-alkylcarbamoyloxy, N,N-di-($C_1$–$C_6$)-alkylcarbamoyloxy, N-($C_3$–$C_8$)-cycloalkylcarbamoyl, $R^4$ is hydrogen, $R^5$ is an unbranched ($C_1$–$C_4$)-alkyl radical which is substituted by a radical from the series comprising hydroxyl, carboxyl, ($C_1$–$C_4$)-alkoxy, phenoxy, benzyloxy, ($C_1$–$C_9$)-alkoxycarbonyl, phenoxycarbonyl, ($C_7$–$C_{11}$)-phenylalkyloxycarbonyl, ($C_3$–$C_8$)-cycloalkoxycarbonyl, ($C_1$–$C_{12}$)-alkylcarbonyloxy, ($C_3$–$C_8$)-cycloalkylcarbonyloxy, benzoyloxy, ($C_7$–$C_{11}$)-phenylalkylcarbonyloxy, ($C_1$–$C_8$)-alkoxycarbonyloxy, phenoxycarbonyloxy, ($C_7$–$C_{11}$)-phenylalkylcarbonyloxy, ($C_3$–$C_8$)-cycloalkoxycarbonyloxy, carbamoyl, N-($C_1$–$C_6$)-alkylcarbamoyl, N,N-di-($C_1$–$C_6$)-alkylcarbamoyl, N-($C_3$–$C_8$)-cycloalkylcarbamoyl, N-phenylcarbamoyl, N-($C_7$–$C_{11}$)-phenalkylcarbamoyl, hydroxy-($C_1$–$C_4$)-alkylcarbamoyl, acyloxy-($C_1$–$C_4$)-alkylcarbamoyl, ($C_1$–$C_6$)-alkoxy-($C_1$–$C_6$)-alkylcarbamoyl, carbamoyloxy, N-($C_1$–$C_6$)-alkylcarbamoyloxy, N,N-di-($C_1$–$C_6$)-alkylcarbamoyloxy, N-($C_3$–$C_8$)-cycloalkylcarbamoyloxy, or a radical of the formula III

—CO—P (III)

in which

P is a di- or tripeptide bonded via its terminal amino group or an amino acid derivative bonded via its amino group, where L-glycine is preferably at the start of the peptide chain, where the aryl and aralkyl radicals present in the above substituents are in particular substituted by 1 or 2 identical or different substituents from the series comprising ($C_1$–$C_6$-alkyl, hydroxyl, ($C_1$–$C_4$)-alkoxy, ($C_1$–$C_4$)-alkoxycarbonyl, ($C_1$–$C_5$)-alkylcarbonyloxy, trifluoromethyl, chlorine and fluorine, and n is 0, f 1 to 5, g 0.1 to (2f+1) and x is 0 or 1.

The invention furthermore relates to the use of compounds of the formula I and the physiologically tolerable salts for the production of a pharmaceutical against fibrotic diseases, in particular of the liver.

Finally, the invention relates to the compounds of the formula I for use as pharmaceuticals.

The invention relates in particular to the compounds of the formula I for use as fibrosuppressants.

The invention furthermore relates to a process for the preparation of compounds of the formula I.

Compounds of the formula I in which X is a single bond were prepared by i) reacting the pyridine-2-carboxylic acid ester derivatives of the formula 3 or the pyridine-2-carboxylic acid derivatives of the formula 4 with the amines of the formula 5, or ii) reacting the pyridine-2-carboxamide derivatives of the formula 6 with the sulfonic acid derivatives of the formula 2, cf. Scheme 1.

Scheme 1 illustrates the preparation of compounds of the formula Ia or Ib, in which X is a single bond:

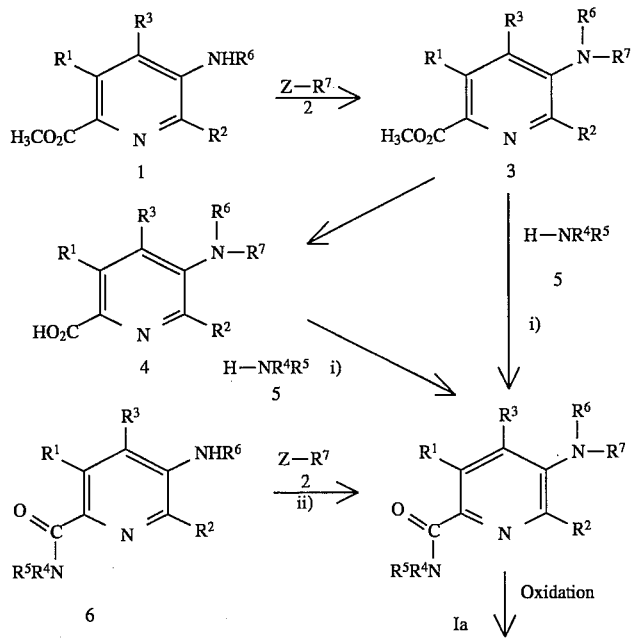

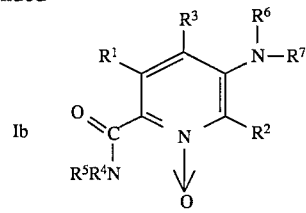

5-Aminopyridine-2-carboxylates of the formula 1 are reacted with sulfonic acid derivatives or carboxylic acid derivatives of the formula 2, in which Z is a hydroxy group or a leaving group which can be detached nucleophilically and is in particular F, Cl, Br, I or tosylate. This reaction is carried out in an aprotic organic solvent or a solvent mixture. The following solvents may be mentioned in particular: dichloromethane, tetrachloromethane, butyl acetate, ethyl acetate, toluene, tetrahydrofuran, dimethoxyethane, 1,4-dioxane, acetonitrile, N,N-dimethylformamide, N,N-dimethylacetamide, dimethyl sulfoxide, nitromethane and/or pyridine, if appropriate with the addition of an acid binder, such as ammonia, triethylamine or tributylamine, at a reaction temperature from 0° to 180° C., preferably from 0° to 180° C. If Z is a hydroxy group, the condensation methods known from peptide chemistry are suitable.

The compounds of the formula Ia are finally either obtained by hydrolyzing the compounds of the formula 3 to give the pyridine-2-carboxylic acids 4 and reacting these with the appropriate amines 5 according to the known methods of peptide chemistry or by reacting the compounds of the formula 3 directly with the amines 5. If desired, oxidation to give the pyridine-N-oxides of the formula Ib is additionally carried out immediately afterwards.

A general procedure for this oxidation method is also described, for example, in "E. Klinsberg, Pyridine and its Derivatives, Interscience Publishers, New York, 1961, Part 2, p. 93".

The oxidation with hydrogen peroxide is described, for example, in "E. Ochiai, J. Org. Chem. 18, 534 (1953)".

The process conditions can be taken in detail from German Patent Application P 38 26 471.4, 38 28 140.6, 39 24 093.2, 40 01 002.3 and DE-A-3,703,959, 3,703,962 and 3,703,963.

The preparation of the compounds of the formula 1 is described by N. Finch et al., J. Med. Chem. (1978), Vol. 21, page 1269 and Schneider and Harris, J. Org. Chem. (1984), Vol. 49, page 3683.

The reaction sequence according to Scheme 1 described above for the preparation of compounds of the formulae Ia and Ib having a sulfonamide group in the 5-position can also be used for the preparation of those compounds which have this sulfonamide group in the 4-position. The reaction is then started with compounds of the formula 1':

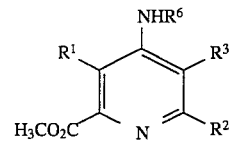

Compounds of the formula I in which X is a bond, Y is $SO_2$, $R^4$ is hydrogen and $R^5$ is a hydroxyalkyl radical, an alkoxyalkyl radical or a derivative thereof, were prepared from the correspondingly substituted sulfonic acid derivatives of the formula 2, and methyl 4-(or 5-)aminopyridine-2'-carboxylates of the formula 1 and subsequent aminolysis of the compounds of the formula 3 (Scheme 1) with the appropriate amines.

Compounds of the formula I in which

X is —CO— and

Y is $SO_2$, were prepared by i) reacting the pyridine-2-carboxylic acid derivatives or the corresponding esters of the formula 11 with the amines of the formula 5, or ii) reacting the pyridine-5-carboxylic acid derivatives of the formula 12 with the sulfonamide derivatives of the formula 9, or iii) reacting the pyridine-5-carboxamide derivatives of the formula 13 with the sulfonic acid derivatives of the formula 2, cf. Scheme 2, where the compounds of the formulae 12 and 13 were for their part prepared from the compounds of the formula 7 by the known methods.

Scheme 2 illustrates the preparation of compounds of the formula Ia or Ib, in which X is —CO— and Y is $SO_2$:

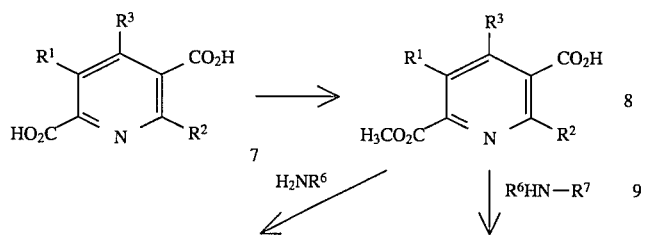

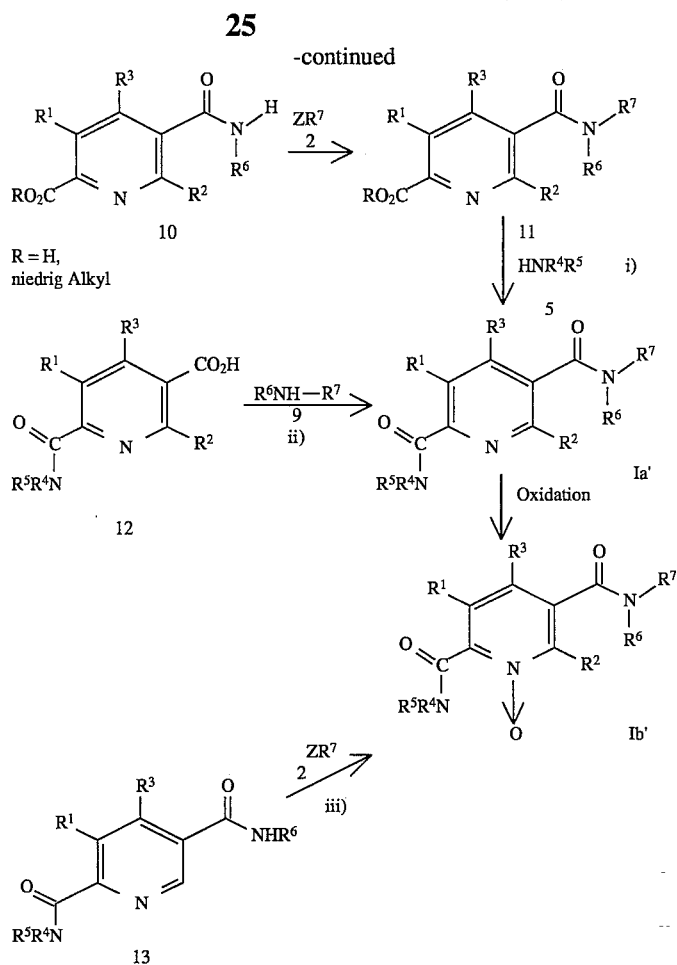

According to CA: Vol 68, 1968, 68840 h, the pyridine-2-carboxylic acid ester 5-carboxylates of the formula 8 can be prepared from the substituted pyridine-2,5-dicarboxylic acids of the formula 7 under esterification conditions. Suitable conditions are, for example, esterification with methanol in the presence of sulfuric acid, the reaction time being selected such that complete esterification to give the diester product only takes place to an insignificant extent, or the diester products can be removed as by-products.

The compounds of the formula 11 are prepared from the compounds of the formula 8 and the sulfonamide derivatives of the formula 9 ($Y=SO_2$), it possibly being expedient to activate both reactants with auxiliary reagents (Houben-Weyl: Methoden der Organischen Chemie (Methods of Organic Chemistry), Volume IX, Chapter 19, pages 636–637).

By way of reagents for carboxylic acid activation, the substances known to the person skilled in the art, such as thionyl chloride, oxalyl chloride, pivaloyl chloride or chloroformic acid ester derivatives, can be used. It is not always necessary to isolate these activated derivatives of the compounds of the formula 8. It is usually expedient to react them after preparation in situ or as a crude product with the sulfonamide derivatives of the formula 9.

Expediently, the compounds of the formula 9 are first caused to react with an inorganic or organic base, such as, for example, the hydroxide, carbonate, alkoxide, hydride or amide of sodium or potassium, ammonia, triethylamine, tributylamine or pyridine at –20° to +150° C., preferably at 0°–80° C. and this reaction mixture is reacted with a compound of the formula 8 or its activated form. The reaction is carried out in an inert solvent, such as, for example, methylene chloride, methanol, ethanol, acetone, ethyl acetate, toluene, tetrahydrofuran, acetonitrile, N,N-dimethylformamide, N,N-dimethylacetamide, nitromethane, dimethyl sulfoxide or mixtures of these solvents. Alternatively, the esters of the formula 11 can be prepared with the aid of the customary condensation reagents (such as, for example, N,N'-dicyclohexylcarbodiimide/4-N,N-dimethylaminopyridine).

The reaction of the pyridine-2-carboxylic acid esters 11 with amines $HNR^4R^5$ leads to the compounds of the formula Ia' according to the invention.

Alternatively, for the preparation of the compounds of the formula Ia', the compounds 11 (R=lower alkyl) can be hydrolyzed to give the pyridine-2-carboxylic acid derivatives 11 (R=H) and these can then be coupled with the amines $HNR^4R^5$ by the customary methods of peptide chemistry to give the compounds of the formula Ia' according to the invention.

The further reaction of the pyridine-N-oxides of the formula Ib' is already illustrated in Scheme 1 (reaction of compound Ia to give compound Ib).

The reaction sequence according to Scheme 2 described above for the preparation of compounds of the formulae Ia' or Ib' having a carbonylsulfonamide group in the 5-position can also be used for the preparation of those compounds which have a carbonylsulfonamide group in the 4-position. The reaction is then started with compounds of the formula 7':

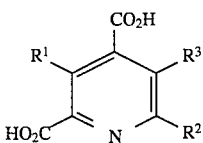

7'

Compounds of the formula I, in which X is CO, Y is $SO_2$, $R^4$ is hydrogen and $R^5$ is a hydroxyalkyl radical, an alkoxyalkyl radical or a derivative thereof, were prepared from the correspondingly substituted sulfonamides of the formula 9 and 2-methoxycarbonylpyridine-4-(or 5)-carboxylic acid and subsequent aminolysis of the compounds of the formula 11 (R=lower alkyl; Scheme 2) with the corresponding amines.

For the preparation of the compounds of the formula I in which $NR^4R^5$ is a glycyl residue, the compounds of the formulae 3 and 11 (R=lower alkyl) were hydrolyzed to give the pyridine-2-carboxylic acid derivatives of the formulae 4 and 11 (R=H) and these were condensed with the corresponding glycine derivatives.

The free glycyl amides, in which $NR^4R^5$ is $NHCH_2CO_2H$, were obtained by hydrolysis of the (glycyl ester) amides or by catalytic hydrogenation of the glycyl benzyl esters.

For the preparation of compounds of the formula I (Ia, Ib, Ia', Ib') according to the Schemes 1 and 2, compounds are employed in which $R^6$ is hydrogen. Salt formation, after which $R^6$ is a physiologically utilizable cation, is preferably carried out subsequently. Suitable salt-forming agents are preferably N-alkylamines, (hydroxyalkyl)amines and (alkoxyalkyl)amines, such as, for example, 2-ethanolamine, 3-propanolamine, 2-methoxyethylamine, 2-ethoxyethylamine and α,α,α-tris(hydroxymethyl)methylamine (=tris buffer, tromethamine) or alternatively basic amino acids, such as, for example, histidine, arginine and lysine.

The compounds of the formula I according to the invention have useful pharmacological properties and in particular exhibit antifibrotic activity.

The antifibrotic action can be determined in the carbon tetrachloride-induced liver fibrosis model. For this purpose, rats are treated twice weekly with $CCl_4$ (1 ml/kg)—dissolved in olive oil. The test substance is administered daily, if necessary even twice daily, orally or intraperitoneally—dissolved in a suitable, tolerable solvent. The extent of liver fibrosis is determined histologically and the content of collagen in the liver is analyzed by hydroxyproline determination—as described by Kivirikko et al. (Anal. Biochem. 19, 249 et seq. (1967)). The fibrogenesis activity can be determined by radioimmunological determination of collagen fragments and procollagen peptides in the serum. The compounds according to the invention are active in this model at a concentration of 1–100 mg/kg.

The fibrogenesis activity can be determined by radioimmunological determination of the N-terminal propeptide of collagen type III or of the N- or C-terminal cross-linking domain of collagen type IV (7s collagen or type IV collagen $NC_1$) in the serum.

For this purpose, the hydroxyproline, procollagen III peptide, 7s collagen and type IV collagen NC concentrations were measured in the liver of a) untreated rats (control)

b) rats to whom carbon tetrachloride was administered ($CCl_4$ control)

c) rats to whom first $CCl_4$ and then a compound according to the invention were administered (this test method is described by Rouiller, C., experimental toxic injury of the liver; in The Liver, C. Rouiller, Vol. 2, 5. 335–476, New York, Academic Press, 1964).

The compounds of the formula I can be used as medicaments in the form of pharmaceutical preparations which contain them, if appropriate together with tolerable pharmaceutical excipients. The compounds can be used as medicines, for example in the form of pharmaceutical preparations which contain these compounds in a mixture with a pharmaceutical, organic or inorganic excipient suitable for enteral, percutaneous or parenteral administration, such as, for example, water, gum arabic, gelatin, lactose, starch, magnesium stearate, talc, vegetable oils, polyalkylene glycols, petroleum jelly etc.

They can be administered orally for this purpose in doses of 0.1–25 mg/kg/day, preferably 1–5 mg/kg/day or parenterally in doses of 0.01–5 mg/kg/day, preferably 0.01–2.5 mg/kg/day, in particular 0.5–1.0 mg/kg/day. The dosage can also be increased in severe cases. In many cases, however, lower doses are also adequate. These data relate to an adult having a weight of about 75 kg.

The invention furthermore comprises the use of the compounds according to the invention in the production of pharmaceuticals which are employed for the treatment and prophylaxis of the abovementioned metabolic disorders.

The invention furthermore relates to pharmaceuticals which contain one or more compounds of the formula I according to the invention and/or their physiologically tolerable salts.

The pharmaceuticals are prepared by processes which are known per se and which are familiar to the person skilled in the art. Pharmaceuticals employed are the pharmacologically active compounds according to the invention (=active compound) either as such or preferably in combination with suitable pharmaceutical auxiliaries or excipients in the form of tablets, coated tablets, capsules, suppositories, emulsions, suspensions or solutions, the active compound content being up to about 95%, advantageously between 10 and 75%.

Suitable auxiliaries or excipients for the desired pharmaceutical formulation are, for example, apart from solvents, gel-forming agents, suppository bases, tablet auxiliaries and other active compound excipients, also antioxidants, dispersants, emulsifiers, antifoams, flavor correctants, preservatives, solubilizers or colorants.

The following examples are intended to illustrate the invention.

EXAMPLE 1

N-(2-Hydroxyethyl)-5-[((4-methoxyphenylsulfonyl) amino)-carbonyl]pyridine-2-carboxamide a) 2-Methoxycarbonylpyridine-5-carbonyl chloride 14.5 g (80 mmol) of 2-methoxycarbonylpyridine-5-carboxylic acid are treated with 6.48 ml of thionyl chloride and 2 ml of anhydrous N,N-dimethylformamide in 200 ml of anhydrous toluene. The mixture is heated at 70° C. for 3 h with stirring. It is then concentrated in vacuo and the residue is dissolved in 150 ml of tetrahydrofuran.

b) Methyl 5-[(4-methoxyphenylsulfonyl)amino)carbonyl] -pyridine-2-carboxylate 19.75 g (176 mmol) of potassium tert-butoxide are added at 0° C. to 16.45 g (88 mmol) of 4-methoxybenzenesulfonamide in 200 ml of tetrahydrofuran. After the mixture has been stirred at room temperature for 3 h, the solution from Example 1) is added at 0°–5° C. The mixture is stirred for 3 h while warming to room temperature, 300 ml of ethyl acetate are added, the mixture is extracted twice with aqueous $NaHCO_3$ solution, the aqueous phase is acidified with concentrated aqueous hydrochloric acid and extracted 3 times with dichloromethane, the extract is dried and concentrated, the residue is crystallized from methanol and 9.9 g of colorless, crystalline product are obtained, M.p. 197°–199° C.

c) 2.1 g (6 mmol) of the above compound are dissolved in 10 ml of ethanolamine and the solution is stirred at 50° C. for 5 h. 40 ml of water are added, the mixture is acidified with conc. HCl while cooling in ice (5°–10° C.), and the precipitated solid is filtered off with suction and washed several times with water. 1.96 g of the title comound are obtained in the form of colorless crystals, M.p. 221°–223° C.

EXAMPLE 2

N-Methoxycarbonylmethyl-5-[((4-methoxyphenylsulfonyl)amino)carbonyl]pyridine-2-carboxamide a) 5-[((Methoxyphenylsulfonyl)amino)carbonyl]pyridine-2-carboxylic acid 3.0 g (8.6 mmol) of the compound from Example 1b) are dissolved in 100 ml of methanol and the solution is treated at 0°–5° C. with 17.2 ml (17.2 mmol) of 1N NaOH. After the mixture has been stirred at room temperature for 4 h, it is concentrated in vacuo, the residue is taken up in water and 17.2 ml (17.2 mmol) of 1N HCl are added at 0°–5° C., the solid is filtered off with suction and washed several times with water, and 2.58 g of the above compound are obtained, M.p. 234°–236° C.

b) 1.8 g (5.94 mmol) of triethylamine are added at 0° C. to 1.81 g (5.4 mmol) of the above compound in 25 ml of anhydrous tetrahydrofuran, the mixture is stirred at this temperature for 20 min, 0.71 g (5.94 mmol) of pivaloyl chloride is then added dropwise and the mixture is stirred at 0° C. for 3 h. 0.75 g (5.98 mmol) of glycine methyl ester hydrochloride are then added, and the mixture is stirred at 0° C. for 3 h, then allowed to warm to 20° C. and to stand overnight. 2N HCl is added to the reaction solution and it is extracted three times with dichloromethane, dried and concentrated, the residue is chromatographed using ethyl acetate/methanol (4:1) on silica gel, appropriate fractions are concentrated, the residue is recrystallized from diisopropyl ether and 1.44 g of the title compound are obtained, M.p. 150°–152° C.

EXAMPLE 3

N-(2-Hydroxyethyl)-5-[((phenylsulfonyl)amino)carbonyl]-pyridine-2-carboxamide a) Methyl 5-[((phenylsulfonyl)amino)carbonyl]pyridine-2-carboxamide The compound is obtained analogously to Example 1b) from 3.46 g (22 mmol) of benzenesulfonamide, 2.46 g (22 mmol) of potassium tert-butoxide and 4.0 g (20 mmol) of 2-methoxycarbonylpyridine-5-carbonyl chloride. After recrystallization from methanol, 1.6 g of product are obtained, M.p. 197°–198° C.

b) Analogously to Example 1c), the title compound is obtained from methyl 5-[((phenylsulfonyl)amino)carbonyl]pyridine-2-carboxylate and ethanolamine as a colorless, crystalline substance, M.p. 249°–250° C.

EXAMPLE 4

N-(2-Hydroxyethyl)-5-[(4-fluorophenylsulfonyl)amino]pyridine-2-carboxamide a) Methyl 5-[(4-fluorophenylsulfonyl)amino]pyridine-2-carboxylate 3.8 g (25 mmol) of methyl 5-aminopyridine-2-carboxylate are dissolved in 75 ml of anhydrous pyridine and treated in portions with 5.8 g (30 mmol) of 4-fluorobenzenesulfonyl chloride, the temperature of the reaction solution increasing to 35° C. After 1 h, the mixture is concentrated in vacuo, and the residue is triturated with water, filtered off with suction, washed with water and dried. 7.3 g of product are obtained, M.p. 183°–185° C.

b) 3.1 g (10 mmol) of the above compound are heated at a bath temperature of 100° C. for 1 h in 10 ml of aminoethanol. The reaction mixture is then diluted with 100 ml of water, acidified with half-concentrated aqueous hydrochloric acid with cooling, and the precipitate is filtered off with suction, washed and dried. For further purification, this crude product is dissolved in 25 ml of cold methanol and treated with water until the onset of turbidity. 2.9 g of the colorless, crystalline title compound are obtained, M.p. 144°–146° C.

EXAMPLE 5

N-(2-Methoxyethyl)-5-[(4-fluorophenylsulfonyl)amino]pyridine-2-carboxamide 0.5 g (1.61 mmol) of methyl 5-[(4-fluorophenylsulfonyl)amino]pyridine-2-carboxylate (compound from Example 4a) is stirred at 70° C. for 3 h in 5 ml of 2-methoxyethylamine. The mixture is concentrated, the residue is dissolved in water, the solution is acidified with conc. HCl, the solid is filtered off with suction and washed with water and 0.53 g of the title compound is obtained in the form of colorless crystals, M.p. 154° C.

EXAMPLE 6

N-Methoxycarbonylmethyl-5-[(4-fluorophenylsulfonyl)amino]pyridine-2-carboxamide a) 5-[(4-Fluorophenylsulfonyl)amino]pyridine-2-carboxylic acid 1.6 g (5.16 mmol) of the compound from Example 4a) are introduced into 100 ml of 1.5N methanolic NaOH with stirring at 20° C. and the mixture is additionally stirred for 1 h. It is then concentrated in vacuo, the residue is dissolved using 30 ml of water, and the solution is acidified to pH 1 using conc. aqueous HCl. 1.5 g of product are obtained, M.p. 240° C. (decomposition).

b) 1.5 ml (10.7 mmol) of triethylamine are added at 20° C. with stirring to 1.5 g (5.07 mmol) of the above compound in 100 ml of anhydrous tetrahyrofuran. After 30 minutes, 0.53 ml (5.4 mmol) of ethyl chloroformate is added at 0° C., the mixture is stirred at 0° C. for 30 minutes, 0.65 g (5 mmol) of glycine methyl ester hydrochloride is added, the mixture is stirred at 0° C. for 1 h, allowed to warm to 20° C. and concentrated in vacuo, the residue is treated with 50 ml of satd. aqueous NaHCO₃ solution and extracted three times with dichloromethane, the extracts are dried and concentrated and the residue is chromatographed on silica gel using ethyl acetate. The title compound is obtained after appropriate fractions have been concentrated and crystallized using diethyl ether, 0.77 g, M.p. 146°–148° C.

EXAMPLE 7

N-(2-Hydroxyethyl)-5-[(2,5-bis(1,1,1-trifluoroethoxy)phenylsulfonyl)amino]pyridine-2-carboxamide a) Methyl 5-[(2,5-bis(1,1,1-trifluoroethoxy)phenylsulfonyl)amino]pyridine-2-carboxylate is obtained analogously to Example 4a) from 0.5 g (3.3 mmol) of methyl 5-aminopyridine-2-carboxylate and 1.3 g (3.5 mmol) of 2,5-bis(1,1,1-trifluoroethoxy)benzenesulfonyl chloride. 1.3 g of product crystallize after treatment of the evaporation residue with water, M.p. 158°–160° C.

b) The title compound is obtained analogously to Example 4b) from 0.4 g (0.82 mmol) of the above compound and 5 ml of aminoethanol. After chromatography on silica gel, the evaporation residue of appropriate fractions is crystallized using diethyl ether; yield 0.38 g, M.p. 165°–167° C.

EXAMPLE 8

N-(2-Hydroxyethyl)-5-[((4-n-butoxyphenylsulfonyl)amino)carbonyl]pyridine-2-carboxamide a) 4-n-Butoxybenzenesulfonamide 100 ml of methanolic ammonia solution are added dropwise with ice-cooling to 10 g of 4-n-butoxybenzenesulfonyl chloride. After stirring at 20° C. for ½ hour, the mixture is concentrated, the residue is treated with water, acidified to pH 1–2 and filtered off with suction, M.p. 99°–101° C.

b) Methyl 5-[((4-n-butoxyphenylsulfonyl)amino)carbonyl]pyridine-2-carboxylate 4.6 g (20 mmol) of the above compound, 2.5 g (22 mmol) of potassium tert-butoxide and 5.0 g (25 mmol) of 2-methoxycarbonylpyridine-5-carbonyl chloride are reacted analogously to Example 1b). Precipitated potassium salt is acidified using 2N HCl in a dioxane/water mixture. The precipitated product is filtered off with suction and dried; yield 1.5 g; M.p. 174°–176° C.

c) The title compound is obtained from 0.2 g (0.51 mmol) of the above compound and 5 ml of aminoethanol at 80° C. (1 h). The mixture is treated with water and acidified, the solid is filtered off with suction and dried and 0.19 g of colorless crystalline substance is obtained, M.p. 176°–178° C.

EXAMPLE 9

N-(2-Hydroxyethyl)-5-[((4-trifluoromethoxyphenylsulfonyl)amino)carbonyl]pyridine-2-carboxamide a) 4-Trifluoromethoxybenzenesulfonamide is obtained from the corresponding sulfonyl chloride by reaction with methanolic ammonia solution. The crude product is treated with water, the mixture is acidified, and the solid is filtered off with suction and dried, M.p. 143°–145° C.

b) Methyl 5-[((4-trifluoromethoxyphenylsulfonyl)amino)carbonyl]pyridine-2-carboxylate 4.8 g (20 mmol) of the above compound, 2.5 g (22 mmol) of potassium tert-butoxide in dioxane and 5 g (25 mmol) of 2-methoxycarbonylpyridine-5-carbonyl chloride are reacted analogously to Example 1b). After concentration, the residue is taken up in water and acidified, and the precipitate is filtered off with suction and dried; 3.4 g of crude product (M.p. 210°–214° C.) which is recrystallized from 75 ml of ethyl acetate, 1.5 g of colorless crystalline substance, M.p. 221°–223° C.

c) The title compound, M.p. 202°–204° C., is obtained from 0.6 g (about 1.5 mmol) of the above compound and 5 ml of aminoethanol after heating at 80° C. for 1 hour, cooling, treatment with water, acidification with half-concentrated HCl, extraction with ethyl acetate, drying, concentration and crystallization using diethyl ether.

EXAMPLE 10

N-(2-Hydroxyethyl)-5-[((2,5-bis-[1,1,1-trifluoroethyloxy]phenylsulfonyl)amino)carbonyl]pyridine-2-carboxamide The title compound is obtained analogously to Example 1c) from methyl 5-[((2,5-bis-[1,1,1-trifluoroethyloxy]phenylsulfonyl)amino)carbonyl]pyridine-2-carboxylate and aminoethanol. It is crystallized using diethyl ether, M.p. 190°–192° C.

EXAMPLE 11

N-(2-Hydroxyethyl)-5-[((4-[2,2,2-trifluoroethyloxy]phenylsulfonyl)amino)carbonyl]pyridine-2-carboxamide

EXAMPLE 12

N-(3-Hydroxypropyl)-5-[((4-[2,2,2-trifluoroethyloxy]phenylsulfonyl)amino)carbonyl]pyridine-2-carboxamide

EXAMPLE 13

N-(2-Methoxyethyl)-5-[((4-[2,2,2-trifluoroethyloxy]phenylsulfonyl)amino)carbonyl]pyridine-2-carboxamide

EXAMPLE 14

N-Methoxycarbonylmethyl-5-[((4-[2,2,2-trifluoroethyloxy]phenylsulfonyl)amino)carbonyl]pyridine-2-carboxamide

EXAMPLE 15

N-Glycyl-5-[((4-[2,2,2-trifluoroethyloxy]phenylsulfonyl)amino)carbonyl]pyridine-2-carboxamide

EXAMPLE 16

N-(2-Hydroxyethylamino)glycyl-5-[((4-[2,2,2-trifluoroethyloxy]phenylsulfonyl)amino)carbonyl]pyridine-2-carboxamide

EXAMPLE 17

N-(2-Hydroxyethyl)-5-[((4-[2,2,3,3,3-pentafluoropropyloxy]phenylsulfonyl)amino)carbonyl]pyridine-2-carboxamide

EXAMPLE 18

N-(2-Methoxyethyl)-5-[((4-[2,2,3,3,3-pentafluoropropyloxy]phenylsulfonyl)amino)carbonyl]pyridine-2-carboxamide

EXAMPLE 19

N-Ethyl-5-[((4-methoxyphenylsulfonyl)amino)carbonyl]-pyridine-2-carboxamide

EXAMPLE 20

N-n-Butyl-5-[((4-methoxyphenylsulfonyl)amino)carbonyl]pyridine-2-carboxamide

EXAMPLE 21

N-Cyclohexyl-5-[((4-methoxyphenylsulfonyl)amino)carbonyl]pyridine-2-carboxamide

EXAMPLE 22

N-Benzyl-5-[((4-methoxyphenylsulfonyl)amino)carbonyl]-pyridine-2-carboxamide

EXAMPLE 23

N-(2-Ethoxyethyl)-5-[((4-[2,2,3,3,4,4,4-heptafluorobutyloxy]phenylsulfonyl)amino)carbonyl]pyridine-2-carboxamide

EXAMPLE 24

N-Methoxycarbonylmethyl-5-[((4-[2,2,3,3,4,4,4-heptafluorobutyloxy]phenylsulfonyl)amino)carbonyl]pyridine-2-carboxamide

EXAMPLE 25

N-(2-Hydroxyethyl)-5-[((4-phenoxyphenylsulfonyl)amino)carbonyl]pyridine-2-carboxamide

EXAMPLE 26

N-(2-Ethoxyethyl)-5-[((4-phenoxyphenylsulfonyl)amino)carbonyl]pyridine-2-carboxamide

EXAMPLE 27

N-(2-Methoxyethyl)-5-[((4-phenoxyphenylsulfonyl)amino)carbonyl]pyridine-2-carboxamide

EXAMPLE 28

N-(2-Hydroxyethyl)-5-[((2-phenylphenylsulfonyl)amino)carbonyl]pyridine-2-carboxamide

EXAMPLE 29

N-Methoxycarbonylmethyl-5-[((2-phenylphenylsulfonyl)amino)carbonyl]pyridine-2-carboxamide

EXAMPLE 30

N-(2-Hydroxyethyl)-5-[((n-butylsulfonyl)amino)carbonyl]pyridine-2-carboxamide
M.p. 168°–169° C. (from water)

EXAMPLE 31

N-(2-Methoxyethyl)-5-[((n-butylsulfonyl)amino)carbonyl]pyridine-2-carboxamide

EXAMPLE 32

N-Methoxycarbonylmethyl-5-[((n-butylsulfonyl)amino)carbonyl]pyridine-2-carboxamide

EXAMPLE 33

N-(2-Hydroxyethyl)-5-[((4-[3-(trifluoromethyl)phenoxy]phenylsulfonyl)amino)carbonyl]pyridine-2-carboxamide
M.p. 167°–168° C. (from water)

EXAMPLE 34

N-Methoxycarbonylmethyl-5-[((4-[3-(trifluoromethyl)phenyloxy]phenylsulfonyl)amino)carbonyl]pyridine-2-carboxamide

EXAMPLE 35

N-(2-Methoxyethyl)-5-[((1-naphthylsulfonyl)amino)carbonyl]pyridine-2-carboxamide

EXAMPLE 36

N-(2-Hydroxyethyl)-5-[((1naphthylsulfonyl)amino)carbonyl[pyridine-2-carboxamide

EXAMPLE 37

N-(2-Methoxypropyl)-5-[((1-naphthylsulfonyl)amino)carbonyl[pyridine-2-carboxamide

EXAMPLE 38

N-Methoxycarbonylmethyl-5-[((1-naphthylsulfonyl)amino)carbonyl[pyridine-2-carboxamide

EXAMPLE 39

N-(2-Hydroxyethyl)-5-[((2-naphthylsulfonyl)amino)carbonyl]pyridine-2-carboxamide

EXAMPLE 40

N-(2-Hydroxyethyl)-5-[((phenylmethylsulfonyl)amino)carbonyl]pyridine-2-carboxamide

EXAMPLE 41

N-(2-Hydroxyethyl)-5-[((2-phenylethylsulfonyl)amino)carbonyl]pyridine-2-carboxamide

EXAMPLE 42

N-(2-Hydroxyethyl)-5-[((2-(4-fluorophenyl)ethylsulfonyl) amino)carbonyl]pyridine-2-carboxamide

EXAMPLE 43

N-(2-Hydroxyethyl)-5-[((2-(4-methoxyphenyl)ethylsulfonyl)amino)carbonyl]pyridine-2-carboxamide

EXAMPLE 44

N-(2-Hydroxyethyl)-5-[((3-phenyl-n-propylsulfonyl)amino)carbonyl]pyridine-2-carboxamide

EXAMPLE 45

N-(2-Hydroxyethyl)-5-[((4-phenyl-n-butylsulfonyl)amino)carbonyl]pyridine-2-carboxamide

EXAMPLE 46

N-(2-Hydroxyethyl)-5-[((2-phenoxyethylsulfonyl)amino)carbonyl]pyridine-2-carboxamide

EXAMPLE 47

N-(2-Hydroxyethyl)-5-[((2-(4-fluorophenoxy)ethylsulfonyl) amino)carbonyl]pyridine-2-carboxamide

EXAMPLE 48

N-(2-Methoxyethyl)-5-[((phenylmethylsulfonyl)amino)carbonyl]pyridine-2-carboxamide

EXAMPLE 49

N-(2-Methoxyethyl)-5-[((2-phenylethylsulfonyl)amino)carbonyl]pyridine-2-carboxamide

EXAMPLE 50

N-(2-Methoxyethyl)-5-[((2-(4-fluorophenyl)ethylsulfonyl) amino)carbonyl]pyridine-2-carboxamide

EXAMPLE 51

N-(2-Methoxyethyl)-5-[((2-(4methoxyphenyl)ethylsulfonyl) amino)carbonyl]pyridine-2-carboxamide

EXAMPLE 52

N-(2-Methoxyethyl)-5-[((3-phenyl-n-propylsulfonyl)amino)carbonyl]pyridine-2-carboxamide

EXAMPLE 53

N-(2-Methoxyethyl)-5-[((4-phenyl-n-butylsulfonyl)amino)carbonyl]pyridine-2-carboxamide

EXAMPLE 54

N-(2-Methoxyethyl)-5-[((2-phenoxyethylsulfonyl)amino)carbonyl]pyridine-2-carboxamide

EXAMPLE 55

N-(2-Methoxyethyl)-5-[((2-(4-fluorophenoxy)ethylsulfonyl) amino)carbonyl]pyridine-2-carboxamide

EXAMPLE 56

N-(2-Propoxycarbonylmethyl)-5-[((phenylmethylsulfonyl)amino)carbonyl]pyridine-2-carboxamide

EXAMPLE 57

N-(2-Propoxycarbonylmethyl)-5-[((2-phenylethylsulfonyl)amino)carbonyl]pyridine-2-carboxamide

EXAMPLE 58

N-(2-Propoxycarbonylmethyl)-5[((2-(4-fluorophenyl)ethylsulfonyl)amino)carbonyl]pyridine-2-carboxamide

EXAMPLE 59

N-(2-Propoxycarbonylmethyl)-5-[((2-(4-methoxyphenyl)ethylsulfonyl)amino)carbonyl]pyridine-2-carboxamide

EXAMPLE 60

N-(2-Propoxycarbonylmethyl)-5-[((3-phenyl-n-propylsulfonyl)amino)carbonyl]pyridine-2-carboxamide The following were prepared analogously from 2methoxycarbonylpyridine-4-carbonyl chloride (or 4-carboxylic acid):

EXAMPLE 61

N-(2-Hydroxyethyl)-4-[((4-[2,2,2-trifluoroethyloxy]-phenylsulfonyl)amino)carbonyl]pyridine-2-carboxamide

EXAMPLE 62

N-(2-Methoxyethyl)-4-[((4-[2,2,2-trifluoroethyloxy]-phenylsulfonyl)amino)carbonyl]pyridine-2-carboxamide

EXAMPLE 63

N-Methoxycarbonylmethyl-4-[((4-[2,2,2-trifluoroethyloxy] phenylsulfonyl)amino)carbonyl]pyridine-2-carboxamide

EXAMPLE 64

N-(2-Hydroxyethyl)-4-[((4-phenoxyphenylsulfonyl)amino)carbonyl]pyridine-2-carboxamide

EXAMPLE 65

N-(2-Ethoxyethyl)-4-[((4-phenoxyphenylsulfonyl)amino)carbonyl]pyridine-2-carboxamide

EXAMPLE 66

N-(2-Hydroxyethyl)-4-[((2-phenylphenylsulfonyl)amino)carbonyl]pyridine-2-carboxamide

EXAMPLE 67

N-Methoxycarbonylmethyl-4-[((2-phenylphenylsulfonyl)amino)carbonyl]pyridine-2-carboxamide

EXAMPLE 68

N-(2-Hydroxyethyl)-4-[((n-butylsulfonyl)amino)carbonyl]pyridine-2-carboxamide

EXAMPLE 69

N-(2-Methoxyethyl)-4-[((n-butylsulfonyl)amino)carbonyl]pyridine-2-carboxamide

EXAMPLE 70

N-Methoxycarbonylmethyl-4-[((n-butylsulfonyl)amino)carbonyl]pyridine-2-carboxamide Said compounds are also obtainable as pyridine-N-oxides after oxidation.

The following compounds of the formula I, in which X is a single bond, can be prepared from the corresponding compounds analogously to Example 4 to 5 as in Scheme 1:

Alkyl amide derivatives and the glycyl amide derivatives were (are) prepared as described on page [lacuna].

EXAMPLE 71

N-(2-Hydroxyethyl)-5-[(4-[2,2,2-trifluoroethyloxy]phenylsulfonyl)amino]pyridine-2-carboxamide

EXAMPLE 72

N-(3-Hydroxypropyl)-5-[(4-[2,2,2-trifluoroethyloxy]phenylsulfonyl)amino]pyridine-2-carboxamide

EXAMPLE 73

N-(2-Methoxyethyl)-5-[(4-[2,2,2-trifluoroethyloxy]phenylsulfonyl)amino]pyridine-2-carboxamide

EXAMPLE 74

N-Methoxycarbonylmethyl-5-[(4-[2,2,2-trifluoroethyloxy] phenylsulfonyl)amino]pyridine-2-carboxamide

EXAMPLE 75

N-Carboxymethyl-5-[(4-[2,2,2-trifluoroethyloxy]phenylsulfonyl)amino]pyridine-2-carboxamide

EXAMPLE 76

N-(2-Hydroxyethyl)-5-[(4-[2,2,3,3,4,4,4-heptafluorobutyloxy]phenylsulfonyl)amino]pyridine-2-carboxamide

EXAMPLE 77

N-(2-Methoxyethyl)-5-[(4-[2,2,3,3,4,4,4-heptafluorobutyloxy]phenylsulfonyl)amino]pyridine-2-carboxamide

EXAMPLE 78

N-(2-Ethoxyethyl)-5-[(4-[2,2,3,3,4,4,4-heptafluorobutyloxy]phenylsulfonyl)amino]pyridine-2-carboxamide

EXAMPLE 79

N-Methoxycarbonylmethyl-5-[(4-[2,2,3,3,4,4,4-heptafluorobutyloxy]phenylsulfonyl)amino]pyridine-2-carboxamide

EXAMPLE 80

N-(2-Hydroxyethyl)-5-[(4-phenoxyphenylsulfonyl)amino]pyridine-2-carboxamide

EXAMPLE 81

N-(2-Ethoxyethyl)-5-[(4-phenoxyphenylsulfonyl)amino]pyridine-2-carboxamide

EXAMPLE 82

N-(2-Methoxyethyl)-5-[(4-phenoxyphenylsulfonyl)amino]pyridine-2-carboxamide

EXAMPLE 83

N-(2-Hydroxyethyl)-5-[(2-phenylphenylsulfonyl)amino]pyridine-2-carboxamide

EXAMPLE 84

N-Methoxycarbonylmethyl-5-[(2-phenylphenylsulfonyl)amino]pyridine-2-carboxamide

EXAMPLE 85

N-(2-Hydroxyethyl)-5-[(n-butylsulfonyl)amino]pyridine2-carboxamide

EXAMPLE 86

N-(2-Methoxyethyl)-5-[(n-butylsulfonyl)amino]pyridine2-carboxamide

EXAMPLE 87

N-Methoxycarbonylmethyl-5-[(n-butylsulfonyl)amino]pyridine-2-carboxamide

EXAMPLE 88

N-(2-Hydroxyethyl)-5-[(4-[3-(trifluoromethyl)phenoxy]phenylsulfonyl)amino]pyridine-2-carboxamide

EXAMPLE 89

N-Methoxycarbonylmethyl-5-[(4-[3-(trifluoromethyl)phenyloxy]phenylsulfonyl)amino]pyridine-2-carboxamide

EXAMPLE 90

N-(2-Hydroxyethyl)-4-[(4-phenoxypohenylsulfonyl)amino]pyridine-2-carboxamide

EXAMPLE 91

N-(2-Methoxyethyl)-4-[(4-phenoxyphenylsulfonyl)amino]pyridine-2-carboxamide

EXAMPLE 92

N-(2-Hydroxyethyl)-4-[(2-phenylphenylsulfonyl)amino]pyridine-2-carboxamide

EXAMPLE 93

N-(2-Hydroxyethyl)-4-[(n-butylsulfonyl)amino]pyridine-2-carboxamide

EXAMPLE 94

N-Methoxycarbonylmethyl-4-[(n-butylsulfonyl)amino]pyridine-2-carboxamide

EXAMPLE 95

N-(2-Hydroxyethyl)-4-[(4-[3-(trifluoromethyl)phenoxy]phenylsulfonyl)amino]pyridine-2-carboxamide

EXAMPLE 96

N-(2-Hydroxyethyl)-5-[((4,5-dibromo-2-thienylsulfonyl)amino)carbonyl]pyridine-2-carboxamide

EXAMPLE 97

N-(2-Methoxyethyl)-5-[((4,5-dibromo-2-thienylsulfonylamino)carbonyl]pyridine-2-carboxamide

EXAMPLE 98

N-Ethyl-5-[((4,5-dibromo-2-thienylsulfonyl)amino)carbonyl]pyridine-2-carboxamide

EXAMPLE 99

N-Ethyl-5-[((5-chloro-2-thienylsulfonyl)amino)carbonyl]pyridine-2-carboxamide

EXAMPLE 100

N-(2-Hydroxyethyl)-5-[((4-[4,6-dichloro-2-quinolyl]phenylsulfonyl)amino)carbonyl]pyridine-2-carboxamide

EXAMPLE 101

N-(2-Hydroxyethyl)-5-[((5-chloro-2-thienylsulfonyl)amino)carbonyl]pyridine-2-carboxamide

EXAMPLE 102

N-(3-Methoxypropyl)-5-[((5-chloro-2-thienylsulfonyl)amino)carbonyl]pyridine-2-carboxamide

EXAMPLE 103

N-Ethyl-5-[((2-thienylsulfonyl)amino)carbonyl]pyridine-2-carboxamide

EXAMPLE 104

N-n-Butyl-5-[((2-thienylsulfonyl)amino)carbonyl]pyridine-2-carboxamide

EXAMPLE 105

N-(2-Methoxyethyl)-5-[((8-quinolylsulfonyl)amino)carbonyl]pyridine-2-carboxamide

EXAMPLE 106

N-(2-Methoxyethyl)-5-[((4-[4,6-dichloro-4-quinolyl]phenylsulfonyl)amino)carbonyl]pyridine-2-carboxamide The following compounds were obtained within the meaning of the invention by aminolysis of the ester from Example 3a) with the corresponding amines:

EXAMPLE 109

N-(2-Methoxyethyl)-5-[((phenylsulfonyl)amino)carbonyl]pyridine-2-carboxamide
M.p. 190°–191° C. (from water)

EXAMPLE 110

N-Methoxycarbonylmethyl-5-[((phenylsulfonyl)amino)carbonyl]pyridine-2-carboxamide M.p. 125°–126° C. (from water)

EXAMPLE 111

N-carboxymethyl-5-[((phenylsulfonyl)amino)carbonyl]pyridine-2-carboxamide
M.p. 190°–191° C. (from water)

EXAMPLE 112

N-(2-Hydroxyethyl)-5-[((4-((2-phenylethyl)aminocarbonyl)phenylsulfonyl)amino)carbonyl]pyridine-2-carboxamide a) 4-((2-Phenylethyl)aminocarbonyl)benzenesulfonamide 20.1 g (0.1 mol) of 4-carboxybenzenesulfonamide were suspended in 300 ml of anhydrous tetrahydrofuran and treated dropwise at 0° C. with stirring with 15.2 ml (0.11 mol) of triethylamine. After 30 min, 10.5 ml (0.11 mol) of ethyl chloroformate were added dropwise at 0° C., the mixture was stirred at this temperature for 1 h, cooled to −10° C. and 12.1 g (0.1 mol, 12.5 ml) of 2-phenylethylamine in 30 ml of anhydrous tetrahydrofuran were added dropwise. After 1 h at 0° C., the mixture was warmed to 20° C. and concentrated in vacuo, the solid residue was treated with water, filtered off with suction and recrystallized from ethanol, and 20.4 g of product were obtained, M.p. 243°–245° C.

b) Methyl 5-[((4-((2-phenylethyl)aminocarbonyl)phenylsulfonyl)amino)carbonyl]pyridine-2-carboxylate 1.8 g (10 mmol) of 2-methoxycarbonylpyridine-5-carboxylic acid were suspended in 300 ml of anhydrous acetonitrile and treated at 20° C. with stirring with 3.0 g (10 mmol) of the above compound, 2.1 g (10 mmol) of N,N'-dicyclohexylcarbodiimide and 1.2 g (10 mmol) of 4-N,N-dimethylaminopyridine and stirred at 20° C. for 20 h. Insoluble matter was then filtered off, the filtrate was concentrated in vacuo, the residue was taken up in 200 ml of dichloromethane, and the solution was extracted twice with saturated aqueous NaHCO$_3$ solution, then with 100 ml of 2N aqueous HCl. The crystalline precipitate was then treated with warm methanol, filtered off with suction and dried. 2.2 g of the ester were obtained, M.p. 228°–230° C.

c) The title compound was obtained by stirring 0.8 g (1.7 mmol) of the above compound at 80° to 90° C. for 1 h in 10 ml of 2-aminoethanol. The excess 2-aminoethanol was distilled off in vacuo, the residue was taken up in a little water, and the mixture was acidified to pH 1 using aqueous HCl. The crystalline product was treated with ethyl acetate again, filtered off with suction and dried: 0.73 g of product as colorless crystals, M.p. 228°–230° C.

EXAMPLE 113

N-(2-Hydroxyethyl)-5-[((4benzylaminocarbonyl)phenylsulfonyl)amino)carbonyl]pyridine-2-carboxamide

EXAMPLE 114

N-(2-Hydroxyethyl)-5-[((4-((3-phenyl-n-propyl)aminocarbonyl)phenylsulfonyl)amino)carbonyl]pyridine-2-carboxamide

EXAMPLE 115

N-(2-Hydroxyethyl)-5-[((4-[4-phenyl-n-butyl)aminocarbonyl)phenylsulfonyl)amino)carbonyl]pyridine-2-carboxamide

EXAMPLE 116

N-(2-Hydroxyethyl)-5-[((4-[2-(4-methoxyphenyl)ethyl)aminocarbonyl)phenylsulfonyl)amino)carbonyl]pyridine-2-carboxamide
M.p. 243°–244° C. (from water)

EXAMPLE 117

N-(2-Hydroxyethyl)-5-[((4-((2-(3,4-dimethoxyphenyl)ethyl) aminocarbonyl)phenylsulfonyl)amino)carbonyl]pyridine-2-carboxamide
M.p. 201°–203° C. (ethyl acetate)

EXAMPLE 118

N-(2-Hydroxyethyl)-5-[((4-((2-(2-methoxyphenyl)ethyl)aminocarbonyl)phenylsulfonyl)amino)carbonyl]pyridine-2-carboxamide

EXAMPLE 119

N-(2-Hydroxyethyl)-5-[((4-((2-(4-fluorophenyl)ethyl)aminocarbonyl)phenylsulfonyl)amino)carbonyl]pyridine-2-carboxamide

EXAMPLE 120

N-(2-Hydroxyethyl)-5-[((4-((2-(4-chlorophenyl)ethyl)aminocarbonyl)phenylsulfonyl)amino)carbonyl]pyridine-2-carboxamide

EXAMPLE 121

N-(2-Hydroxyethyl)-5-[((4-(ethylaminocarbonyl)phenylsulfonyl)amino)carbonyl]pyridine-2-carboxamide

EXAMPLE 122

N-(2-Hydroxyethyl)-5-[((4-(n-butylaminocarbonyl)phenylsulfonyl)amino)carbonyl]pyridine-2-carboxamide
M.p. 245° C.

EXAMPLE 123

N-(2-Hydroxyethyl)-5-[((4-(n-hexylaminocarbonyl)phenylsulfonyl)amino)carbonyl]pyridine-2-carboxamide

EXAMPLE 124

N-(2-Hydroxyethyl)-5-[((4-(N,N-di-n-butylaminocarbonyl)phenylsulfonyl)amino)carbonyl]pyridine-2-carboxamide

EXAMPLE 125

N-(2-Hydroxyethyl)-5-[((4-(cyclohexylaminocarbonyl)phenylsulfonyl)amino)carbonyl]pyridine-2-carboxamide

EXAMPLE 126

N-(2-Hydroxyethyl)-5-[((4-(2-methoxyethyl)aminocarbonyl)phenylsulfonyl)amino)carbonyl]pyridine-2-carboxamide

EXAMPLE 127

N-(2-Hydroxyethyl)-5[((4-((2-ethoxyethyl)aminocarbonyl)phenylsulfonly)amino)carbonyl]pyridine-2-carboxamide

EXAMPLE 128

N-(2-Hydroxyethyl)-5-[((4-((3-ethoxypropyl)aminocarbonyl)phenylsulfonyl)amino)carbonyl]pyridine-2-carboxamide

EXAMPLE 129

N-(2-Hydroxyethyl)-5-[((4-((2-phenoxyethyl)aminocarbonyl)phenylsulfonyl)amino)carbonyl]pyridine-2-carboxamide

EXAMPLE 130

N-(2-Hydroxyethyl)-5-[((3-(benzylaminocarbonyl)phenylsulfonyl)amino)carbonyl]pyridine-2-carboxamide

EXAMPLE 131

N-(2-Hydroxyethyl)-5-[((3-((3-phenylpropyl)aminocarbonyl)phenylsulfonyl)amino)carbonyl]pyridine-2-carboxamide

EXAMPLE 132

N-(2-Hydroxyethyl)-5-[((3-((4-phenyl-n-butyl)aminocarbonyl)phenylsulfonyl)amino)carbonyl]pyridine-2-carboxamide

EXAMPLE 133

N-(2-Hydroxyethyl)-5-[((3-((2-(4-methoxyphenyl)ethyl)aminocarbonyl)phenylsulfonyl)amino)carbonyl]pyridine-2-carboxamide

EXAMPLE 134

N-(2-Hydroxyethyl)-5-[((3-((2-(3,4dimethoxyphenyl)ethyl)aminocarbonyl)phenylsulfonyl)amino)carbonyl]pyridine-2-carboxamide

EXAMPLE 135

N-(2-Hydroxyethyl)-5-[((3-((2-(2-methoxyphenyl)ethyl)aminocarbonyl)phenylsulfonyl)amino)carbonyl]pyridine-2-carboxamide

EXAMPLE 136

N-(2-Hydroxyethyl)-5-[((3-((2-(4-fluorophenyl)ethyl)aminocarbonyl)phenylsulfonyl)amino)carbonyl]pyridine-2-carboxamide

EXAMPLE 137

N-(2-Hydroxyethyl)-5-[((3-((2-(4-chlorophenyl)ethyl)aminocarbonyl)phenylsulfonyl)amino)carbonyl]pyridine-2-carboxamide

EXAMPLE 138

N-(2-Hydroxyethyl)-5-[((3-(ethylaminocarbonyl)phenylsulfonyl)amino)carbonyl]pyridine-2-carboxamide

EXAMPLE 139

N-(2-Hydroxyethyl)-5-[((3-(n-butylaminocarbonyl)phenylsulfonyl)amino)carbonyl]pyridine-2-carboxamide

EXAMPLE 140

N-(2-Hydroxyethyl)-5-[((3-(n-hexylaminocarbonyl)phenylsulfonyl)amino)carbonyl]pyridine-2-carboxamide

EXAMPLE 141

N-(2-Hydroxyethyl)-5-[((3-(N,N-di-n-butylaminocarbonyl)phenylsulfonyl)amino)carbonyl]pyridine-2-carboxamide

EXAMPLE 142

N-(2-Hydroxyethyl)-5-[((3-(cyclohexylaminocarbonyl)phenylsulfonyl)amino)carbonyl]pyridine-2-carboxamide

EXAMPLE 143

N-(2-Hydroxyethyl)-5-[((3-((2-methoxyethyl)aminocarbonyl)phenylsulfonyl)amino)carbonyl]pyridine-2-carboxamide

EXAMPLE 144

N-(2-Hydroxyethyl)-5-[((3-((2-ethoxyethyl)aminocarbonyl)phenylsulfonyl)amino)carbonyl]pyridine-2-carboxamide

EXAMPLE 145

N-(2-Hydroxyethyl)-5-[((3-((3-methoxypropyl)aminocarbonyl)phenylsulfonyl)amino)carbonyl]pyridine-2-carboxamide

EXAMPLE 146

N-(2-Hydroxyethyl)-5-[((3-((2-phenylethyl)aminocarbonyl)phenylsulfonyl)amino)carbonyl]pyridine-2-carboxamide
  M.p. 189°–191° C.

EXAMPLE 147

N-(2-Hydroxyethyl)-5-[((3-((2-phenoxyethyl)aminocarbonyl)phenylsulfonyl)amino)carbonyl]pyridine-2-carboxamide

EXAMPLE 148

N-(2-Methoxyethyl)-5-[((4-(benzylaminocarbonyl)phenylsulfonyl)amino)carbonyl]pyridine-2-carboxamide

EXAMPLE 149

N-(2-Methoxyethyl)-5-[((4-((3-phenyl-n-propyl)aminocarbonyl)phenylsulfonyl)amino)carbonyl]pyridine-2-carboxamide

EXAMPLE 150

N-(2-Methoxyethyl)-5-[((4-((4-phenyl-n-butyl)aminocarbonyl)phenylsulfonyl)amino)carbonyl]pyridine-2-carboxamide

EXAMPLE 151

N-(2-Methoxyethyl)-5-[((4-((2-(4-methoxyphenyl)ethyl)aminocarbonyl)phenylsulfonyl)amino)carbonyl]pyridine-2-carboxamide

EXAMPLE 152

N-(2-Methoxyethyl)-5-[((4-((2-(3,4-dimethoxyphenyl)ethyl) aminocarbonyl)phenylsulfonyl)amino)carbonyl]pyridine-2-carboxamide
  M.p. 161°–163° C. (ethyl acetate)

EXAMPLE 153

N-(2-Methoxyethyl)-5-[((4-((2-(2-methoxyphenyl)ethyl)aminocarbonyl)phenylsulfonyl)amino)carbonyl]pyridine-2-carboxamide

EXAMPLE 154

N-(2-Methoxyethyl)-5-[((4-((2-(4-fluorophenyl)ethyl)aminocarbonyl)phenylsulfonyl)amino)carbonyl]pyridine-2-carboxamide

EXAMPLE 155

N-(2-Methoxyethyl)-5-[((4-((2-(4-chlorophenyl)ethyl)aminocarbonyl)phenylsulfonyl)amino)carbonyl]pyridine-2-carboxamide

EXAMPLE 156

N-(2-Methoxyethyl)-5-[((4-(ethylaminocarbonyl)phenylsulfonyl)amino)carbonyl]pyridine-2-carboxamide

EXAMPLE 157

N-(2-Methoxyethyl)-5-[((4-(n-butylaminocarbonyl)phenylsulfonyl)amino)carbonyl]pyridine-2-carboxamide

EXAMPLE 158

N-(2-Methoxyethyl)-5-[((4-(n-hexylaminocarbonyl)phenylsulfonyl)amino)carbonyl]pyridine-2-carboxamide

EXAMPLE 159

N-(2-Methoxyethyl)-5-[((4-(N,N-di-n-butylaminocarbonyl)phenylsulfonyl)amino)carbonyl]pyridine-2-carboxamide

EXAMPLE 160

N-(2-Methoxyethyl)-5-[((4-(cyclohexylaminocarbonyl)phenylsulfonyl)amino)carbonyl]pyridine-2-carboxamide

EXAMPLE 161

N-(2-Methoxyethyl)-5-[((4-((2-methoxyethyl)aminocarbonyl)phenylsulfonyl)amino)carbonyl]pyridine-2-carboxamide

EXAMPLE 162

N-(2-Methoxyethyl)-5-[((4-((2-ethoxyethyl)aminocarbonyl)phenylsulfonyl)amino)carbonyl]pyridine-2-carboxamide

EXAMPLE 163

N-(2-Methoxyethyl)-5-[((4-((3-ethoxypropyl)aminocarbonyl)phenylsulfonyl)amino)carbonyl]pyridine-2-carboxamide

EXAMPLE 164

N-(2-Methoxymethyl)-5-[((4-((2-phenylethyl)aminocarbonyl)phenylsulfonyl)amino)carbonyl]pyridine-2-carboxamide

EXAMPLE 165

N-(2-Methoxymethyl)-5-[((4-((2-phenoxyethyl)aminocarbonyl)phenylsulfonyl)amino)carbonyl]pyridine-2-carboxamide

EXAMPLE 166

N-(2-Methoxyethyl)-5-[((3-(benzylaminocarbonyl)phenylsulfonyl)amino)carbonyl]pyridine-2-carboxamide

EXAMPLE 167

N-(2-Methoxyethyl)-5-[((3-((phenylpropyl)aminocarbonyl)phenysulfonyl)amino)carbonyl]pyridine-2-carboxamide

EXAMPLE 168

N-(2-Methoxyethyl)-5-[((3-Phenyl-n-butyl)aminocarbonyl)phenylsulfonyl)amino)carbonyl]pyridine-2-carboxamide

EXAMPLE 169

N-(2-Methoxyethyl)-5-[((3-((2-(3,4-dimethoxyphenyl)ethyl) aminocarbonyl)phenylsulfonyl)amino)carbonyl]pyridine-2-carboxamide

EXAMPLE 170

N-(2-Methoxyethyl)-5-[((3-((2-(3-methoxyphenyl)ethyl)aminocarbonyl)phenylsulfonyl)amino)carbonyl]pyridine-2-carboxamide

EXAMPLE 171

N-(2-Methoxyethyl)-5-[((3-((2-(2-methoxyphenyl)ethyl) aminocarbonyl)phenylsulfonyl)amino)carbonyl]pyridine-2-carboxamide

EXAMPLE 172

N-(2-Methoxyethyl)-5-[((3-((2-(4-fluorophenyl)ethyl)aminocarbonyl)phenylsulfonyl)amino)carbonyl]pyridine-2-carboxamide

EXAMPLE 173

N-(2-Methoxyethyl)-5-[((3-((2-(4-chlorophenyl)ethyl)aminocarbonyl)phenylsulfonyl)amino)carbonyl]pyridine-2-carboxamide

EXAMPLE 174

N-(2-Methoxyethyl)-5-[((3-(ethylaminocarbonyl)phenylsulfonyl)amino)carbonyl]pyridine-2-carboxamide

EXAMPLE 175

N-(2-Methoxyethyl)-5-[((3-(n-butylaminocarbonyl)phenylsulfonyl)amino)carbonyl]pyridine-2-carboxamide

EXAMPLE 176

N-(2-Methoxyethyl)-5-[((3-(n-hexylaminocarbonyl)phenylsulfonyl)amino)carbonyl]pyridine-2-carboxamide

EXAMPLE 177

N-(2-Methoxyethyl)-5-[((3-(N,N-di-di-n-butylaminocarbonyl)phenylsulfonyl)amino)carbonyl]pyridine-2-carboxamide

EXAMPLE 178

N-(2-Methoxyethyl)-5-[((3-(cyclohexylaminocarbonyl)phenylsulfonyl)amino)carbonyl]pyridine-2-carboxamide

EXAMPLE 179

N-(2-methoxyethyl)-5-[((3-((2-methoxyethyl)aminocarbonyl)phenylsulfonyl)amino)carbonyl]pyridine-2-carboxamide

EXAMPLE 180

N-(2-Methoxyethyl)-5-[((3-(2-ethoxyethyl)aminocarbonylphenylsulfonyl)amino)carbonyl]pyridine-2-carboxamide

EXAMPLE 181

N-(2-Methoxyethyl)-5-[((3-((3-methoxypropyl)aminocarbonyl)phenylsulfonyl)amino)carbonyl]pyridine-2-carboxamide

EXAMPLE 182

N-(2-Methoxymethyl)-5-[((3-((2-phenylethyl)aminocarbonyl)phenylsulfonyl)amino)carbonyl]pyridine-2-carboxamide

EXAMPLE 183

N-(2-Methoxymethyl)-5-[((3-((2-phenoxyethyl)aminocarbonyl)phenylsulfonyl)amino)carbonyl]pyridine-2-carboxamide

EXAMPLE 184

N-(2-Methoxyethyl)-5-[((4-(benzylaminocarbonyl)phenylsulfonyl)amino)carbonyl]pyridine-2-carboxamide

EXAMPLE 185

N-(2-Ethoxyethyl)-5-[((4-((3-phenylpropyl)aminocarbonyl)phenylsulfonyl)amino)carbonyl]pyridine-2-carboxamide

EXAMPLE 186

N-(2-Ethoxyethyl)-5-[((4-((4-phenyl-n-butyl)aminocarbonyl)phenylsulfonyl)amino)carbonyl]pyridine-2-carboxamide

EXAMPLE 187

N-(2-Ethoxethyl)-5-[((4-((2-(4-methoxyphenyl)ethyl)aminocarbonyl)phenylsulfonyl)amino)carbonyl]pyridine-2-carboxamide

EXAMPLE 188

N-(2-Ethoxyethyl)-5-[((4-((2-(3,4-dimethoxyphenyl)ethyl)aminocarbonyl)phenylsulfonyl)amino)carbonyl]pyridine-2-carboxamide

EXAMPLE 189

N-(2-Ethoxyethyl)-5-[((4-((2-(2-methoxyphenyl)ethyl)aminocarbonyl)phenylsulfonyl)amino)carbonyl]pyridine-2-carboxamide

EXAMPLE 190

N-(2-Ethoxyethyl)-5-[((4-((2-(4-fluorophenyl)ethyl)aminocarbonyl) phenylsulfonyl)amino)carbonyl]pyridine-2-carboxamide

EXAMPLE 191

N-(2-Ethoxyethyl)-5-[((4-((2-(4-chlorophenyl)ethyl)aminocarbonyl) phenylsulfonyl)amino)carbonyl]pyridine-2-carboxamide

EXAMPLE 192

N-(2-Ethoxyethyl)-5-[((4-(ethylaminocarbonyl) phenylsulfonyl) amino)carbonyl]pyridine-2-carboxamide

EXAMPLE 193

N-(2-Ethoxyethyl)-5-[((4-(n-butylaminocarbonyl) phenylsulfonyl)amino)carbonyl]pyridine-2-carboxamide

EXAMPLE 194

N-(2-Ethoxyethyl)-5-[((4-(n-hexylaminocarbonyl) phenylsulfonyl)amino)carbonyl]pyridine-2-carboxamide

EXAMPLE 195

N-(2-Ethoxyethyl)-5-[((4-(N,N-di-n-butylaminocarbonyl) phenylsulfonyl)amino)carbonyl]pyridine-2-carboxamide

EXAMPLE 196

N-(2-Ethoxyethyl)-5-[((4-(cyclohexylaminocarbonyl) phenylsulfonyl)amino)carbonyl]pyridine-2-carboxamide

EXAMPLE 197

N-(2-Ethoxyethyl)-5-[((4-((2-methoxyethyl) aminocarbonyl)phenylsulfonyl)amino)carbonyl]pyridine-2-carboxamide

EXAMPLE 198

N-(2-Ethoxyethyl)-5-[((4-((2-ethoxyethyl) aminocarbonyl)phenylsulfonyl)amino)carbonyl]pyridine-2-carboxamide

EXAMPLE 199

N-(2-Ethoxyethyl)-5-[((4-((3-ethoxypropyl) aminocarbonyl)phenylsulfonyl)amino)carbonyl]pyridine-2-carboxamide

EXAMPLE 200

N-(2-Ethoxyethyl)-5-[((4-((2-phenylethyl) aminocarbonyl)phenylsulfonyl)amino)carbonyl]pyridine-2-carboxamide

EXAMPLE 201

N-(2-Ethoxyethyl)-5-[((4-((2-phenoxyethyl) aminocarbonyl)phenylsulfonyl)amino)carbonyl]pyridine-2-carboxamide

EXAMPLE 202

N-Methoxycarbonylmethyl-5-[((4-((2-phenylethyl) aminocarbonyl)phenylsulfonyl)amino)carbonyl]pyridine-2-carboxamide sodium salt a) 5-[((4-((2-Phenylethyl)aminocarbonyl)phenylsulfonyl) amino)carbonyl]pyridine-2-carboxylic acid 0.7 g (1.5 mmol) of the methyl ester described in Example 112 b) was introduced into 100 ml of 1.5N methanolic NaOH at 20° C. with stirring. After a solution had been formed, a crystalline product later precipitated. The mixture was then stirred for an additional 30 min. It was concentrated in vacuo, the residue was dissolved in a mixture of water and tetrahydrofuran, the solution was acidified to pH=1 using aqueous HCl and concentrated in vacuo, and the colorless crystalline product was filtered off with suction. 0.6 g was obtained, M.p. 263° C. (with decomposition).

b) 2.3 g (5.07 mmol) of the above pyridine-2-carboxylic acid derivative were suspended in 200 ml of anhydrous acetonitrile/tetrahydrofuran mixture and treated successively with 0.7 g (5.5 mmol) of glycine methyl ester hydrochloride, 1.4 ml (11 mmol) of N-ethylmorpholine, 0.73 g (5.5 mmol) of 1-hydroxybenzotriazole and 1.14 g (5.5 mmol) of N,N'-dicyclohexylcarbodiimide and the mixture was stirred at 20° C. for 20 h. Insoluble matter was then filtered off, the filtrate was concentrated in vacuo, the residue was taken up in 200 ml of dichloromethane and the solution was extracted twice with saturated aqueous NaHCO₃ solution. 0.75 g of product, M.p. 275°–277° C., crystallized from the NaHCO₃ phase. A further 0.42 g of colorless crystalline product, M.p. 275°–277° C. (with foaming), was obtained from the organic phase after drying, concentration and treatment of the residue with ethyl acetate.

EXAMPLE 203

N-Methoxycarbonylmethyl-5-[((4-(benzylaminocarbonyl) phenylsulfonyl)amino)carbonyl]pyridine-2-carboxamide

EXAMPLE 204

N-Methoxycarbonylmethyl-5-[((4-((3-phenylpropyl) aminocarbonyl)phenylsulfonyl)amino)carbonyl]pyridine-2-carboxamide

EXAMPLE 205

N-Methoxycarbonylmethyl-5-[((4-((4-phenyl-n-butyl) aminocarbonyl)phenylsulfonyl)amino)carbonyl]pyridine-2-carboxamide

EXAMPLE 206

N-Methoxycarbonylmethyl-5-[((4-((2-(4-methoxyphenyl) ethyl)aminocarbonyl)phenylsulfonyl)amino) carbonyl]-pyridine-2-carboxamide

EXAMPLE 207

N-Methoxycarbonylmethyl-5-[((4-((2-(3,4-dimethoxyphenyl)ethyl) aminocarbonyl)phenylsulfonyl)amino)carbonyl]-pyridine-2-carboxamide sodium salt
  M.p. 190°–191° C. (methanol)

EXAMPLE 208

N-Methoxycarbonylmethyl-5-[((4-((2-(2-methoxyphenyl) ethyl) aminocarbonyl)phenylsulfonyl)amino)carbonyl]-pyridine-2-carboxamide

EXAMPLE 209

N-Methoxycarbonylmethyl-5-[((4-((2-(4-fluorophenyl) ethyl)aminocarbonyl)phenylsulfonyl)amino) carbonyl]-pyridine-2-carboxamide

EXAMPLE 210

N-Methoxycarbonylmethyl-5-[((4-((2-(4-chlorophenyl) ethyl) aminocarbonyl)phenylsulfonyl)amino)carbonyl]pyridine-2-carboxamide

EXAMPLE 211

N-Methoxycarbonylmethyl-5-[((4-(ethylaminocarbonyl) phenylsulfonyl)amino)carbonyl]pyridine-2-carboxamide

EXAMPLE 212

N-Methoxycarbonylmethyl-5-[((4-(n-butylaminocarbonyl) phenylsulfonyl)amino)carbonyl]pyridine-2-carboxamide
  M.p. 215°–217° C. (methanol)

EXAMPLE 213

N-Methoxycarbonylmethyl-5-[((4-(n-hexylaminocarbonyl) phenylsulfonyl)amino)carbonyl]pyridine-2-carboxamide

EXAMPLE 214

N-Methoxycarbonylmethyl-5-[((4-(N,N-di-n-butylaminocarbonyl) phenylsulfonyl)amino)carbonyl]pyridine-2-carboxamide

EXAMPLE 215

N-Methoxycarbonylmethyl-5-[((4-(cyclohexylaminocarbonyl) phenylsulfonyl)amino)carbonyl]pyridine-2-carboxamide

EXAMPLE 216

N-Methoxycarbonylmethyl-5-[((4-((2-methoxyethyl)aminocarbonyl) phenylsulfonyl)amino)carbonyl]pyridine-2-carboxamide

EXAMPLE 217

N-Methoxycarbonylmethyl-5-[((4-((2-ethoxyethyl) aminocarbonyl)phenylsulfonyl)amino)carbonyl]pyridine-2-carboxamide

EXAMPLE 218

N-Methoxycarbonylmethyl-5-[((4-((3-ethoxypropyl) aminocarbonyl)phenylsulfonyl)amino)carbonyl]pyridine-2-carboxamide
  M.p. 171°–173° C. (methanol)

EXAMPLE 219

N-Methoxycarbonylmethyl-5-[((4-((2-phenoxyethyl) aminocarbonyl)phenylsulfonyl)amino)carbonyl]pyridine-2-carboxamide

EXAMPLE 220

N-Methoxycarbonylmethyl-5-[((3-(benzylaminocarbonyl) phenylsulfonyl)amino)carbonyl]pyridine-2-carboxamide

EXAMPLE 221

N-Methoxycarbonylmethyl-5-[((3-((3-phenylpropyl) aminocarbonyl)phenylsulfonyl)amino)carbonyl]pyridine-2-carboxamide

EXAMPLE 222

N-Methoxycarbonylmethyl-5-[((3-((4-phenyl-n-butyl) aminocarbonyl)phenylsulfonyl)amino)carbonyl]pyridine-2-carboxamide

EXAMPLE 223

N-(Methylcarbonylmethyl)-5-[((3-((2-(4-methoxyphenyl) ethyl) aminocarbonyl)phenylsulfonyl)amino)carbonyl]pyridine-2-carboxamide

EXAMPLE 224

N-Methoxycarbonylmethyl-5-[((3-((2-(3-methoxyphenyl) ethyl) aminocarbonyl)phenylsulfonyl)amino)carbonyl]pyridine-2-carboxamide

EXAMPLE 225

N-Methoxycarbonylmethyl-5-[((3-((2-(2-methoxyphenyl) ethyl) aminocarbonyl)phenylsulfonyl)amino)carbonyl]pyridine-2-carboxamide

EXAMPLE 226

N-Methoxycarbonylmethyl-5-[((3-((2-(4-fluorophenyl) ethyl) aminocarbonyl)phenylsulfonyl)amino)carbonyl]pyridine-2-carboxamide

EXAMPLE 227

N-Methoxycarbonylmethyl-5-[((3-((2-(4-chlorophenyl)ethyl) aminocarbonyl)phenylsulfonyl)amino)carbonyl]pyridine-2-carboxamide

EXAMPLE 228

N-Methoxycarbonylmethyl-5-[((3-(ethylaminocarbonyl)phenylsulfonyl)amino)carbonyl]pyridine-2-carboxamide

EXAMPLE 229

N-Methoxycarbonylmethyl-5-[((3-(n-butylaminocarbonyl)phenylsulfonyl)amino)carbonyl]pyridine-2-carboxamide
M.p. 198°–200° C. (methanol)

EXAMPLE 230

N-Methoxycarbonylmethyl-5-[((3-(n-hexylaminocarbonyl)phenylsulfonyl)amino)carbonyl]pyridine-2-carboxamide

EXAMPLE 231

N-Methoxycarbonylmethyl-5-[((3-(N,N-di-n-butylaminocarbonyl)phenylsulfonyl)amino)carbonyl]pyridine-2-carboxamide

EXAMPLE 232

N-Methoxycarbonylmethyl-5-[((3 -(cyclohexylaminocarbonyl)phenylsulfonyl)amino)carbonyl]pyridine-2 -carboxamide

EXAMPLE 233

N-Methoxycarbonylmethyl-5-[((3-((2-methoxyethyl)aminocarbonyl)phenylsulfonyl)amino)carbonyl]pyridine-2-carboxamide

EXAMPLE 234

N-Methoxycarbonylmethyl-5-[((3-((2-ethoxyethyl)aminocarbonyl)phenylsulfonyl)amino)carbonyl]pyridine-2-carboxamide

EXAMPLE 235

N-Methoxycarbonylmethyl-5-[((3-((3-ethoxypropyl)aminocarbonyl)phenylsulfonyl)amino)carbonyl]pyridine-2-carboxamide

EXAMPLE 236

N-Methoxycarbonylmethyl-5-[((3-((2-phenylethyl)aminocarbonyl)phenylsulfonyl)amino)carbonyl]pyridine-2-carboxamide

EXAMPLE 237

N-Methoxycarbonylmethyl-5-[((3-((2-phenoxyethyl)amino-carbonyl)phenylsulfonyl)amino)carbonyl]pyridine-2-carboxamide

EXAMPLE 238

N-Ethoxycarbonylmethyl-5-[((4-(benzylaminocarbonyl)phenylsulfonyl)amino)carbonyl]pyridine-2-carboxamide

EXAMPLE 239

N-Ethoxycarbonylmethyl-5-[((4-((3-phenylpropyl)aminocarbonyl)phenylsulfonyl)amino)carbonyl]pyridine-2-carboxamide

EXAMPLE 240

N-Ethoxycarbonylmethyl-5-[((4-((4-phenyl-n-butyl)aminocarbonyl)phenylsulfonyl)amino)carbonyl]pyridine-2-carboxamide

EXAMPLE 241

N-Ethoxycarbonylmethyl-5-[((4-((2-(4-methoxyphenyl)-ethyl)aminocarbonyl)phenylsulfonyl)amino)carbonyl]-pyridine-2-carboxamide

EXAMPLE 242

N-Ethoxycarbonylmethyl-5-[((4-((2-(3,4-dimethoxyphenyl)ethyl)aminocarbonyl)phenylsulfonyl)amino)carbonyl]pyridine-2-carboxamide

EXAMPLE 243

N-Ethoxycarbonylmethyl-5-[((4-((2-(2-methoxyphenyl)-ethyl)aminocarbonyl)phenylsulfonyl)amino)carbonyl]pyridine-2-carboxamide

EXAMPLE 244

N-Ethoxycarbonylmethyl-5-[((4-((2-(4-fluorophenyl)ethyl)aminocarbonyl)phenylsulfonyl)amino)carbonyl]pyridine-2-carboxamide

EXAMPLE 245

N-Ethoxycarbonylmethyl-5-[((4-((2-(4-chlorophenyl)ethyl)aminocarbonyl)phenylsulfonyl)amino)carbonyl]pyridine-2-carboxamide

EXAMPLE 246

N-Ethoxycarbonylmethyl-5-[((4-(ethylaminocarbonyl)phenylsulfonyl)amino)carbonyl]pyridine-2-carboxamide

EXAMPLE 247

N-Ethoxycarbonylmethyl-5-[((4-(n-butylaminocarbonyl)phenylsulfonyl)amino)carbonyl]pyridine-2-carboxamide

EXAMPLE 248

N-Ethoxycarbonylmethyl-5-[((4-(n-hexylaminocarbonyl)phenylsulfonyl)amino)carbonyl]pyridine-2-carboxamide

EXAMPLE 249

N-Ethoxycarbonylmethyl-5-[((4-(N,N-di-n-butylaminocarbonyl)phenylsulfonyl)amino)carbonyl]pyridine-2-carboxamide

EXAMPLE 250

N-Ethoxycarbonylmethyl-5-[((4-(cyclohexylaminocarbonyl)phenylsulfonyl)amino)carbonyl]pyridine-2-carboxamide

EXAMPLE 251

N-Ethoxycarbonylmethyl-5-[((4-((2-methoxyethyl)aminocarbonyl)phenylsulfonyl)amino)carbonyl]pyridine-2-carboxamide

EXAMPLE 252

N-Ethoxycarbonylmethyl-5-[((4-((2-ethoxyethyl)aminocarbonyl)phenylsulfonyl)amino)carbonyl]pyridine-2-carboxamide

EXAMPLE 253

N-Ethoxycarbonylmethyl-5-[((4-((3-ethoxypropyl)aminocarbonyl)phenylsulfonyl)amino)carbonyl]pyridine-2-carboxamide

EXAMPLE 254

N-Ethoxycarbonylmethyl-5-[((4-((2-phenylethyl)aminocarbonyl)phenylsulfonyl)amino)carbonyl]pyridine-2-carboxamide

EXAMPLE 255

N-Ethoxycarbonylmethyl-5-[((4-((2-phenoxyethyl)aminocarbonyl)phenylsulfonyl)amino)carbonyl]pyridine-2-carboxamide

EXAMPLE 256

N-(2-Propoxycarbonylmethyl)-5-[((4-(benzylaminocarbonyl)phenylsulfonyl)amino)carbonyl]pyridine-2-carboxamide

EXAMPLE 257

N-(2-Propoxycarbonylmethyl)-5-[((4-((3-phenylpropyl)aminocarbonyl)phenylsulfonyl)amino)carbonyl]pyridine-2-carboxamide

EXAMPLE 258

N-(2-Propoxycarbonylmethyl)-5-[((4-((4-phenyl-n-butyl)aminocarbonyl)phenylsulfonyl)amino)carbonyl]pyridine-2-carboxamide

EXAMPLE 259

N-(2-Propoxycarbonylmethyl)-5-[((4-((2-(4-methoxyphenyl)ethyl)aminocarbonyl)phenylsulfonyl)amino)carbonyl]pyridine-2-carboxamide

EXAMPLE 260

N-(2-Propoxycarbonylmethyl)-5-[((4-((2-(3,4-dimethoxyphenyl)ethyl)aminocarbonyl)phenylsulfonyl)amino)carbonyl]pyridine-2-carboxamide

EXAMPLE 261

N-(2-Propoxycarbonylmethyl)-5-[((4-((2-(2-methoxyphenyl)ethyl)aminocarbonyl)phenylsulfonyl)amino)carbonyl]pyridine-2-carboxamide

EXAMPLE 262

N-(2-Propoxycarbonylmethyl)-5-[((4-((2-(4-fluorophenyl)ethyl)aminocarbonyl)phenylsulfonyl)amino)carbonyl]pyridine-2-carboxamide

EXAMPLE 263

N-(2-Propoxycarbonylmethyl)-5-[((4-((2-(4-chlorophenyl)ethyl)aminocarbonyl)phenylsulfonyl)amino)carbonyl]pyridine-2-carboxamide

EXAMPLE 264

N-(2-Propoxycarbonylmethyl)-5-[((4-(ethylaminocarbonyl)phenylsulfonyl)amino)carbonyl]pyridine-2-carboxamide

EXAMPLE 265

N-(2-Propoxycarbonylmethyl)-5-[((4-(n-butylaminocarbonyl)phenylsulfonyl)amino)carbonyl]pyridine-2-carboxamide

EXAMPLE 266

N-(2-Propoxycarbonylmethyl)-5-[((4-(n-hexylaminocarbonyl)phenylsulfonyl)amino)carbonyl]pyridine-2-carboxamide

EXAMPLE 267

N-(2-Propoxycarbonylmethyl)-5-[((4-(N,N-di-n-butylaminocarbonyl)phenylsulfonyl)amino)carbonyl]pyridine-2-carboxamide

EXAMPLE 268

N-(2-Propoxycarbonylmethyl)-5-[((4-(cyclohexylaminocarbonyl)phenylsulfonyl)amino)carbonyl]pyridine-2-carboxamide

EXAMPLE 269

N-(2-Propoxycarbonylmethyl)-5-[((4-((2-methoxyethyl)aminocarbonyl)phenylsulfonyl)amino)carbonyl]pyridine-2-carboxamide

EXAMPLE 270

N-(2-Propoxycarbonylmethyl)-5-[((4-((2-ethoxyethyl)aminocarbonyl)phenylsulfonyl)amino)carbonyl]pyridine-2-carboxamide

EXAMPLE 271

N-(2-Propoxycarbonylmethyl)-5-[((4-((3-ethoxypropyl)aminocarbonyl)phenylsulfonyl)amino)carbonyl]pyridine-2-carboxamide

EXAMPLE 272

N-(2-Propoxycarbonylmethyl)-5-[((4-((2-phenylethyl)aminocarbonyl)phenylsulfonyl)amino)carbonyl]pyridine-2-carboxamide

EXAMPLE 273

N-(2-Propoxycarbonylmethyl)-5-[((4-((2-phenoxyethyl)aminocarbonyl)phenylsulfonyl)amino)carbonyl]pyridine-2-carboxamide

EXAMPLE 274

N-Benzyloxycarbonylmethyl-5-[((4-(benzylaminocarbonyl)phenylsulfonyl)amino)carbonyl]pyridine-2-carboxamide

EXAMPLE 275

N-Benzyloxycarbonylmethyl-5-[((4-((3-phenylpropyl)aminocarbonyl)phenylsulfonyl)amino)carbonyl]pyridine-2-carboxamide

EXAMPLE 276

N-Benzyloxycarbonylmethyl-5-[((4-((4-phenyl-n-butyl)aminocarbonyl)phenylsulfonyl)amino)carbonyl]pyridine-2-carboxamide

EXAMPLE 277

N-Benzyloxycarbonylmethyl-5-[((4-((2-(4-methoxyphenyl)ethyl)aminocarbonyl)phenylsulfonyl)amino)carbonyl]pyridine-2-carboxamide

EXAMPLE 278

N-Benzyloxycarbonylmethyl-5-[((4-((2-(3,4-dimethoxyphenyl)ethyl)aminocarbonyl)phenylsulfonyl)amino)carbonyl]pyridine-2-carboxamide

EXAMPLE 279

N-Benzyloxycarbonylmethyl-5-[((4-((2-(2-methoxyphenyl)ethyl)aminocarbonyl)phenylsulfonyl)amino)carbonyl]pyridine-2-carboxamide

EXAMPLE 280

N-Benzyloxycarbonylmethyl-5-[((4-((2-(4-fluorophenyl)ethyl)aminocarbonyl)phenylsulfonyl)amino)carbonyl]pyridine-2-carboxamide

EXAMPLE 281

N-Benzyloxycarbonylmethyl-5-[((4-((2-(4-chlorophenyl)ethyl)aminocarbonyl)phenylsulfonyl)amino)carbonyl]pyridine-2-carboxamide

EXAMPLE 282

N-Benzyloxycarbonylmethyl-5-[((4-(ethylaminocarbonyl)phenylsulfonyl)amino)carbonyl]pyridine-2-carboxamide

EXAMPLE 283

N-Benzyloxycarbonylmethyl-5-[((4-(n-butylaminocarbonyl)phenylsulfonyl)amino)carbonyl]pyridine-2-carboxamide

EXAMPLE 284

N-Benzyloxycarbonylmethyl-5-[((4-(n-hexylaminocarbonyl)phenylsulfonyl)amino)carbonyl]pyridine-2-carboxamide

EXAMPLE 285

N-Benzyloxycarbonylmethyl-5-[((4-(N,N-di-n-butylaminocarbonyl)phenylsulfonyl)amino)carbonyl]pyridine-2-carboxamide

EXAMPLE 286

N-Benzyloxycarbonylmethyl-5-[((4-(cyclohexylaminocarbonyl)phenylsulfonyl)amino)carbonyl]pyridine-2-carboxamide

EXAMPLE 287

N-Benzyloxycarbonylmethyl-5-[((4-((2-methoxyethyl)aminocarbonyl)phenylsulfonyl)amino)carbonyl]pyridine-2-carboxamide

EXAMPLE 288

N-Benzyloxycarbonylmethyl-5-[((4-((2-ethoxyethyl)aminocarbonyl)phenylsulfonyl)amino)carbonyl]pyridine-2-carboxamide

EXAMPLE 289

N-Benzyloxycarbonylmethyl-5-[((4-((3-ethoxypropyl)aminocarbonyl)phenylsulfonyl)amino)carbonyl]pyridine-2-carboxamide

EXAMPLE 290

N-Benzyloxycarbonylmethyl-5-[((4-((2-phenylethyl)aminocarbonyl)phenylsulfonyl)amino)carbonyl]pyridine-2-carboxamide

EXAMPLE 291

N-Benzyloxycarbonylmethyl-5-[((4-((2-phenoxyethyl)aminocarbonyl)phenylsulfonyl)amino)carbonyl]pyridine-2-carboxamide

EXAMPLE 292

N-Carboxymethyl-5-[((3-(n-butylaminocarbonyl)phenylsulfonyl)amino)carbonyl]pyridine-2-carboxamide M.p. 220°–220° C. (from aqueous hydrochloric acid)

EXAMPLE 293

N-Carboxymethyl-5-[((4-((3-phenylpropyl)aminocarbonyl)phenylsulfonyl)amino)carbonyl]pyridine-2-carboxamide

EXAMPLE 294

N-Carboxymethyl-5-[((4-((4-phenyl-n-butyl)aminocarbonyl)phenylsulfonyl)amino)carbonyl]pyridine-2-carboxamide

EXAMPLE 295

N-Carboxymethyl-5-[((4-((2-(4-methoxyphenyl)ethyl)aminocarbonyl)phenylsulfonyl)amino)carbonyl]pyridine-2-carboxamide

EXAMPLE 296

N-Carboxymethyl-5-[((4-((2-(3,4-dimethoxyphenyl)ethyl)aminocarbonyl)phenylsulfonyl)amino)carbonyl]pyridine-2-carboxamide M.p. 190° C. (sintering), 201°–203° C. (from aqueous hydrochloric acid)

EXAMPLE 297

N-Carboxymethyl-5-[((4-((2-(2-methoxyphenyl)ethyl)aminocarbonyl)phenylsulfonyl)amino)carbonyl]pyridine-2-carboxamide

EXAMPLE 298

N-2-Carboxymethyl-5-[((4-((2-(4-fluorophenyl)ethyl)aminocarbonyl)phenylsulfonyl)amino)carbonyl]pyridine-2-carboxamide

EXAMPLE 299

N-Carboxymethyl-5-[((4-((2-(4-chlorophenyl)ethyl)aminocarbonyl)phenylsulfonyl)amino)carbonly]pyridine-2-carboxamide

EXAMPLE 300

N-Carboxymethyl-5-[((4-(ethylaminocarbonyl)phenylsulfonyl)amino)carbonyl]pyridine-2-carboxamide

EXAMPLE 301

N-Carboxymethyl-5-[((4-(n-butylaminocarbonyl)phenylsulfonyl)amino)carbonyl[pyridine-2-carboxamide
M.p. 244°–247° C. (decomposition, from aqueous hydrochloric acid)

EXAMPLE 302

N-Carboxymethyl-5-[((4(n-hexylaminocarbonyl)phenylsulfonyl)amino)carbonyl]pyridine-2-carbonamide

EXAMPLE 303

N-Carboxymethyl-5-[((4-(N,N-di-n-butylaminocarbonyl)phenylsulfony)amino)carbonyl]pyridine-2-carboxamide

EXAMPLE 304

N-Carboxymethyl-5-[((4-(cyclohexylaminocarbonyl)phenylsulfony)amino)carbonyl]pyridine-2-carboxamide

EXAMPLE 305

N-Carboxymethyl-5-[((4-((2-methoxyethyl)aminocarbonyl)phenylsulfonyl)amino)carbonyl]pyridine-2-carboxamide

EXAMPLE 306

N-Carboxymethyl-5-[((4-((2-ethoxyethyl)aminocarbonyl)phenylsulfonyl)amino)carbonyl]pyridine-2-carboxamide

EXAMPLE 307

N-Carboxymethyl-5-[((4-((3-ethoxypropyl)aminocarbonyl)phenylsulfony)amino)carbonyl]pyridine-2-carboxamide
M.p. 109° C. (from tetrahydrofuran/aqueous hydrochloric acid)

EXAMPLE 308

N-Carboxymethyl-5-[((4-((2-phenylethyl)aminocarbonyl)phenylsulfonyl)amino)carbonyl]pyridine-2-carboxamide
M.p. 263°–265° C. (from aqueous hydrochloric acid

EXAMPLE 309

N-Carboxymethyl-5-[((4-((2-phenoxyethyl)aminocarbonyl)phenylsulfonyl)amino)carbonyl]pyridine-2-carboxamide

EXAMPLE 310

N-(2-Hydroxyethyl)-5-[((2-chloro-4-((2-phenoxyethyl)aminocarbonyl)phenylsulfonyl)amino)carbonyl]pyridine-2-carboxamide

EXAMPLE 311

N-(2-Hydroxyethyl)-5-[((2-chloro-4-((3-ethoxypropyl)aminocarbonyl)phenylsulfonyl)amino)carbonyl]pyridine-2-carboxamide

EXAMPLE 312

N-(2-Hydroxyethyl)-5-[((4-chloro-3-((3-ethoxypropyl)aminocarbonyl)phenylsulfonyl)amino)carbonyl]pyridine-2-carboxamide

EXAMPLE 313

N-(2-Hydroxyethyl)-5-[((4-chloro-3-((2-phenoxyethyl)aminocarbonyl)phenylsulfonyl)amino)carbonyl]pyridine-2-carboxamide

EXAMPLE 314

N-(2-Methoxyethyl)-5-[((2-chloro-4-((2-phenoxyethyl)aminocarbonyl)phenylsulfonyl)amino)carbonyl]pyridine-2-carboxamide

EXAMPLE 315

N-(2-Methoxyethyl)-5-[((2-chloro-4-((3-ethoxypropyl)aminocarbonyl)phenylsulfonyl)amino)carbonyl]pyridine-2-carboxamide

EXAMPLE 316

N-(2-Methoxyethyl)-5-[((4-chloro-3-((3-ethoxypropyl)aminocarbonyl)phenylsulfonyl)amino)carbonyl]pyridine-2-carboxamide

EXAMPLE 317

N-(2-Methoxyethyl)-5-[((4-chloro-3((2-phenoxyethyl)aminocarbonyl)phenylsulfonyl)amino)carbonyl]pyridine-2-carboxamide

EXAMPLE 318

N-(2-Ethoxyethyl)-5[((2-chloro-4-((2-phenoxyethyl)aminocarbonyl)phenylsulfonyl)amino)carbonyl]pyridine-2-carboxamide

EXAMPLE 319

N-(2-Ethoxyethyl)-5-[((2-chloro-4-((3-ethoxypropyl)aminocarbonyl)phenylsulfonyl)amino)carbonyl]pyridine-2-carboxamide

EXAMPLE 320

N-(2-Ethoxyethyl)-5-[((4-chloro-3-((3-ethoxypropyl)aminocarbonyl)phenylsulfonyl)amino)carbonyl]pyridine-2-carboxamide

EXAMPLE 321

N-(2-Ethoxyethyl)-5-[((4-chloro-3-((2-phenoxyethyl)aminocarbonyl)phenylsulfonyl)amino)carbonyl]pyridine-2-carboxamide

EXAMPLE 322

N-(2-(2-Propyl)oxyethyl)-5-[((2-chloro-4-((2-phenoxyethyl) aminocarbonyl)phenylsulfonyl)amino)carbonyl]pyridine-2-carboxamide

EXAMPLE 323

N-(2(2-Propyl)oxyethyl)-5-((2-chloro-4-((3-ethoxypropyl) aminocarbonyl)phenylsulfonyl)amino)carbonyl]pyridine-2-carboxamide

EXAMPLE 324

N-Methoxycarbonylemthyl-5-[((2-chloro-4-((2-phenoxyethyl)aminocarbonyl)phenylsulfonyl)amino)carbonyl]pyridine-2-carboxamide

EXAMPLE 325

N-Methoxycarbonylmethyl-5-[((2-chloro-4-((3-ethoxypropyl)aminocarbonyl)phenylsulfonyl)amino)carbonyl]pyridine-2-carboxamide

EXAMPLE 326

N-Methoxycarbonylmethyl-5-[((4-chloro-3-((3-ethoxypropyl)aminocarbonyl)phenylsulfonyl)amino)carbonyl]pyridine-2-carboxamide

EXAMPLE 327

N-Methoxycarbonylmethyl-5-[((4-chloro-3-((2-phenoxyethyl)aminocarbonyl)phenylsulfonyl)amino)carbonyl]pyridine-2-carboxamide

EXAMPLE 328

N-(2-Propoxycarbonylmethyl)-5-[((2-chloro-4-((2-phenoxyethyl)aminocarbonyl)phenylsulfonyl)amino)carbonyl]pyridine-2-carboxamide

EXAMPLE 329

N-(2-Propoxycarbonylmethyl)-5-[((2-chloro-4-((3-ethoxypropyl)aminocarbonyl)phenylsulfonyl)amino)carbonyl]pyridine-2-carboxamide

EXAMPLE 330

N-(3-phentoxycarbonylmethyl)-5-[((2-chloro-4-((2-phenoxyethyl)aminocarbonyl)phenylsulfonyl)amino)carbonyl]pyridine-2-carboxamide

EXAMPLE 331

N-(3-Pentoxycarbonylmethyl)-5-[((2-chloro-4-((3-ethoxypropyl)aminocarbonyl)phenylsulfonyl)amino)carbonyl]pyridine-2-carboxamide

EXAMPLE 332

N-(2-Hydroxyethyl)-5-[((4-(2-((2-chloro-5-methoxybenzoyl)amino)ethyl)phenylsulfonyl)amino)carbonyl]pyridine-2-carboxamide a) Methyl 5-[((4-(2-((2-chloro-5-methoxybenzoyl)amino)ethyl)phenylsulfonyl)amino)carbonyl]pyridine-2-carboxylate The 2-methoxycarbonylpyridine-5-carbonyl chloride prepared from 4.0 g (22 mmol) of 2-methoxycarbonylpyridine-5-carboxylic acid, as described in Example 1 c), was added in 50 ml of anhydrous 1,4-dioxane at 40° C. to the reaction mixture of 7.4 g (20 mmol) of 2-(((2-chloro-5-methoxybenzoyl)amino)ethyl)benzenesulfonamide (prepared from 4-(2-aminoethyl)benzenesulfonamide and 2-chloro-5-methoxybenzoic acid) and 2.3 g (20 mmol) of potassium tert-butoxide in 150 ml of anhydrous 1,4-dioxane (had been stirred at 50° C. for 15 min to form the sulfonamide sodium salt).

The reaction mixture was stirred at 60° C. for 90 min, then under reflux for 2 h, the solvent was distilled off in vacuo, the residue was treated with water and the mixture was brought to pH 1–2 using aqueous HCl and extracted with dichloromethane. The residue was treated with hot ethyl acetate, filtered off with suction and washed with ethyl acetate. The crude product thus obtained (2.8 g) was treated with 100 ml of cold water, then with 100 ml of hot water, and the colorless crystalline product was filtered off with suction. 2.6 g were obtained, M.p. 187°–190° C.

b) 0.85 g (1.6 mmol) of the above methyl ester was stirred at 80° to 90° C. for 1 h in 150 ml of 2-aminoethanol. After cooling, excess reagent was distilled off in vacuo, the residue was dissolved in 20–30 ml of water, the solution was brought to pH 1 with conc. aqueous HCl, and the crystalline product was filtered off with suction, washed with water, treated with hot ethyl acetate and again filtered off with suction. 0.65 g of the title compound was obtained, M.p. 135°–137° C.

EXAMPLE 333

N-(2-Hydroxyethyl)-5-[((4-(2-(acetylamino)ethyl)phenylsulfonyl)amino)carbonyl]pyridine-2-carboxamide

EXAMPLE 334

N-(2-Hydroxyethyl)-5-[((4-(2-(n-butanoylamino)ethyl)phenylsulfonyl)amino)carbonyl]pyridine-2-carboxamide

EXAMPLE 335

N-(2-Hydroxyethyl)-5-[((4-(2-(benzoylamino)ethyl)phenylsulfonyl)amino)carbonyl]pyridine-2-carboxamide

EXAMPLE 336

N-(2-Hydroxyethyl)-5-[((4-(2-((4-chlorobenzoyl)amino)ethyl)phenylsulfonyl)amino)carbonyl]pyridine-2-carboxamide

EXAMPLE 337

N-(2-Hydroxyethyl)-5-[((4-(2((5chloro-2-methoxybenzoyl)amino)ethyl)phenylsulfonyl)amino)carbonyl]pyridine-2-carboxamide

EXAMPLE 338

N-(2-Hydroxyethyl)-5-[((4-(2((3-3,4-dimethoxyphenylpropionly)amino)ethyl)phenylsulfonyl)amino)carbonyl]pyridine-2-carboxamide M.p. 176°–177° C. (water)

EXAMPLE 339

N-(2-Hydroxyethyl)-5-[((4-(2-((2-phenylacetyl)amino)ethyl)phenylsulfonyl)amino)carbonyl]pyridine-2-carboxamide

EXAMPLE 340

N-(2-Hydroxyethyl)-5-[((4-(2-((phenoxyacetyl)amino)ethyl)phenylsulfonyl)amino)carbonyl]pyridine-2-carboxamide M.p. 155°–156° C. (water)

EXAMPLE 341

N-(2-Hydroxyethyl)-5-[((4-(2-((4-fluorobenzoyl)amino)ethyl)phenylsufonyl)amino)carbonyl]pyridine-2-carboxamide

EXAMPLE 342

N-(2-Hydroxyethyl)-5-[((4-(2-((4-methylpentanoyl)amino)ethyl)phenylsulfonyl)amino)carbonyl]pyridine-2-carboxamide M.P. 179°–181° C. (water)

EXAMPLE 343

N-(2-Hydroxyethyl)-5-[((4-(2-((cyclohexanoyl)amino)ethyl)phenylsulfonyl)amino)carbonyl]pyridine-2-carboxamide

EXAMPLE 344

N-(2-Hydroxyethyl)-5-[((4-(2-((cyclohexylexylacetyl)amino)ethyl)phenylsulfonyl)amino)carbonyl]pyridine-2-carboxamide

EXAMPLE 345

N-(2-Hydroxyethyl)-5-[((4-(2-((2-methylpropionyl)amino)ethyl)phenylsulfonyl)amino)carbonyl]pyridine-2-carboxamide

EXAMPLE 346

N-(2-Hydroxyethyl)-5-[((3-(2-((2-chloro-5-methoxybenzoyl)amino)ethyl)phenylsulfonyl)amino)carbonyl]pyridine-2-carboxamide

EXAMPLE 347

N-(2-Hydroxyethyl)-5-[((3-(2-(acetylamino)ethyl)phenylsulfonyl)amino)carbonyl]pyridine-2-carboxamide

EXAMPLE 348

N-(2-Hydroxyethyl)-5-[((3-(2-(n-butanoylamino)ethyl)phenylsulfonyl)amino)carboxyl]pyridine-2-carboxamide

EXAMPLE 349

N-(2-Hydroxyethyl)-5-[((3-(2-(benzoylamino)ethyl)phenylsulfonyl)amino)carbonyl]pyridine-2-carboxamide

EXAMPLE 350

N-(2-Hydroxyethyl)-5-[((3-(2-((4-chlorobenzoyl)amino)ethyl)phenylsulfonyl)amino)carbonyl]pyridine-2-carboxamide

EXAMPLE 351

N-(2-Hydroxyethyl)-5-[((3-(2-((5-chloro-2-methoxybenzoyl)amino)ethyl)phenylsulfonyl)amino)carbonyl]pyridine-2-carboxamide

EXAMPLE 352

N-(2-Hydroxyethyl)-5-[((3-(2-((3-phenyl-n-propionyl)amino)ethyl)phenylsulfonyl)amino)carbonyl]pyridine-2-carboxamide

EXAMPLE 353

N-(2-Hydroxyethyl)-5-[((3-(2-((2-phenylacetyl)amino)ethyl)phenylsulfonyl)amino)carbonyl]pyridine-2-carboxamide

EXAMPLE 354

N-(2-Hydroxyethyl)-5-[((3-(2-((phenoxyacetyl)amino)ethyl)phenylsulfonyl)amino)carbonyl]pyridine-2-carboxamide

EXAMPLE 355

N-(2-Hydroxyethyl)-5-[((3-(2-((4-fluorobenzoyl)amino)ethyl)phenylsulfonyl)amino)carbonyl]pyridine-2-carboxamide

EXAMPLE 356

N-(2-Hydroxyethyl)-5-[((3-(2-((4-ethoxybenzoyl)amino)ethyl)phenylsulfonyl)amino)carbonyl]pyridine-2-carboxamide

EXAMPLE 357

N-(2-Hydroxyethyl)-5-[((3-(2-((cyclohexanoyl)amino)ethyl)phenylsulfonyl)amino)carbonyl]pyridine-2-carboxamide

EXAMPLE 358

N-(2-Hydroxyethyl)-5-[((3-(2-((cyclohexylacetyl)amino)ethyl)phenylsulfonyl)amino)carbonyl]pyridine-2-carboxamide

EXAMPLE 359

N-(2-Hydroxyethyl)-5-[((3-(2-((2-methylpropionyl)amino)ethyl)phenylsulfonyl)amino)carbonyl]pyridine-2-carboxamide

EXAMPLE 360

N-(2-Methoxyethyl)-5-[((4-(2-((2-chloro-5-methoxybenzoyl)amino)ethyl)phenylsulfonyl)amino)carbonyl]pyridine-2-carboxamide

EXAMPLE 361

N-(2-Methoxyethyl)-5-[((4-(2-(acetylamino)ethyl)phenylsulfonyl)amino)carbonyl]pyridine-2-carboxamide

EXAMPLE 362

N-(2-Methoxyethyl)-5-[((4-(2-(n-butanoylamino)ethyl)phenylsulfonyl)amino)carbonyl]pyridine-2-carboxamide

EXAMPLE 363

N-(2-Methoxyethyl)-5-[((4-(2-(benzoylamino)ethyl)phenylsulfonyl)amino)carbonyl]pyridine-2-carboxamide

EXAMPLE 364

N-(2-Methoxyethyl)-5-[((4-(2-((4-chlorobenzoyl)amino)ethyl)phenylsulfonyl)amino)carbonyl]pyridine-2-carboxamide

EXAMPLE 365

N-(2-Methoxyethyl)-5-[((4-(2-((5-chloro-2-methoxybenzoyl)amino)ethyl)phenylsulfonyl)amino)carbonyl]pyridine-2-carboxamide

EXAMPLE 366

N-(2-Methoxyethyl)-5-[((4-(2-((3-(3,4-dimethoxyphenyl)propionyl)amino)ethyl)phenylsulfonyl)amino)carbonyl]pyridine-2-carboxamide M.p. 87°–89° C. (amorphous, diisopropyl ether)

EXAMPLE 367

N-(2-Methoxyethyl)-5-[((4-(2-((2-phenylacetyl)amino)ethyl)phenylsulfonyl)amino)carbonyl]pyridine-2-carboxamide

EXAMPLE 368

N-(2-Methoxyethyl)-5-[((4-(2-((phenoxyacetyl)amino)ethyl)phenylsulfonyl)amino)carbonyl]pyridine-2-carboxamide

EXAMPLE 369

N-(2-Methoxyethyl)-5-[((4-(2-((4-fluorobenzoyl)amino)ethyl)phenylsulfonyl)amino)carbonyl]pyridine-2-carboxamide

EXAMPLE 370

N-(2-Methoxyethyl)-5-[((4-(2-((4-methylpentanoyl)amino)ethyl)phenylsulfonyl)amino)carbonyl]pyridine-2-carboxamide M.p. 154°–157° C. (water)

EXAMPLE 371

N-(2-Methoxyethyl)-5-[((4-(2-((cyclohexanoyl)amino)ethyl)phenylsulfonyl)amino)carbonyl]pyridine-2-carboxamide

EXAMPLE 372

N-(2-Methoxyethyl)-5-[((4-(2-((cyclohexylacetyl)amino)ethyl)phenylsulfonyl)amino)carbonyl]pyridine-2-carboxamide

EXAMPLE 373

N-(2-Methoxyethyl)-5-[((4-(2-((2-methylpropionyl)amino)ethyl)phenylsulfonyl)amino)carbonyl]pyridine-2-carboxamide

EXAMPLE 374

N-(2-Methoxyethyl)-5-[((3-(2-((2-chloro-5-methoxybenzoyl)amino)ethyl)phenylsulfonyl)amino)carbonyl]pyridine-2-carboxamide

EXAMPLE 375

N-(2-Methoxyethyl)-5-[((3-(2-(acetylamino)ethyl)phenylsulfonyl)amino)carbonyl]pyridine-2-carboxamide

EXAMPLE 376

N-(2-Methoxyethyl)-5-[((3-(2-(n-butanoylamino)ethyl)phenylsulfonyl)amino)carbonyl]pyridine-2-carboxamide

EXAMPLE 377

N-(2-Methoxyethyl)-5-[((3-(2-(benzoylamino)ethyl)phenylsulfonyl)amino)carbonyl]pyridine-2-carboxamide

EXAMPLE 378

N-(2-Methoxyethyl)-5-[((3-(2-((4-chlorobenzoyl)amino)ethyl)phenylsulfonyl)amino)carbonyl]pyridine-2-carboxamide

EXAMPLE 379

N-(2-Methoxyethyl)-5-[((3-(2-((5-chloro-2-methoxybenzoyl)amino)ethyl)phenylsulfonyl)amino)carbonyl]pyridine-2-carboxamide

EXAMPLE 380

N-(2-Methoxyethyl)-5-[((3-(2-((3-phenyl-n-propionyl)amino)ethyl)phenylsulfonyl)amino)carbonyl]pyridine-2-carboxamide

EXAMPLE 381

N-(2-Methoxyethyl)-5-[((3-(2-((2-phenylacetyl)amino)ethyl)phenylsulfonyl)amino)carbonyl]pyridine-2-carboxamide

EXAMPLE 382

N-(2-Methoxyethyl)-5-[((3-(2-((phenoxyacetyl)amino)ethyl)phenylsulfonyl)amino)carbonyl]pyridine-2-carboxamide

EXAMPLE 383

N-(2-Methoxyethyl)-5-[((3-(2-((4-fluorobenzoyl)amino)ethyl)phenylsulfonyl)amino)carbonyl]pyridine-2-carboxamide

EXAMPLE 384

N-(2-Methoxyethyl)-5-[((3-(2-((4-ethoxybenzoyl)amino)ethyl)phenylsulfonyl)amino)carbonyl]pyridine-2-carboxamide

EXAMPLE 385

N-(2-Methoxyethyl)-5-[((3-(2-((cyclohexanoyl)amino)ethyl)phenylsulfonyl)amino)carbonyl]pyridine-2-carboxamide

EXAMPLE 386

N-(2-Methoxyethyl)-5-[((3-(2-((cyclohexylacetyl)amino)ethyl)phenylsulfonyl)amino)carbonyl]pyridine-2-carboxamide

EXAMPLE 387

N-(2-Methoxyethyl)-5-[((3-(2-((2-methylpropionyl)amino)ethyl)phenylsulfonyl)amino)carbonyl]pyridine-2-carboxamide

EXAMPLE 388

N-(2-Methoxyethyl)-5-[((4-(2-((2-chloro-5-methoxybenzoyl)amino)ethyl)phenylsulfonyl)amino)carbonyl]pyridine-2-carboxamide

EXAMPLE 389

N-(2-Methoxyethyl)-5-[((4-(2-(acetylamino)ethyl)phenylsulfonyl)amino)carbonyl]pyridine-2-carboxamide

EXAMPLE 390

N-(2-Methoxyethyl)-5-[((4-(2-(n-butanoylamino)ethyl)phenylsulfonyl)amino)carbonyl]pyridine-2-carboxamide

EXAMPLE 391

N-(2-Methoxyethyl)-5-[((4-(2-(benzoylamino)ethyl)phenylsulfonyl)amino)carbonyl]pyridine-2-carboxamide

EXAMPLE 392

N-(2-Methoxyethyl)-5-[((4-(2-((4-chlorobenzoyl)amino)ethyl)phenylsulfonyl)amino)carbonyl]pyridine-2-carboxamide

EXAMPLE 393

N-(2-Methoxyethyl)-5-[((4-(2-((5-chloro-2-methoxybenzoyl)amino)ethyl)phenysulfonyl)amino)carbonyl]pyridine-2-carboxamide

EXAMPLE 394

N-(2-Methoxyethyl)-5-[((4-(2-((3-phenyl-n-propionyl)amino)ethyl)phenylsulfonyl)amino)carbonyl]pyridine-2-carboxamide

EXAMPLE 395

N-(2-Methoxyethyl)-5-[((4-(2-((2-phenylacetyl)amino)ethyl)phenylsulfonyl)amino)carbonyl]pyridine-2-carboxamide

EXAMPLE 396

N-(2-Methoxyethyl)-5-[((4-(2-((phenoxyacetyl)amino)ethyl)phenylsulfonyl)amino)carbonyl]pyridine-2-carboxamide

EXAMPLE 397

N-(2-Methoxyethyl)-5-[((4-(2-((4-fluorobenzoyl)amino)ethyl)phenylsulfonyl)amino)carbonyl]pyridine-2-carboxamide

EXAMPLE 398

N-(2-Methoxyethyl)-5-[((4-(2-((4-ethoxybenzoyl)amino)ethyl)phenylsulfonyl)amino)carbonyl]pyridine-2-carboxamide

EXAMPLE 399

N-(2-Methoxyethyl)-5-[((4-(2-((cyclohexanoyl)amino)ethyl)phenylsulfonyl)amino)carbonyl]pyridine-2-carboxamide

EXAMPLE 400

N-(2-Methoxyethyl)-5-[((4-(2-((cyclohexylacetyl)amino)ethyl)phenylsulfonyl)amino)carbonyl]pyridine-2-carboxamide

EXAMPLE 401

N-(2-Methoxyethyl)-5-[((4-(2-((2-methylpropionyl)amino)ethyl)phenylsulfonyl)amino)carbonyl]pyridine-2-carboxamide

EXAMPLE 402

N-(2-Acetoxyethyl)-5-[((4-(2-((2-chloro-5-methoxybenzoyl)amino)ethyl)phenylsulfonyl)amino)carbonyl]pyridine-2-carboxamide

EXAMPLE 403

N-(2-Acetoxyethyl)-5-[((4-(2-(acetylamino)ethyl)phenylsulfonyl)amino)carbonyl]pyridine-2-carboxamide

EXAMPLE 404

N-(2-Acetoxyethyl)-5-[((4-(2-(n-butanoylamino)ethyl)phenylsulfonyl)amino)carbonyl]pyridine-2-carboxamide

EXAMPLE 405

N-(2-Acetoxyethyl)-5-[((4-(2-(benzoylamino)ethyl)phenylsulfonyl)amino)carbonyl]pyridine-2-carboxamide

EXAMPLE 406

N-(2-Acetoxyethyl)-5-[((4-(2-((4-chlorobenzoyl)amino)ethyl)phenylsulfonyl)amino)carbonyl]pyridine-2-carboxamide

EXAMPLE 407

N-(2-Acetoxyethyl)-5-[((4-(2-((5-chloro-2-methoxybenzoyl)amino)ethyl)phenylsulfonyl)amino)carbonyl]pyridine-2-carboxamide

EXAMPLE 408

N-(2-Acetoxyethyl)-5-[((4-(2-((3-phenyl-n-propionyl)amino)ethyl)phenylsulfonyl)amino)carbonyl]pyridine-2-carboxamide

EXAMPLE 409

N-(2-Acetoxyethyl)-5-[((4-(2-((2-phenylacetyl)amino)ethyl)phenylsulfonyl)amino)carbonyl]pyridine-2-carboxamide

EXAMPLE 410

N-(2-Acetoxyethyl)-5-[((4-(2-((phenoxyacetyl)amino)ethyl)phenylsulfonyl)amino)carbonyl]pyridine-2-carboxamide

EXAMPLE 411

N-(2-Acetoxyethyl)-5-[((4-(2-((4-fluorobenzoyl)amino)ethyl)phenylsulfonyl)amino)carbonyl]pyridine-2-carboxamide

EXAMPLE 412

N-(2-Acetoxyethyl)-5-[((4-(2-((4-ethoxybenzoyl)amino)ethyl)phenylsulfonyl)amino)carbonyl]pyridine-2-carboxamide

EXAMPLE 413

N-(2-Acetoxyethyl)-5-[((4-(2-((cyclohexanoyl)amino)ethyl)phenylsulfonyl)amino)carbonyl]pyridine-2-carboxamide

EXAMPLE 414

N-(2-Acetoxyethyl)-5-[((4-(2-((cyclohexylacetyl)amino)ethyl)phenylsulfonyl)amino)carbonyl]pyridine-2-carboxamide

EXAMPLE 415

N-(2-Acetoxyethyl)-5-[((4-(2-((2-methylpropionyl)amino)ethyl)phenylsulfonyl)amino)carbonyl]pyridine-2-carboxamide

EXAMPLE 416

N-(2-(2-Methylbenzoyl)oxyethyl)-5-[((4-(2-((2-chloro-5-methoxybenzoyl)amino)ethyl)phenylsulfonyl)amino)carbonyl]pyridine-2-carboxamide

EXAMPLE 417

N-(2-(2-Methylbenzoyl)oxyethyl)-5-[((4-(2-(acetylamino)ethyl)phenylsulfonyl)amino)carbonyl]pyridine-2-carboxamide

EXAMPLE 418

N-(2-(2-Methylbenzoyl)oxyethyl)-5-[((4-(2-(n-butanoylamino)ethyl)phenylsulfonyl)amino)carbonyl]pyridine-2-carboxamide

EXAMPLE 419

N-(2-(2-Methylbenzoyl)oxyethyl)-5-[((4-(2-(benzoylamino)ethyl)phenylsulfonyl)amino)carbonyl]pyridine-2-carboxamide

EXAMPLE 420

N-(2-(2-Methylbenzoyl)oxyethyl)-5-[((4-(2-((4-chlorobenzoyl)amino)ethyl)phenylsulfonyl)amino)carbonyl]pyridine-2-carboxamide

EXAMPLE 421

N-(2-(2-Methylbenzoyl)oxyethyl)-5-[((4-(2-((5-chloro-2-methoxybenzoyl)amino)ethyl)phenylsulfonyl)amino)carbonyl]pyridine-2-carboxamide

EXAMPLE 422

N-(2-(2-Methylbenzoyl)oxyethyl)-5-[((4-(2-((3-phenyl-n-propionyl)amino)ethyl)phenylsulfonyl)amino)carbonyl]pyridine-2-carboxamide

EXAMPLE 423

N-(2-(2-Methylpropionyl)oxyethyl)-5-[((4-(2-((2-phenylacetyl)amino)ethyl)phenylsulfonyl)amino)carbonyl]pyridine-2-carboxamide

EXAMPLE 424

N-(2-(2-Methylpropionyl)oxyethyl)-5-[((4-(2-((phenoxyacetyl)amino)ethyl)phenylsulfonyl)amino)carbonyl]pyridine-2-carboxamide

EXAMPLE 425

N-(2-(2-Methylpropionyl)oxyethyl)-5-[((4-(2-((4-fluorobenzoyl)amino)ethyl)phenylsulfonyl)amino)carbonyl]pyridine-2-carboxamide

EXAMPLE 426

N-(2-(2-Methylpropionyl)oxyethyl)-5-[((4-(2-((4-ethoxybenzoyl)amino)ethyl)phenylsulfonyl)amino)carbonyl]pyridine-2-carboxamide

EXAMPLE 427

N-(2-(2-Methylpropionyl)oxyethyl)-5-[((4-(2-((cyclohexanoyl)amino)ethyl)phenylsulfonyl)amino)carbonyl]pyridine-2-carboxamide

EXAMPLE 428

N-(2-(2-Methylpropionyl)oxyethyl)-5-[((4-(2-((cyclohexylacetyl)amino)ethyl)phenylsulfonyl)amino)carbonyl]pyridine-2-carboxamide

EXAMPLE 429

N-(2-(2-Methylpropionyl)oxyethyl)-5-[((4-(2-((2-methylpropionyl)amino)ethyl)phenylsulfonyl)amino)carbonyl]pyridine-2-carboxamide

EXAMPLE 430

N-(2-Hydroxyethyl)-5-[((4-(2-((2-ethylbutanoyl)amino)ethyl)phenylsulfonyl)amino)carbonyl]pyridine-2-carboxamide

EXAMPLE 431

N-(2-Methoxyethyl)-5-[((4-(2-((2-ethylbutanoyl)amino)ethyl)phenylsulfonyl)amino)carbonyl]pyridine-2-carboxamide

EXAMPLE 432

N-(2-Hydroxyethyl)-5-[((4-(2-((4-n-butoxybenzoyl)amino)ethyl)phenylsulfonyl)amino)carbonyl]pyridine-2-carboxamide

EXAMPLE 433

N-Methoxycarbonylmethyl-5-[((4-(2-((2-chloro-5-methoxybenzoyl)amino)ethyl)phenylsulfonyl)amino)carbonyl]pyridine-2-carboxamide a) 5-[((4-(2-((2-chloro-5-methoxybenzoyl)amino)ethyl)phenylsulfonyl)amino)carbonyl]pyridine-2-carboxylic acid 0.8 g (1.36 mmol) of the methyl ester from Example 332 a) were hydrolyzed using 30 ml of 1N methanolic NaOH analogously to Example 202 a). After concentration in vacuo, the residue was dissolved in tetrahydrofuran, acidified with 2N aqueous HCl and concentrated, and the residue was treated with water and filtered off with suction. 0.75 g of product was isolated, M.p. 149° C. (dec.).

b) 0.7 g (1.35 mmol) of the above pyridine-2-carboxylic acid derivative was reacted analogously to Example 202 b) with 0.19 g (1.5 mmol) of glycine methyl ester hydrochloride, 0.4 ml (3 mmol) of N-ethylmorpholine, 0.33 g (1.5 mmol) of 1-hydroxybenzotriazole and 0.31 g (1.5 mmol) of N,N'-dicyclohexylcarbodiimide in 100 ml of anhydrous acetonitrile.

The insoluble matter was then filtered off, the filtrate was concentrated, the residue was taken up in 1,4-dioxane, and the solution was acidified with 2N aqueous HCl and concentrated in vacuo. The crystalline product was filtered off with suction, washed and dried. This crude product was then chromatographed on silica gel using dichloromethane/methanol (19:1). Appropriate fractions were evaporated and the residue was crystallized from hot methanol, filtered off with suction, washed with methanol and dried. 0.51 g of the title compound was obtained as colorless crystalline product, M.p. 192°–194° C.

EXAMPLE 434

N-Methoxycarbonylmethyl-5-[((4-(2-(acetylamino)ethyl)phenylsulfonyl)amino)carbonyl]pyridine-2-carboxamide

EXAMPLE 435

N-Methoxycarbonylmethyl-5-[((4-(2-(n-hexanoylamino)ethyl)phenylsulfonyl)amino)carbonyl]pyridine-2-carboxamide
M.p. 128°–130° C. (ethyl acetate)

EXAMPLE 436

N-Methoxycarbonylmethyl-5-[((4-(2-(benzoylamino)ethyl)phenylsulfonyl)amino)carbonyl]pyridine-2-carboxamide

EXAMPLE 437

N-Methoxycarbonylmethyl-5-[((4-(2-((4-chlorobenzoyl)amino)ethyl)phenylsulfonyl)amino)carbonyl]pyridine-2-carboxamide

EXAMPLE 438

N-Methoxycarbonylmethyl-5-[((4-(2-((3,4-dimethoxyphenyl)propionyl)amino)ethyl)phenylsulfonyl)amino)carbonyl]pyridine-2-carboxamide
M.p. 139°–141° C. (after chromatography using ethyl acetate/methanol (9:1) on silica gel)

EXAMPLE 439

N-Methoxycarbonylmethyl-5-[((4-(2-((3-phenyl-n-propionyl)amino)ethyl)phenylsulfonyl)amino)carbonyl]pyridine-2-carboxamide

EXAMPLE 440

N-Methoxycarbonylmethyl-5-[((4-(2-((2-phenylacetyl)amino)ethyl)phenylsulfonyl)amino)carbonyl]pyridine-2-carboxamide

EXAMPLE 441

N-Methoxycarbonylmethyl-5-[((4-(2-((phenoxyacetyl)amino)ethyl)phenylsulfonyl)amino)carbonyl]pyridine-2-carboxamide

EXAMPLE 442

N-Methoxycarbonylmethyl-5-[((4-(2-((4-fluorobenzoyl) amino)ethyl)phenylsulfonyl)amino)carbonyl]pyridine-2-carboxamide

EXAMPLE 443

N-Methoxycarbonylmethyl-5-[((4-(2-((3,4-diethoxybenzoyl)amino)ethyl)phenylsulfonyl)amino)carbonyl]pyridine-2-carboxamide M.p. 215°–217° C.

EXAMPLE 444

N-Methoxycarbonylmethyl-5-[((4-(2-((cyclohexanoyl)amino)ethyl)phenylsulfonyl)amino)carbonyl]pyridine-2-carboxamide

EXAMPLE 445

N-Methoxycarbonylmethyl-5-[((4-(2-((cyclohexylacetyl) amino)ethyl)phenylsulfonyl)amino)carbonyl]pyridine-2-carboxamide M.p. 178°–179° C. (methanol/diisopropyl ether)

EXAMPLE 446

N-Methoxycarbonylmethyl-5-[((4-(2-((2-methylpropionyl) amino)ethyl)phenylsulfonyl)amino)carbonyl]pyridine-2-carboxamide M.p. 197°–199° C. (after chromatography using ethyl acetate/methanol (9:1) on silica gel)

EXAMPLE 447

N-Methoxycarbonylmethyl-5-[((4-(2-(4-methylpentanoyl) amino)ethyl)phenylsulfonyl)amino)carbonyl]pyridine-2-carboxamide M.p. 160°–162° C. (after chromatography using ethyl acetate/methanol on silica gel)

EXAMPLE 448

N-(2-Propoxycarbonylmethyl)-5-[((4-(2-((2-chloro-5-methoxybenzoyl)amino)ethyl)phenylsulfonyl)amino)carbonyl] pyridine-2-carboxamide

EXAMPLE 449

N-(2-Propoxycarbonylmethyl)-5-[((4-(2-(acetylamino)ethyl)phenylsulfonyl)amino)carbonyl]pyridine-2-carboxamide

EXAMPLE 450

N-(2-Propoxycarbonylmethyl)-5-[((4-(2-(n-butanoylamino) ethyl)phenylsulfonyl)amino)carbonyl]pyridine-2-carboxamide

EXAMPLE 451

N-(2-Propoxycarbonylmethyl)-5-[((4-(2-(benzoylamino)ethyl)phenylsulfonyl)amino)carbonyl]pyridine-2-carboxamide

EXAMPLE 452

N-(2-Propoxycarbonylmethyl)-5-[((4-(2-((4-chlorobenzoyl) amino)ethyl)phenylsulfonyl)amino)carbonyl]pyridine-2-carboxamide

EXAMPLE 453

N-(2-Propoxycarbonylmethyl)-5-[((4-(2-((5-chloro-2-methoxybenzoyl)amino)ethyl)phenylsulfonyl)amino)carbonyl] pyridine-2-carboxamide

EXAMPLE 454

N-(2-Propoxycarbonylmethyl)-5-[((4-(2-((3-phenyl-n-propionyl)amino)ethyl)phenylsulfonyl)amino)carbonyl]pyridine-2-carboxamide

EXAMPLE 455

N-(2-Propoxycarbonylmethyl)-5-[((4-(2-((2-phenylacetyl) amino)ethyl)phenylsulfonyl)amino)carbonyl]pyridine-2-carboxamide

EXAMPLE 456

N-(2-Propoxycarbonylmethyl)-5-[((4-(2-((phenoxyacetyl) amino)ethyl)phenylsulfonyl)amino)carbonyl]pyridine-2-carboxamide

EXAMPLE 457

N-(2-Propoxycarbonylmethyl)-5-[((4-(2-((4-fluorobenzoyl) amino)ethyl)phenylsulfonyl)amino)carbonyl]pyridine-2-carboxamide

EXAMPLE 458

N-(2-Propoxycarbonylmethyl)-5-[((4-(2-((4-ethoxybenzoyl) amino)ethyl)phenylsulfonyl)amino)carbonyl]pyridine-2-carboxamide

EXAMPLE 459

N-(2-Propoxycarbonylmethyl)-5-[((4-(2-((cyclohexanoyl) amino)ethyl)phenylsulfonyl)amino)carbonyl]pyridine-2-carboxamide

EXAMPLE 460

N-(2-Propoxycarbonylmethyl)-5-[((4-(2-((cyclohexylacetyl) amino)ethyl)phenylsulfonyl)amino)carbonyl]pyridine-2-carboxamide

EXAMPLE 461

N-(2-Propoxycabonylmethyl)-5-[((4-(2-(2-methylpropionyl) amino)ethyl)phenylsulfonyl)amino)carbonyl]pyridine-2-carboxamide

EXAMPLE 462

N-(2-Propoxycarbonylmethyl)-5-[((4-(2-(2-ethylbutanonyl) amino)ethyl)phenylsulfonyl)amino)carbonyl]pyridine-2-carboxamide

EXAMPLE 463

N-Benzyloxycarbonylmethyl-5-[((4-(2-((2-chloro-5-methoxybenzoyl)amino)ethyl)phenylsulfonyl)amino)carbonyl] pyridine-2-carboxamide

EXAMPLE 464

N-Benzyloxycarbonylmethyl-5-[((4-(2-(acetylamino)ethyl)phenylsulfonyl)amino)carbonyl]pyridine-2-carboxamide

EXAMPLE 465

N-Benzyloxycarbonylmethyl-5-[((4-(2-(n-butanoylamino)ethyl)phenylsulfonyl)amino)carbonyl]pyridine-2-carboxamide

EXAMPLE 466

N-Benzyloxycarbonylmethyl-5-[((4-(2-(benzoylamino)ethyl)phenylsulfonyl)amino)carbonyl]pyridine-2-carboxamide

EXAMPLE 467

N-Benzyloxycarbonylmethyl-5-[((4-(2-((4-chlorobenzoyl)amino)ethyl)phenylsulfonyl)amino)carbonyl]pyridine-2-carboxamide

EXAMPLE 468

N-Benzyloxycarbonylmethyl-5-[((4-(2-((5-chloro-2-methoxybenzoyl)amino)ethyl)phenylsulfonyl)amino)carbonyl]pyridine-2-carboxamide

EXAMPLE 469

N-Benzyloxycarbonylmethyl-5-[((4-(2-((3-phenyl-n-propionyl)amino)ethyl)phenylsulfonyl)amino)carbonyl]pyridine-2-carboxamide

EXAMPLE 470

N-Benzyloxycarbonylmethyl-5-[((4-(2-((2-phenylacetyl)amino)ethyl)phenylsulfonyl)amino)carbonyl]pyridine-2-carboxamide

EXAMPLE 471

N-Benzyloxycarbonylmethyl-5-[((4-(2-((phenoxyacetyl)amino)ethyl)phenylsulfonyl)amino)carbonyl]pyridine-2-carboxamide

EXAMPLE 472

N-Benzyloxycarbonylmethyl-5-[((4-(2-((4-fluorobenzoyl)amino)ethyl)phenylsulfonyl)amino)carbonyl]pyridine-2-carboxamide

EXAMPLE 473

N-Benzyloxycarbonylmethyl-5-[((4-(2-((4-ethoxybenzoyl)amino)ethyl)phenylsulfonyl)amino)carbonyl]pyridine-2-carboxamide

EXAMPLE 474

N-Benzyloxycarbonylmethyl-5-[((4-(2-((cyclohexanoyl)amino)ethyl)phenylsulfonyl)amino)carbonyl]pyridine-2-carboxamide

EXAMPLE 475

N-Benzyloxycarbonylmethyl-5-[((4-(2-((cyclohexylacetyl)amino)ethyl)phenylsulfonyl)amino)carbonyl]pyridine-2-carboxamide

EXAMPLE 476

N-Benzyloxycarbonylmethyl-5-[((4-(2-(2-methylpropionyl)amino)ethyl)phenylsulfonyl)amino)carbonyl]pyridine-2-carboxamide

EXAMPLE 477

N-Benzyloxycarbonylmethyl-5-[((4-(2-(2-ethylbutanonyl)amino)ethyl)phenylsulfonyl)amino)carbonyl]pyridine-2-carboxamide

EXAMPLE 478

N-Carboxymethyl-5-[((4-(2-((2-chloro-5-methoxybenzoyl)amino)ethyl)phenylsulfonyl)amino)carbonyl]pyridine-2-carboxamide

EXAMPLE 479

N-Carboxymethyl-5-[((4-(2-(acetylamino)ethyl)phenylsulfonyl)amino)carbonyl]pyridine-2-carboxamide

EXAMPLE 480

N-Carboxymethyl-5-[((4-(2-(n-hexanoylamino)ethyl)phenylsulfonyl)amino)carbonyl]pyridine-2-carboxamide M.p. 115°–116° C. (from tetrahydrofuran/aqueous hydrochloric acid)

EXAMPLE 481

N-Carboxymethyl-5-[((4-(2-(benzoylamino)ethyl)phenylsulfonyl)amino)carbonyl]pyridine-2-carboxamide

EXAMPLE 482

N-Carboxymethyl-5-[((4-(2-((4-chlorobenzoyl)amino)ethyl)phenylsulfonyl)amino)carbonyl]pyridine-2-carboxamide

EXAMPLE 483

N-Carboxymethyl-5-[((4-(2-((3,4-dimethoxybenzoyl)amino)ethyl)phenylsulfonyl)amino)carbonyl]pyridine-2-carboxamide

EXAMPLE 484

N-Carboxymethyl-5-[((4-(2-((3-phenyl-n-propionyl)amino)ethyl)phenylsulfonyl)amino)carbonyl]pyridine-2-carboxamide

EXAMPLE 485

N-Carboxymethyl-5-[((4-(2-((2-phenylacetyl)amino)ethyl)phenylsulfonyl)amino)carbonyl]pyridine-2-carboxamide

EXAMPLE 486

N-Carboxymethyl-5-[((4-(2-((phenoxyacetyl)amino)ethyl)phenylsulfonyl)amino)carbonyl]pyridine-2-carboxamide

EXAMPLE 487

N-Carboxymethyl-5-[((4-(2-((4-fluorobenzoyl)amino)ethyl)phenylsulfonyl)amino)carbonyl]pyridine-2-carboxamide

EXAMPLE 488

N-Carboxymethyl-5-[((4-(2-((3,4-diethoxybenzoyl)amino)ethyl)phenylsulfonyl)amino)carbonyl]pyridine-2-carboxamide M.p. >230° C. (from aqueous hydrochloric acid)

EXAMPLE 489

N-Carboxymethyl-5-[((4-(2-((cyclohexanoyl)amino)ethyl)phenylsulfonyl)amino)carbonyl]pyridine-2-carboxamide

EXAMPLE 490

N-Carboxymethyl-5-[((4-(2-((cyclohexylacetyl)amino)ethyl)phenylsulfonyl)amino)carbonyl]pyridine-2-carboxamide
M.p. 154°–156° C. (from aqueous hydrochloric acid)

EXAMPLE 491

N-Carboxymethyl-5-[((4-(2-(2-methylpropionyl)amino)ethyl)phenylsulfonyl)amino)carbonyl]pyridine-2-carboxamide
M.p. 269°–271° C. (from aqueous hydrochloric acid)

EXAMPLE 492

N-Carboxymethyl-5-[((4-(2-(4-methylpentanoyl)amino)ethyl)phenylsulfonyl)amino)carbonyl]pyridine-2-carboxamide
M.p. 126°–128° C. (from aqueous hydrochloric acid)

EXAMPLE 493

N-Methoxycarbonylmethyl-5-[((3-(2-((2-chloro-5-methoxybenzoyl)amino)ethyl)phenylsulfonyl)amino)carbonyl]pyridine-2-carboxamide

EXAMPLE 494

N-Methoxycarbonylmethyl-5-[((3-(2-(acetylamino)ethyl)phenylsulfonyl)amino)carbonyl]pyridine-2-carboxamide

EXAMPLE 495

N-Methoxycarbonylmethyl-5-[((3-(2-(n-butanoylamino)ethyl)phenylsulfonyl)amino)carbonyl]pyridine-2-carboxamide

EXAMPLE 496

N-Methoxycarbonylmethyl-5-[((3-(2-(benzoylamino)ethyl)phenylsulfonyl)amino)carbonyl]pyridine-2-carboxamide

EXAMPLE 497

N-Methoxycarbonylmethyl-5-[((3-(2-((4-chlorobenzoyl)amino)ethyl)phenylsulfonyl)amino)carbonyl]pyridine-2-carboxamide

EXAMPLE 498

N-Methoxycarbonylmethyl-5-[((3-(2-((5-chloro-2-methoxybenzoyl)amino)ethyl)phenylsulfonyl)amino)carbonyl]pyridine-2-carboxamide

EXAMPLE 499

N-Methoxycarbonylmethyl-5-[((3-(2-((3-phenyl-n-propionyl)amino)ethyl)phenylsulfonyl)amino)carbonyl]pyridine-2-carboxamide

EXAMPLE 500

N-Methoxycarbonylmethyl-5-[((3-(2-((3-phenylacetyl)amino)ethyl)phenylsulfonyl)amino)carbonyl]pyridine-2-carboxamide

EXAMPLE 501

N-Methoxycarbonylmethyl-5-[((4-(3-((phenoxyacetyl)amino)ethyl)phenylsulfonyl)amino)carbonyl]pyridine-2-carboxamide

EXAMPLE 502

N-Methoxycarbonylmethyl-5-[((3-(2-((4-fluorobenzoyl)amino)ethyl)phenylsulfonyl)amino)carbonyl]pyridine-2-carboxamide

EXAMPLE 503

N-Methoxycarbonylmethyl-5-[((3-(2-((4-ethoxybenzoyl)amino)ethyl)phenylsulfonyl)amino)carbonyl]pyridine-2-carboxamide

EXAMPLE 504

N-Methoxycarbonylmethyl-5-[((3-(2-((cyclohexanoyl)amino)ethyl)phenylsulfonyl)amino)carbonyl]pyridine-2-carboxamide

EXAMPLE 505

N-Methoxycarbonylmethyl-5-[((3-(2-((cyclohexylacetyl)amino)ethyl)phenylsulfonyl)amino)carbonyl]pyridine-2-carboxamide

EXAMPLE 506

N-Methoxycarbonymethyl-5-[((3-(2-(2-methylpropionyl)amino)ethyl)phenylsulfonyl)amino)carbonyl]pyridine-2-carboxamide

EXAMPLE 507

N-Methoxycarbonylmethyl-5-[((3-(2-(2-ethylbutanonyl)amino)ethyl)phenylsulfonyl)amino)carbonyl]pyridine-2-carboxamide

EXAMPLE 508

N-(2-Hydroxyethyl)-5-[((4-((4-phenyl-n-butanoyl)aminophenylsulfonyl)amino)carbonyl]pyridine-2-carboxamide a) 4-((Phenyl-n-butanoyl)amino)benzenesulfonamide
16.5 g (0.1 mol) of 4-phenylbutyric acid were treated at 0° C. with 11.1 g (0.11 mol, 15.2 ml) of triethylamine in 300 ml of anhydrous tetrahydrofuran. After 30 min, 12 g (0.11 mol, 10.5 ml) of ethyl chloroformate were added dropwise at 0° C. A solution of 18.1 g (0.105 mol) of 4-aminobenzenesulfonamide in 150 ml of anhydrous tetrahydrofuran was added dropwise at –10° C. to this thick suspension. The mixture was stirred at 0° C. for 1 h and at 25° C. for 1 h, and concentrated in vacuo, and the residue was treated with aqueous hydrochloric acid. The crystalline crude product was washed with water and recrystallized from 250 ml of methanol; yield 18 g; M.p. 166°–168° C.

b) Methyl 5-[((4-((4-phenyl-n-butanoyl)amino)phenylsulfonyl)amino)carbonyl]pyridine-2-carboxylate Analogously to Example 112b), 1.8 g (10 mmol) of 2-methoxycarbonylpyridine-5-carboxylic acid were reacted with 3.2 g (10 mmol) of the above benzenesulfonamide, 2.1 g (10 mmol) of N,N'-dicyclohexylcarbodiimide and 1.2 g (10 mmol) of 4-N,N-dimethylaminopyridine in 300 ml of acetonitrile.

The insoluble matter was filtered off, the filtrate was concentrated, the residue was treated with aqueous hydrochloric acid (pH 1) and the fine crystalline product was filtered off with suction. This was dissolved in N,N-dimethylformamide and treated with water until the onset of turbidity. The crystalline crude product was washed with water and dried; 3.3 g; M.p. 258°–264° C.

After chromatography with ethyl acetate/methanol (3:1) on silica gel, appropriate fractions were evaporated and the residue was recrystallized from methanol. 1.4 g of colorless crystalline product were isolated; M.p. 258° C. (with decomposition).

c) The title compound was obtained by stirring 0.3 g (0.62 mmol) of the above methyl ester at 80° C. for 2 h in 5 ml of 2-aminoethanol. The excess reagent was distilled off in vacuo, the residue was dissolved in a little tetrahydrofuran, the solution was acidified with 2N aqueous HCl and concentrated in vacuo, and the crystalline precipitate was filtered off with suction, washed with water and dried. 0.21 g of the title compound was obtained; M.p. 278°–280° C.

EXAMPLE 509

N-(2-Hydroxyethyl)-5-[((4-(3-phenyl-n-propionylamino)-phenylsulfonyl)amino)carbonyl]pyridine-2-carboxamide

EXAMPLE 510

N-(2-Hydroxyethyl)-5-[((4-(2-phenylacetylamino)phenylsulfonyl)amino)carbonyl]pyridine-2-carboxamide

EXAMPLE 511

N-(2-Hydroxyethyl)-5-[((4-benzoylamino)phenylsulfonyl)amino)carbonyl]pyridine-2-carboxamide

EXAMPLE 512

N-(2-Hydroxyethyl)-5-[((4-(acetylamino)phenylsulfonyl)amino)carbonyl]pyridine-2-carboxamide

EXAMPLE 513

N-(2-Hydroxyethyl)-5-[((4-(n-propionylamino)phenylsulfonyl)amino)carbonyl]pyridine-2-carboxamide

EXAMPLE 514

N-(2-Hydroxyethyl)-5-[((4-(n-hexanoylamino)phenylsulfonyl)amino)carbonyl]pyridine-2-carboxamide

EXAMPLE 515

N-(2Hydroxethyl)-5-[((4-((2-phenoxyacetyl)amino)phenylsulfonyl)amino)carbonyl]pyridine-2-carboxamide

EXAMPLE 516

N-(2-Hydroxyethyl)-5-[((4-(n-butanoylamino)phenylsulfonyl)amino)carbonyl]pyridine-2-carboxamide

EXAMPLE 517

N-(2-Hydroxyethyl)-5-[((4-(cyclohexanoylamino)phenylsulfonyl)amino)carbonyl]pyridine-2-carboxamide

EXAMPLE 518

N-(2-Hydroxyethyl)-5-[((4-(cyclohexylacetyl)amino)phenylsulfonyl)amino)carbonyl]pyridine-2-carboxamide

EXAMPLE 519

N-(2-Methoxyethyl)-5[((4-(4-phenyl-n-butanoylamino)phenylsulfonyl)amino)carbonyl]pyridine-2-carboxamide

EXAMPLE 520

N-(2-Methoxyethyl)-5-[((4-(3-phenyl-n-propionylamino)phenylsulfonyl)amino)carbonyl]pyridine-2-carboxamide

EXAMPLE 521

N-(2-Methoxyethyl)-5-[((4-(2-phenylacetylamino)phenylsulfonyl)amino)carbonyl]pyridine-2-carboxamide

EXAMPLE 522

N-(2-Methoxyethyl)-5-[((4-(benzoylamino)phenylsulfonyl)amino)carbonyl]pyridine-2-carboxamide

EXAMPLE 523

N-(2-Methoxyethyl)-5-[((4-(acetylamino)phenylsulfonyl)amino)carbonyl]pyridine-2-carboxamide

EXAMPLE 524

N-(2-Methoxyethyl)-5-[((4-(n-propionylamino)phenylsulfonyl)amino)carbonyl]pyridine-2-carboxamide

EXAMPLE 525

N-(2-Methoxyethyl)-5-[((4-(n-hexanoylamino)phenysulfonyl)amino)carbonyl]pyridine-2-carboxamide

EXAMPLE 526

N-(2-Methoxyethyl)-5-[((4-(2-phenoxyacetyl)amino)phenylsulfonyl)amino)carbonyl]pyridine-2-carboxamide

EXAMPLE 527

N-(2-Methoxyethyl)-5-[((4-(n-butanoylamino)phenylsulfonyl)amino)carbonyl]pyridine-2-carboxamide

EXAMPLE 528

N-(2-Methoxyethyl)-5-[((4-(cyclohexanoylamino)phenylsulfonyl)amino)carbonyl]pyridine-2-carboxamide

EXAMPLE 529

N-(2-Methoxyethyl)-5-[((4-(cyclohexylacetyl)amino)phenylsulfonyl)amino)carbonyl]pyridine-2-carboxamide

EXAMPLE 530

N-(2-Propoxycarbonylmethyl)-5-[(((4-phenyl-n-butyl)-sulfonyl)amino)carbonyl]pyridine-2-carboxamide

EXAMPLE 531

N-(2-Propoxycarbonylmethyl)-5-[(((2-phenoxyethyl)-sulfonyl)amino)carbonyl]pyridine-2-carboxamide

EXAMPLE 532

N-(2-Propoxycarbonylmethyl)-5-[((2-(4-fluorophenoxy)-ethylsulfonyl)amino)carbonyl]pyridine-2-carboxamide

EXAMPLE 533

N-Benzyloxycarbonylmethyl-5-[((phenylmethylsulfonyl)-amino)carbonyl]pyridine-2-carboxamide

EXAMPLE 534

N-Benzyloxycarbonylmethyl-5-[(((2-phenylethyl)-sulfonyl)amino)carbonyl]pyridine-2-carboxamide

EXAMPLE 535

N-Benzyloxycarbonylmethyl-5-[(((2-(4-fluorophenyl)-ethyl)sulfonyl)amino)carbonyl]pyridine-2-carboxamide

EXAMPLE 536

N-Benzyloxycarbonylmethyl-5-[(((2-(4-methoxyphenyl)-ethyl)sulfonyl)amino)carbonyl]pyridine-2-carboxamide

EXAMPLE 537

N-Benzyloxycarbonylmethyl-5-[(((3-phenyl-n-propyl)-sulfonyl) amino)carbonyl]pyridine-2-carboxamide

EXAMPLE 538

N-Benzyloxycarbonylmethyl-5-[(((4-phenyl-n-butyl)-sulfonyl)amino)carbonyl]pyridine-2-carboxamide

EXAMPLE 539

N-Benzyloxycarbonylmethyl-5-[(((2-phenoxyethyl)-sulfonyl)amino)carbonyl]pyridine-2-carboxamide

EXAMPLE 540

N-Benzyloxycarbonylmethyl-5-[(((2-(4-fluorophenoxy)-ethyl)sulfonyl)amino)carbonyl]pyridine-2-carboxamide

EXAMPLE 541

N-Carboxymethyl-5-[((phenylmethylsulfonyl)amino)carbonyl]-pyridine-2-carboxamide

EXAMPLE 542

N-Carboxymethyl-5-[(((2-phenylethyl)sulfonyl)amino)carbonyl]-pyridine-2-carboxamide

EXAMPLE 543

N-Carboxymethyl-5-[(((2-(4-fluorophenyl)ethylsulfonyl)amino)-carbonyl]pyridine-2-carboxamide

EXAMPLE 544

N-Carboxymethyl-5-[(((2-4-methoxyphenyl)ethyl)sulfonyl)amino)-carbonyl]pyridine-2-carboxamide

EXAMPLE 545

N-Carboxymethyl-5-[(((3-phenyl-n-propyl)sulfonyl)amino)-carbonyl]pyridine-2-carboxamide

EXAMPLE 546

N-Carboxymethyl-5-[(((4-phenyl-n-butyl)sulfonyl)amino)carbonyl]-pyridine-2-carboxamide

EXAMPLE 547

N-Carboxymethyl-5-[(((2-phenoxyethyl)sulfonyl)amino)carbonyl]-pyridine-2-carboxamide

EXAMPLE 548

N-Carboxymethyl-5-[(((2-(4-fluorophenoxy)ethyl)sulfonyl)amino)-carbonyl]pyridine-2-carboxamide

EXAMPLE 549

N-(3-Pentoxycarbonylmethyl)-5-[(((phenylmethylsulfonyl)-amino)carbonyl]pyridine-2-carboxamide

EXAMPLE 550

N-(3-Pentoxycarbonylmethyl)-5-[(((2-phenylethyl)-sulfonyl)amino)carbonyl]pyridine-2-carboxamide

EXAMPLE 551

N-(3-Pentoxycarbonylmethyl)-5-[(((2-(4-fluorophenyl)-ethyl)sulfonyl)amino)carbonyl]pyridine-2-carboxamide

EXAMPLE 552

N-(3-Pentoxycarbonylmethyl)-5-[(((2-(4-methoxyphenyl)-ethylsulfonyl)amino)carbonyl]pyridine-2-carboxamide

EXAMPLE 553

N-(4-Heptyloxycarbonylmethyl)-5-[(((3-phenyl-n-propyl)-sulfonyl)amino)carbonyl]pyridine-2-carboxamide

EXAMPLE 554

N-(R-2-Butoxycarbonylmethyl)-5-[(((4-phenyl-n-butyl)-sulfonyl)amino)carbonyl]pyridine-2-carboxamide

EXAMPLE 555

N-(n-Octyloxycarbonylmethyl)-5-[(((2-phenoxyethyl)-sulfonyl)amino)carbonyl]pyridine-2-carboxamide

EXAMPLE 556

N-Cyclohexyloxycarbonylmethyl-5-[(((2-(4-fluorophenoxy)ethyl)sulfonyl)amino)carbonyl]pyridine-2-carboxamide

EXAMPLE 557

N-(2-Hydroxyethyl)-5-[((4-(2-((3,4-dimethoxybenzoyl)-amino)ethyl)phenylsulfonyl)amino)carbonyl]pyridine-2-carboxamide

EXAMPLE 558

N-(2-Acetoxyethyl)-5-[((4-(2-((3,4-dimethoxybenzoyl)-amino)ethyl)phenylsulfonyl)amino)carbonyl]pyridine-2-carboxamide

EXAMPLE 559

N-(2-Hydroxyethyl)-5-[((4-(2-((2,5-dimethoxybenzoyl)-amino)ethyl)phenylsulfonyl)amino)carbonyl]pyridine-2-carboxamide

EXAMPLE 560

N-(2-Methoxyethyl)-5-[((4-(2-((3,4-dimethoxybenzoyl)-amino)ethyl)phenylsulfonyl)amino)carbonyl]pyridine-2-carboxamide

EXAMPLE 561

N-(2-Ethoxyethyl)-5-[((4-(2-((3,4-dimethoxybenzoyl)-amino)ethyl)phenylsulfonyl)amino)carbonyl]pyridine-2-carboxamide

EXAMPLE 562

N-(2-Methoxyethyl)-5-[((4-(2-((2,5-dimethoxybenzoyl)-amino)ethyl)phenylsulfonyl)amino)carbonyl]pyridine-2-carboxamide

EXAMPLE 563

N-Methoxycarbonylmethyl-5-[((4-(2-((3,4-dimethoxybenzoyl)amino)ethyl)phenylsulfonyl)amino)carbonyl]-pyridine-2-carboxamide

EXAMPLE 564

N-Ethoxycarbonylmethyl-5-[((4-(2-((3,4-dimethoxybenzoyl)amino)ethyl)phenylsulfonyl)amino)carbonyl]-pyridine-2-carboxamide

EXAMPLE 565

N-Methoxycarbonylmethyl-5-[((4-(2-((2,5-dimethoxybenzoyl)amino)ethyl)phenylsulfonyl)amino)carbonyl]-pyridine-2-carboxamide

EXAMPLE 566

N-(2-Propoxycarbonylmethyl)-5-[((4-(2-((3,4-dimethoxybenzoyl)amino)ethyl)phenylsulfonyl)amino)carbonyl]-pyridine-2-carboxamide

EXAMPLE 567

N-(3-Pentoxycarbonylmethyl)-5-[((4-(2-((3,4-dimethoxybenzoyl)amino)ethyl)phenylsulfonyl)amino)carbonyl]-pyridine-2-carboxamide

EXAMPLE 568

N-(2-Propoxycarbonylmethyl)-5-[((4-(2-((2,5-dimethoxybenzoyl)amino)ethyl)phenylsulfonyl)amino)carbonyl]-pyridine-2-carboxamide

EXAMPLE 569

N-Carboxymethyl-5-[((4-(2-((3,4-dimethoxybenzoyl)amino)ethyl)-phenylsulfonyl)amino)carbonyl]pyridine-2-carboxamide

EXAMPLE 570

N-(Cyclohexyloxycarbonylmethyl)-5-[((4-(2-((3,4-dimethoxybenzoyl)amino)ethyl)phenylsulfonyl)amino)-carbonyl]pyridine-2-carboxamide

EXAMPLE 571

N-Carboxymethyl-5-[((4-(2-((2,5-dimethoxybenzoyl)amino)ethyl)-phenylsulfonyl)amino)carbonyl]pyridine-2-carboxamide

We claim:
1. A compound of the formula wherein $R_1$, $R_2$, $R_3$ and $R_4$ are independently hydrogen or $(C_1-C_4)$alkyl;

$R_5$ is an unbranched $(C_1-C_4)$alkyl radical which is substituted by hydroxyl, carboxyl, $(C_1-C_4)$alkoxy, phenoxy, benzyloxy, $(C_1-C_9)$alkoxycarbonyl, phenoxycarbonyl, $(C_7-C_{11})$phenylalkyloxycarbonyl, $(C_3-C_8)$cycloalkoxycarbonyl, $(C_1-C_{12})$alkylcarbonyloxy, $(C_3-C_8)$cycloalkylcarbonyloxy, benzoyloxy, phenoxycarbonyloxy, $(C_7-C_{11})$phenylalkoxycarbonyloxy, $(C_3-C_8)$cycloalkoxycarbonyloxy, carbamoyl, N-$(C_1-C_6)$alkylcarbomoyl, N,N-di$(C_1-C_6)$alkylcarbamoyl, N-$(C_3-C_8)$cycloalkylcarbamoyl, N-phenylcarbamoyl, N-$(C_7-C_{11})$phenylalkylcarbamoyl, hydroxy$(C_1-C_4)$alkylcarbamoyl, acyloxy$(C_1-C_4)$alkylcarbamoyl, $(C_1-C_6)$alkoxy$(C_1-C_6)$alkylcarbamoyl, carbamoyloxy, N-$(C_1-C_6)$alkylcarbamoyloxy, N,N-di$(C_1-C_6)$alkylcarbamoyloxy or $(C_3-C_8)$cycloalkylcarbamoyloxy;

$R_6$ is hydrogen or a 1 or 2 valent physiologically utilizable cation or ammonium ion;

$R_7$ is hydrogen, fluorine, chlorine, $(C_1-C_6)$cycloalkyl, $(C_6-C_{12})$aryl, $(C_3-C_{12})$alkenyl, phenyl, $(C_1-C_6)$alkoxy, phenoxy, —(ch$_2$)$_x$C$_f$H$_{2f+1-g}$F$_g$, carbamoyl, N-$(C_1-C_{10})$alkylcarbamoyl, N,N-di$(C_1-C_8)$alkylcarbamoyl, N-$(C_3-C_8)$cycloalkylcarbamoyl, N-phenylcarbamoyl, N-$(C_7-C_{11})$phenylalkylcarbamoyl, N-$(C_1-C_8)$alkyl-N-phenylcarbamoyl, N-$(C_1-C_8)$alkyl-N-$(C_7-C_{11})$phenylalkylcarbamoyl, N-$((C_1-C_{10})$alkoxy$(C_1-C_8)$alkyl)carbamoyl, N-phenoxy$(C_1-C_8)$alkylcarbamoyl, N-$((C_7-C_{16})$phenylalkyloxy$(C_1-C_8)$alkyl)carbamoyl, N-$(C_1-C_8)$alkyl-N-$((C_1-C_6)$alkoxy$(C_1-C_8)$alkyl)carbamoyl, N-$(C_1-C_8)$alkyl-N-(phenoxy$(C_1-C_8)$alkyl)carbamoyl, N-$(C_1-C_8)$alkyl-N-$((C_7-C_{16})$phenylalkyloxy$(C_1-C_8)$alkyl)carbamoyl, $(C_1-C_8)$alkanoylamino, $(C_3-C_8)$cycloalkanoylamino, phenylamino, $(C_7-C_{11})$phenylalkanoylamino, $(C_1-C_8)$alkanoyl-N-$(C_1-C_{10})$alkylamino, $(C_3-C_8)$cycloalkanoyl-N-$(C_1-C_6)$alkylamino, benzoyl-N-$(C_1-C_{10})$alkylamino, $(C_7-C_{11})$phenylalkanoyl-N-$(C_1-C_8)$alkylamino, $(C_1-C_{10})$alkanoylamino$(C_1-C_8)$alkyl, $(C_3-C_8)$cyclolalkanoylamino$(C_1-C_8)$alkyl, phenylamino$(C_1-C_8)$alkyl or $(C_7-C_{11})$phenylalkanoylamino$(C_1-C_8)$alkyl;

wherein the phenyl of W group is optionally substituted with one to three substituents independently selected from the group of fluorine, chlorine, trifluoromethyl, hydroxyl, carboxyl, $(C_1-C_4)$alkoxy, phenoxy, benzyloxy, $(C_1-C_9)$alkoxycarbonyl, phenoxycarbonyl, $(C_7-C_{11})$phenylalkoxycarbonyl, $(C_3-C_8)$cycloalkoxycarbonyl, $(C_1-C_{12})$alkoxycarbonyloxy, $(C_3-C_8)$cycloalkylcarbonyloxy, benzoyloxy, $(C_7-C_{11})$phenalkylcarbonyloxy, $(C_1-C_8)$alkoxycarbonyloxy, phenoxycarbonyloxy, $(C_7-C_{11})$phenalkyloxycarbonyloxy, $(C_3-C_8)$cycloalkoxycarbonyloxy, carbamoyl, N-$(C_1-C_6)$alkylcarbamoyl, N,N-di$(C_1-C_6)$alkylcarbamoyl, N-$(C_3-C_8)$cycloalkylcarbamoyl, N-phenylcarbamoyl, N-$(C_7-C_{11})$phenalkylcarbamoyl, hydroxy$(C_1-C_4)$alkylcarbamoyl, acyloxy$(C_1-C_4)$alkylcarbamoyl, carbamoyloxy, N-$(C_1-C_8)$alkylcarbamoyloxy, N,N-di$(C_1-C_8)$alkylcarbamoyloxy or N-$(C_3-C_8)$cycloalkylcarbamoyl;

n is 0 or 1;

f is 1 to 5;

g is 0,1 to (2f+1).

2. A compound of the formula

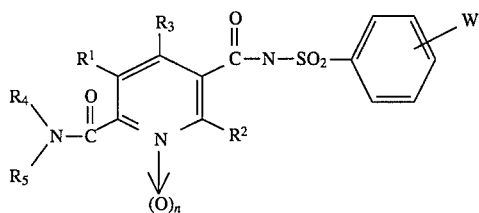

wherein

R₁, R₂, R₃ and R₄ are independently hydrogen or $(C_1-C_4)$alkyl;

R₅ is an unbranched $(C_1-C_4)$alkyl radical which is substituted by hydroxyl, carboxyl, $(C_1-C_4)$alkoxy, phenoxy, benzyloxy, $(C_1-C_9)$alkoxycarbonyl, phenoxycarbonyl, $(C_7-C_{11})$phenylalkyloxycarbonyl, $(C_3-C_8)$cycloalkoxycarbonyl, $(C_1-C_{12})$alkylcarbonyloxy, $(C_3-C_8)$cycloalkylcarbonyloxy, benzoyloxy, $(C_7-C_{11})$phenylalkylcarbonyloxy, $(C_1-C_8)$alkoxycarbonyloxy, phenoxycarbonyloxy, $(C_7-C_{11})$phenylalkoxycarbonyloxy, $(C_3-C_8)$cycloalkoxycarbonyloxy, carbamoyl, N-$(C_1-C_6)$alkylcarbomoyl, N,N-di$(C_1-C_6)$alkylcarbamoyl, N-$(C_3-C_8)$cycloalkylcarbamoyl, N-phenylcarbamoyl, N-$(C_7-C_{11})$phenylalkylcarbamoyl, hydroxy$(C_1-C_4)$alkylcarbamoyl, acyloxy$(C_1-C_4)$alkylcarbamoyl, $(C_1-C_6)$alkoxy$(C_1-C_6)$alkylcarbamoyl, carbamoyloxy, N-$(C_1-C_6)$alkylcarbamoyloxy, N,N-di$(C_1-C_6)$alkylcarbamoyloxy or $(C_3-C_8)$cycloalkylcarbamoyloxy;

R₆ is hydrogen or a 1 or 2 valent physiologically utilizable cation or an ammonium ion; W is hydrogen, fluorine, chlorine, $(C_1-C_6)$alkyl, $(C_3-C_6)$cycloalkyl, $(C_6-C_{12})$aryl, $(C_3-C_{12})$alkenyl, phenyl, $(C_1-C_6)$alkoxy, phenoxy, —O(ch₂)ₓC$_f$H$_{(2f+1-g)}$F$_g$, carbamoyl, N-$(C_1-C_{10})$alkylcarbamoyl, N,N-di$(C_1-C_8)$alkylcarbamoyl, N-$(C_3-C_8)$cycloalkylcarbamoyl, N-phenylcarbamoyl, N-$(C_7-C_{11})$phenylalkylcarbamoyl, N-$(C_1-C_8)$alkyl-N-phenylcarbamoyl, N-$(C_1-C_8)$alkyl-N-$(C_7-C_{11})$phenylalkylcarbamoyl, N-(($C_1-C_{10}$)alkoxy$(C_1-C_8)$alkyl)carbamoyl, N-phenoxy$(C_1-C_8)$alkylcarbamoyl, N-(($C_7-C_{16}$)phenylalkyloxy$(C_1-C_8)$alkyl)carbamoyl, N-$(C_1-C_8)$alkyl-N-(($C_1-C_6$)alkoxy$(C_1-C_8)$alkyl)carbamoyl, N-$(C_1-C_8)$alkyl-N-(phenoxy$(C_1-C_8)$alkyl)carbamoyl, N-$(C_1-C_8)$alkyl-N-(($C_7-C_{16}$)phenylalkyloxy$(C_1-C_8)$alkyl)carbamoyl, $(C_1-C_8)$alkanoylamino, $(C_3-C_8)$cycloalkanoylamino, phenylamino, $(C_7-C_{11})$phenylalkanoylamino, $(C_1-C_8)$alkanoyl-N-$(C_1-C_{10})$alkylamino, $(C_3-C_8)$cycloalkanoyl-N-$(C_1-C_6)$alkylamino, benzoyl-N-$(C_1-C_{10})$alkylamino, $(C_7-C_{11})$phenylalkanoyl-N-$(C_1-C_8)$alkylamino, $(C_1-C_{10})$alkanoylamino$(C_1-C_8)$alkyl, $(C_3-C_8)$alkyl, $(C_3-C_8)$cyclolalkanoylamino $(C_1-C_8)$alkyl, phenylamino$(C_1-C_8)$alkyl or $(C_7-C_{11})$phenylalkanoylamino$(C_1-C_8)$alkyl;

wherein the phenyl of W group is optionally substituted with one or two substituents independently selected from the group of fluorine, chlorine, hydroxyl, $(C_1-C_6)$alkyl, $(C_1-C_4)$alkoxy, $(C_1-C_4)$alkoxycarbonyl, $(C_1-C_5)$alkylcarbonyloxy and trifluoromethyl;

n is 0 or 1;

f is 1 to 5;

g is 0,1 to (2f+1).

3. The compound of claim 2 wherein the 1 or 2 valent physiologically utilizable cation is Na⁺, K⁺, Mg²⁺ or Ca²⁺; the ammonium ion is H₃N⁺C(CH₂OH)₃;

R₅ is carboxyl, hydroxyl, $(C_1-C_9)$alkoxycarbonyl or $(C_1-C_4)$alkoxy; and

W is hydrogen, fluorine, $(C_1-C_6)$alkoxy, N-$(C_1-C_{10})$alkylcarbamoyl, $(C_7-C_{11})$phenylalkylcarbamoyl, N-(($C_1-C_{10}$)alkoxy$(C_1-C_8)$alkyl)carbamoyl, N-(di$(C_1-C_4)$alkoxy$(C_7-C_{11})$phenylalkyl)carbamoyl, N-((chloro$(C_1-C_4)$alkoxy)$(C_7-C_{11})$phenylalkyl) carbamoyl, $(C_1-C_{10})$alkanoylamino$(C_1-C_8)$alkyl, $(C_3-C_8)$cycloalkanoylamino$(C_1-C_8)$alkyl, $(C_7-C_{11})$phenylalkanoylamino$(C_1-C_8)$alkyl or (di$(C_1-C_4)$alkoxy$(C_7-C_{11})$phenylalkanoyl)amino $(C_1-C_8)$alkyl.

4. The compound of claim 2 which is N-carboxymethyl-5-[((4-(2-((cyclohexylacetyl)amino)ethyl) phenylsulfonyl) amino)carbonyl]pyridine-2-carboxamide, N-carboxymethyl-5-[((4-(2-(2-methylpropionyl)amino)ethyl)phenylsulfonyl)-amino)carbonyl]pyridine-2-carboxamide or N-carboxymethyl-5-[((4-(2-(4-methylpentanoyl)amino)ethyl)phenylsulfonyl)amino)carbonyl]pyridine-2-carboxamide.

5. An antifibrotic composition containing an effective amount of a compound as claimed in claim 1 and a pharmaceutically acceptable carrier.

6. A method of treating a patient in need of relief from a fibrotic disease which comprises administering to the patient an effective amount of a compound as claimed in claim 1.

7. The compound N-carboxymethyl-5-[((4-(2-(benzoylamino)ethyl)phenylsulfonyl)-amino)carbonyl]pyridine-2-carboxamide.

8. The compound N-carboxymethyl-5-[((4-(2-((3,4-diethoxybenzoyl)amino)ethyl)-phenylsulfonyl)amino)carbonyl]pyridine-2-carboxamide.

* * * * *